US005891637A

United States Patent [19]

Ruppert

[11] Patent Number: 5,891,637

[45] Date of Patent: Apr. 6, 1999

[54] CONSTRUCTION OF FULL LENGTH CDNA LIBRARIES

[75] Inventor: Siegfried J.W. Ruppert, San Francisco, Calif.

[73] Assignee: Genentech, Inc., South San Francisco, Calif.

[21] Appl. No.: 929,967

[22] Filed: Sep. 15, 1997

Related U.S. Application Data

[63] Continuation of Ser. No. 732,861, Oct. 15, 1996, abandoned.

[51] Int. Cl.[6] ...................... C12Q 1/68

[52] U.S. Cl. ...................... 435/6; 435/91.2; 435/172.3; 435/252.33; 435/194

[58] Field of Search ...................... 435/6, 91.2, 172.3, 435/252.33, 194

[56] References Cited

U.S. PATENT DOCUMENTS

| | | | |
|---|---|---|---|
| 4,943,531 | 7/1990 | Goff et al. | 435/194 |
| 5,525,486 | 6/1996 | Honjo et al. | 435/69.1 |
| 5,536,637 | 7/1996 | Jacobs | 435/6 |

OTHER PUBLICATIONS

Maruyama et al., *Gene* vol. 138, 1994, pp. 171–174.

Kanda et al. *BBA,* vol. 1163, 1993, pp. 223–226.

Ausubel, "Construction of Recombinant DNA Libraries" *Current Protocols in Molecular Biology,* 1996:John Wiley & Sons, Inc. vol. 1:Chapter 5 (1991).

Gubler et al., "A Simple and Very Efficient Method for Generating cDNA Libraries" *Gene* 25:263–269 (1983).

Kato et al., "Construction of a human full–length cDNA bank" *Gene* 25:243–250 (1994).

Klein et al., "Selection for Genes Encoding Secreted Proteins and Receptors" *Proc. Natl. Acad. Sci. USA* 93:7108–7113 (Jul. 1996).

Okayama et al., "High–Efficiency Cloning of Full–Length cDNA" *Molecular & Biology* 2(2):161–170 (Feb. 1982).

Roth et al., "Purification and Characterization of Murine Retroviral Reverse Transcriptase Expressed in *Escherichia coli" Journal of Biological Chemistry* 260(16):9326–9335 (1985).

Seed et al., "Representation of DNA Sequences in Recombinant DNA Libraries Prepared by Restriction Enzyme Partial Digestion" *Gene* 19:201–209 (1982).

Tanese et al., "Expression of enzymatically active reverse transcriptase in *Escherichia coli" Proc. Natl. Acad. Sci. USA* 82:4944–4948 (1985).

Tashiro et al., "Signal Sequence Trap: A Cloning Strategy for Secreted Proteins and Type I Membrane Proteins" *Science*261:600–603 (1993).

*Primary Examiner*—James Ketter

*Attorney, Agent, or Firm*—Ginger R. Dreger

[57] ABSTRACT

A method of producing cDNA from mRNA is described in which the 5' end of mRNA is capped and introduced into a vector so that both the 5' and 3' ends become annealed to flanking sequences of the vector. Reverse transcriptase is then used to convert the mRNA into dscDNA, the reverse transcriptase being employed in vivo, in vitro or using a combination of these approaches. Preferably, the conversion of mRNA to dscDNA is carried out in a cell line transformed with a second vector producing the reverse transcriptase, the cell line supplying the other enzymes and materials needed for cDNA synthesis. Also described are applications of this method to construct and screen cDNA libraries and cell lines transformed with both vectors.

35 Claims, 36 Drawing Sheets

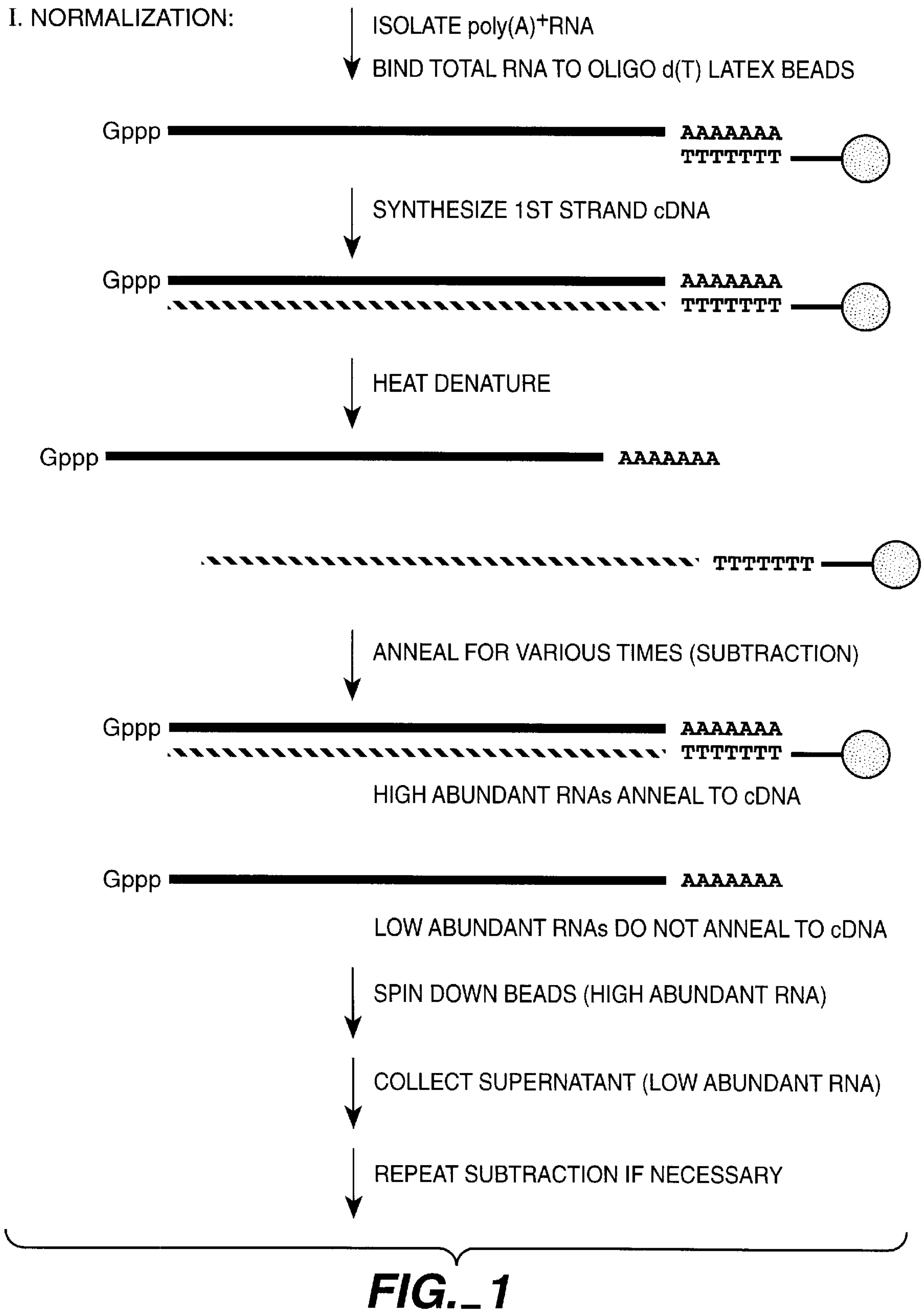
FIG._1

II. OLIGO CAPPING OF mRNA:
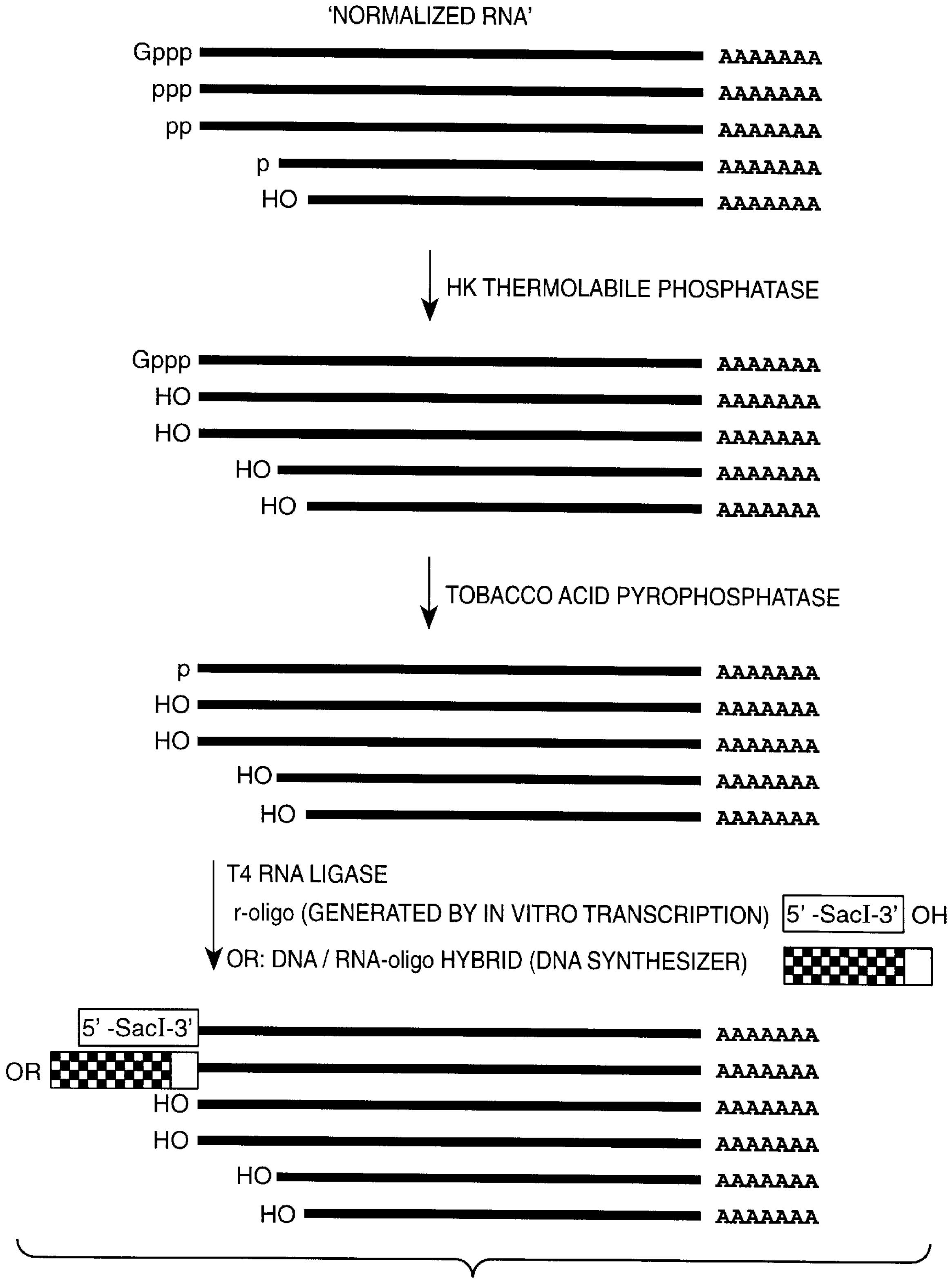
FIG._2

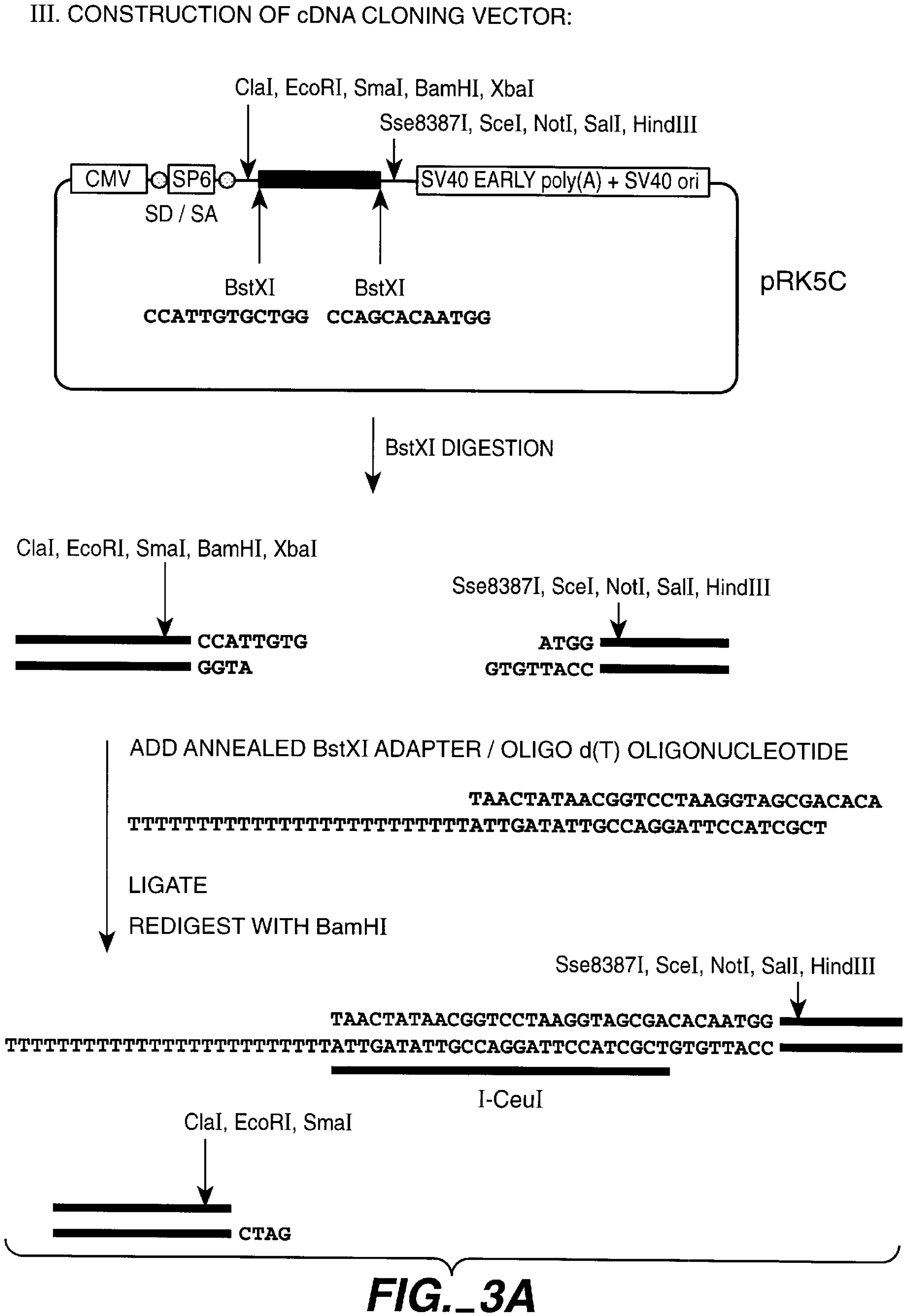
FIG._3A

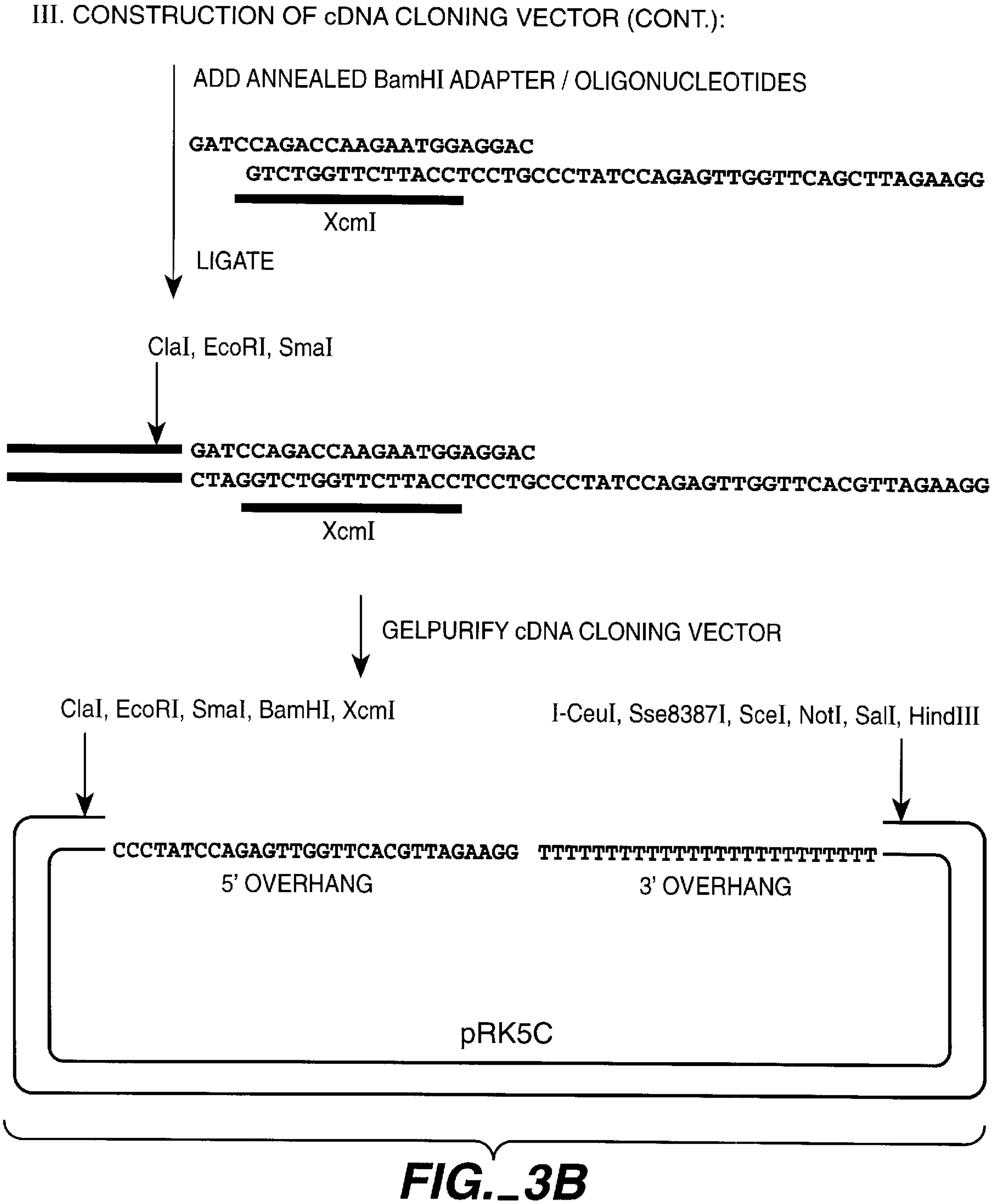
FIG._3B

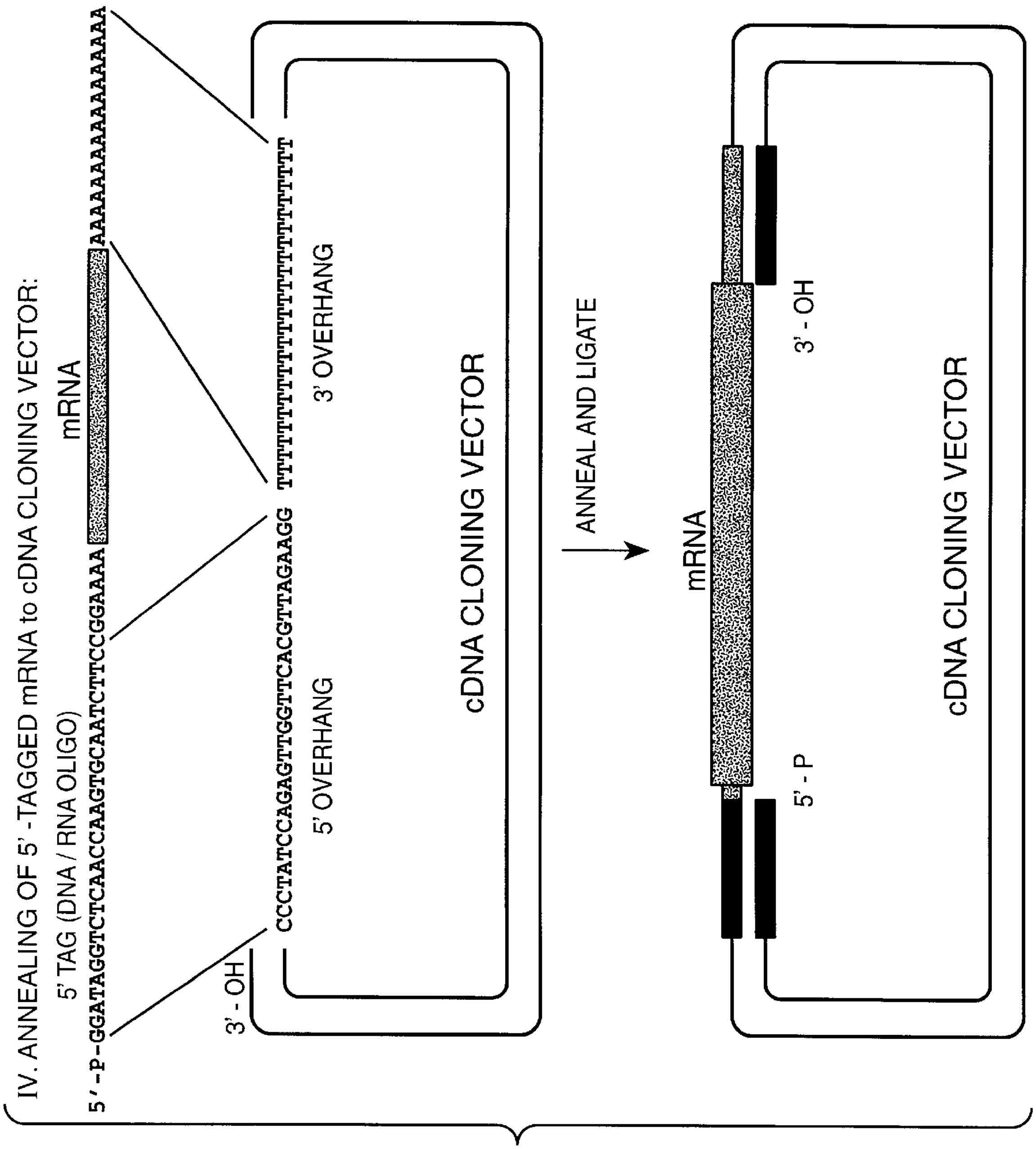
FIG._4

V. CONVERSION OF mRNA INTO dscDNA:
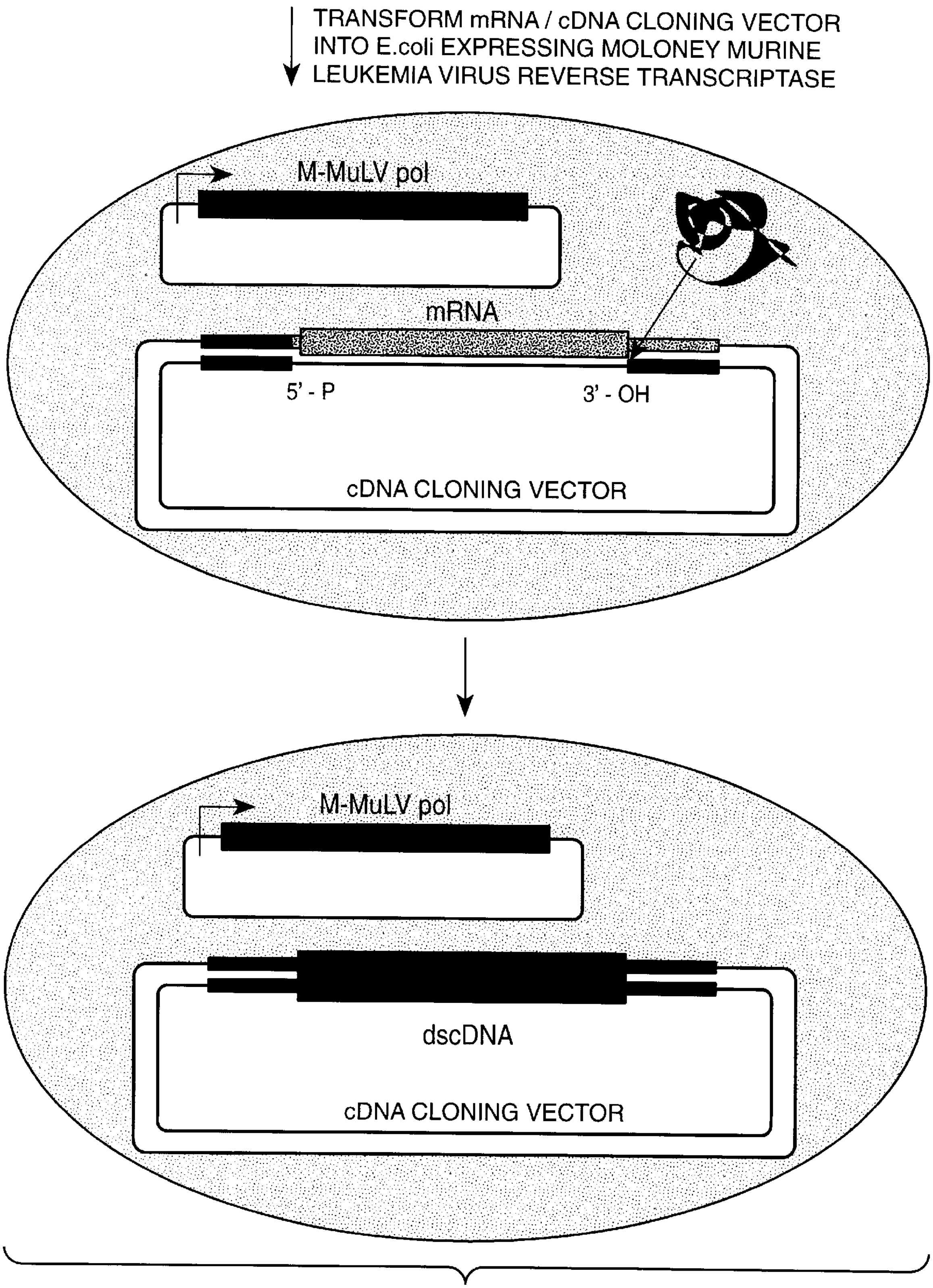
FIG._5

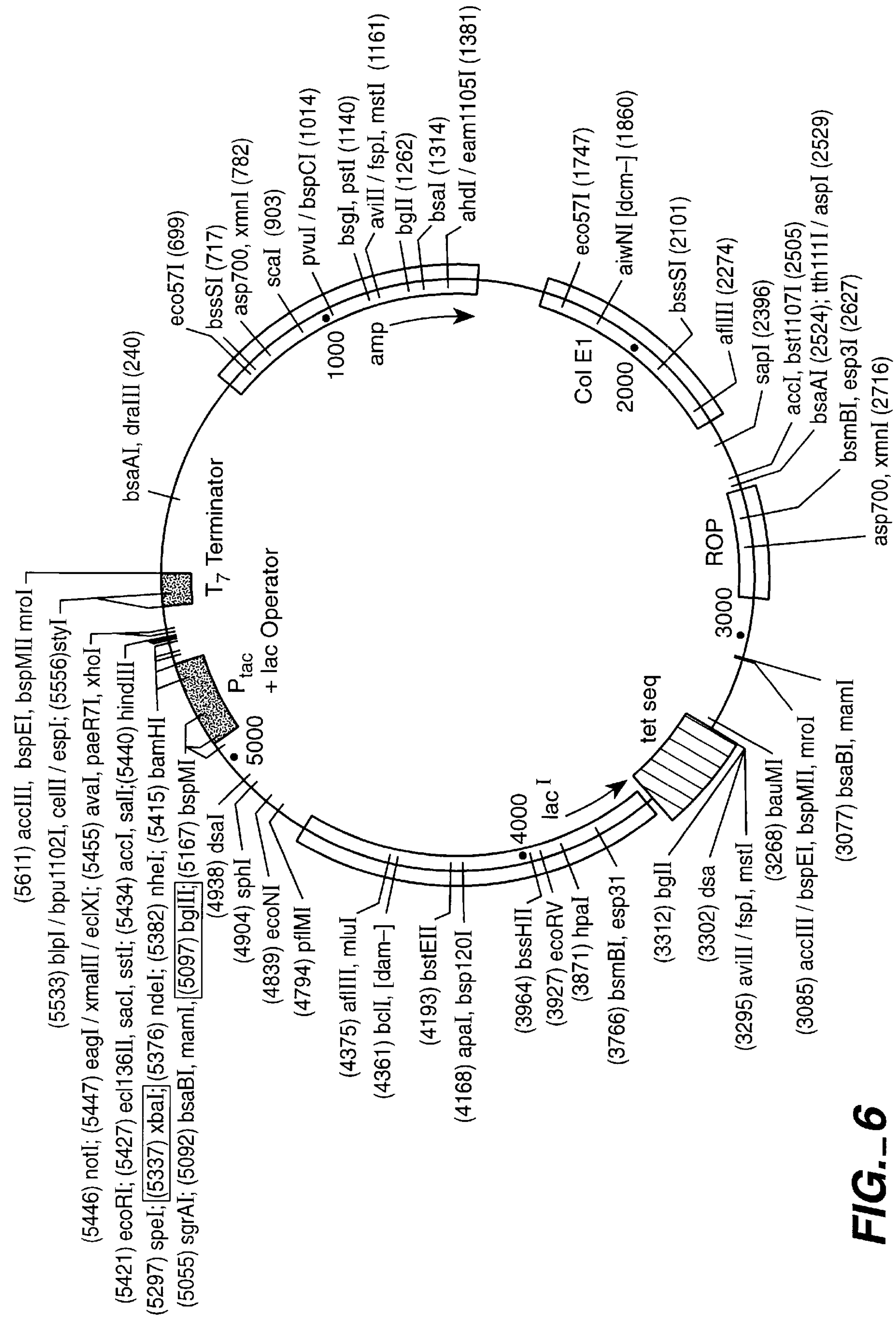
FIG._6

TGGCGAATGG GACGCGCCCT GTAGCGGCGC ATTAAGCGCG GCGGGTGTGG 50
TGGTTACGCG CAGCGTGACC GCTACACTTG CCAGCGCCCT AGCGCCCGCT 100
CCTTTCGCTT TCTTCCCTTC CTTTCTCGCC ACGTTCGCCG GCTTTCCCCG 150
TCAAGCTCTA AATCGGGGGC TCCCTTTAGG GTTCCGATTT AGTGCTTTAC 200
GGCACCTCGA CCCCAAAAAA CTTGATTAGG GTGATGGTTC ACGTAGTGGG 250
CCATCGCCCT GATAGACGGT TTTTCGCCCT TTGACGTTGG AGTCCACGTT 300
CTTTAATAGT GGACTCTTGT TCCAAACTGG AACAACACTC AACCCTATCT 350
CGGTCTATTC TTTTGATTTA TAAGGGATTT TGCCGATTTC GGCCTATTGG 400
TTAAAAAATG AGCTGATTTA ACAAAAATTT AACGCGAATT TTAACAAAAT 450
ATTAACGTTT ACAATTTCAG GTGGCACTTT TCGGGGAAAT GTGCGCGGAA 500
CCCCTATTTG TTTATTTTTC TAAATACATT CAAATATGTA TCCGCTCATG 550
AGACAATAAC CCTGATAAAT GCTTCAATAA TATTGAAAAA GGAAGAGTAT 600
GAGTATTCAA CATTTCCGTG TCGCCCTTAT TCCCTTTTTT GCGGCATTTT 650
GCCTTCCTGT TTTTGCTCAC CCAGAAACGC TGGTGAAAGT AAAAGATGCT 700
GAAGATCAGT TGGGTGCACG AGTGGGTTAC ATCGAACTGG ATCTCAACAG 750
CGGTAAGATC CTTGAGAGTT TTCGCCCCGA AGAACGTTTT CCAATGATGA 800
GCACTTTTAA AGTTCTGCTA TGTGGCGCGG TATTATCCCG TATTGACGCC 850
GGGCAAGAGC AACTCGGTCG CCGCATACAC TATTCTCAGA ATGACTTGGT 900
TGAGTACTCA CCAGTCACAG AAAAGCATCT TACGGATGGC ATGACAGTAA 950
GAGAATTATG CAGTGCTGCC ATAACCATGA GTGATAACAC TGCGGCCAAC 1000
TTACTTCTGA CAACGATCGG AGGACCGAAG GAGCTAACCG CTTTTTTGCA 1050
CAACATGGGG GATCATGTAA CTCGCCTTGA TCGTTGGGAA CCGGAGCTGA 1100
ATGAAGCCAT ACCAAACGAC GAGCGTGACA CCACGATGCC TGCAGCAATG 1150
GCAACAACGT TGCGCAAACT ATTAACTGGC GAACTACTTA CTCTAGCTTC 1200
CCGGCAACAA TTAATAGACT GGATGGAGGC GGATAAAGTT GCAGGACCAC 1250
TTCTGCGCTC GGCCCTTCCG GCTGGCTGGT TTATTGCTGA TAAATCTGGA 1300

FIG._7A

GCCGGTGAGC GTGGGTCTCG CGGTATCATT GCAGCACTGG GGCCAGATGG 1350
TAAGCCCTCC CGTATCGTAG TTATCTACAC GACGGGGAGT CAGGCAACTA 1400
TGGATGAACG AAATAGACAG ATCGCTGAGA TAGGTGCCTC ACTGATTAAG 1450
CATTGGTAAC TGTCAGACCA AGTTTACTCA TATATACTTT AGATTGATTT 1500
AAAACTTCAT TTTTAATTTA AAAGGATCTA GGTGAAGATC CTTTTTGATA 1550
ATCTCATGAC CAAAATCCCT TAACGTGAGT TTTCGTTCCA CTGAGCGTCA 1600
GACCCCGTAG AAAAGATCAA AGGATCTTCT TGAGATCCTT TTTTTCTGCG 1650
CGTAATCTGC TGCTTGCAAA CAAAAAAACC ACCGCTACCA GCGGTGGTTT 1700
GTTTGCCGGA TCAAGAGCTA CCAACTCTTT TTCCGAAGGT AACTGGCTTC 1750
AGCAGAGCGC AGATACCAAA TACTGTCCTT CTAGTGTAGC CGTAGTTAGG 1800
CCACCACTTC AAGAACTCTG TAGCACCGCC TACATACCTC GCTCTGCTAA 1850
TCCTGTTACC AGTGGCTGCT GCCAGTGGCG ATAAGTCGTG TCTTACCGGG 1900
TTGGACTCAA GACGATAGTT ACCGGATAAG GCGCAGCGGT CGGGCTGAAC 1950
GGGGGGTTCG TGCACACAGC CCAGCTTGGA GCGAACGACC TACACCGAAC 2000
TGAGATACCT ACAGCGTGAG CTATGAGAAA GCGCCACGCT TCCCGAAGGG 2050
AGAAAGGCGG ACAGGTATCC GGTAAGCGGC AGGGTCGGAA CAGGAGAGCG 2100
CACGAGGGAG CTTCCAGGGG GAAACGCCTG GTATCTTTAT AGTCCTGTCG 2150
GGTTTCGCCA CCTCTGACTT GAGCGTCGAT TTTTGTGATG CTCGTCAGGG 2200
GGGCGGAGCC TATGGAAAAA CGCCAGCAAC GCGGCCTTTT TACGGTTCCT 2250
GGCCTTTTGC TGGCCTTTTG CTCACATGTT CTTTCCTGCG TTATCCCCTG 2300
ATTCTGTGGA TAACCGTATT ACCGCCTTTG AGTGAGCTGA TACCGCTCGC 2350
CGCAGCCGAA CGACCGAGCG CAGCGAGTCA GTGAGCGAGG AAGCGGAAGA 2400
GCGCCTGATG CGGTATTTTC TCCTTACGCA TCTGTGCGGT ATTTCACACC 2450
GCATATATGG TGCACTCTCA GTACAATCTG CTCTGATGCC GCATAGTTAA 2500
GCCAGTATAC ACTCCGCTAT CGCTACGTGA CTGGGTCATG GCTGCGCCCC 2550
GACACCCGCC AACACCCGCT GACGCGCCCT GACGGGCTTG TCTGCTCCCG 2600

FIG._7B

GCATCCGCTT ACAGACAAGC TGTGACCGTC TCCGGGAGCT GCATGTGTCA 2650
GAGGTTTTCA CCGTCATCAC CGAAACGCGC GAGGCAGCTG CGGTAAAGCT 2700
CATCAGCGTG GTCGTGAAGC GATTCACAGA TGTCTGCCTG TTCATCCGCG 2750
TCCAGCTCGT TGAGTTTCTC CAGAAGCGTT AATGTCTGGC TTCTGATAAA 2800
GCGGGCCATG TTAAGGGCGG TTTTTTCCTG TTTGGTCACT GATGCCTCCG 2850
TGTAAGGGGG ATTTCTGTTC ATGGGGGTAA TGATACCGAT GAAACGAGAG 2900
AGGATGCTCA CGATACGGGT TACTGATGAT GAACATGCCC GGTTACTGGA 2950
ACGTTGTGAG GGTAAACAAC TGGCGGTATG GATGCGGCGG GACCAGAGAA 3000
AAATCACTCA GGGTCAATGC CAGCGCTTCG TTAATACAGA TGTAGGTGTT 3050
CCACAGGGTA GCCAGCAGCA TCCTGCGATG CAGATCCGGA ACATAATGGT 3100
GCAGGGCGCT GACTTCCGCG TTTCCAGACT TTACGAAACA CGGAAACCGA 3150
AGACCATTCA TGTTGTTGCT CAGGTCGCAG ACGTTTTGCA GCAGCAGTCG 3200
CTTCACGTTC GCTCGCGTAT CGGTGATTCA TTCTGCTAAC CAGTAAGGCA 3250
ACCCCGCCAG CCTAGCCGGG TCCTCAACGA CAGGAGCACG ATCATGCGCA 3300
CCCGTGGGGC CGCCATGCCG GCGATAATGG CCTGCTTCTC GCCGAAACGT 3350
TTGGTGGCGG GACCAGTGAC GAAGGCTTGA GCGAGGGCGT GCAAGATTCC 3400
GAATACCGCA AGCGACAGGC CGATCATCGT CGCGCTCCAG CGAAAGCGGT 3450
CCTCGCCGAA AATGACCCAG AGCGCTGCCG GCACCTGTCC TACGAGTTGC 3500
ATGATAAAGA AGACAGTCAT AAGTGCGGCG ACGATAGTCA TGCCCCGCGC 3550
CCACCGGAAG GAGCTGACTG GGTTGAAGGC TCTCAAGGGC ATCGGTCGAG 3600
ATCCCGGTGC CTAATGAGTG AGCTAACTTA CATTAATTGC GTTGCGCTCA 3650
CTGCCCGCTT TCCAGTCGGG AAACCTGTCG TGCCAGCTGC ATTAATGAAT 3700
CGGCCAACGC GCGGGGAGAG GCGGTTTGCG TATTGGGCGC CAGGGTGGTT 3750
TTTCTTTTCA CCAGTGAGAC GGGCAACAGC TGATTGCCCT TCACCGCCTG 3800
GCCCTGAGAG AGTTGCAGCA AGCGGTCCAC GCTGGTTTGC CCCAGCAGGC 3850
GAAAATCCTG TTTGATGGTG GTTAACGGCG GGATATAACA TGAGCTGTCT 3900

FIG._7C

TCGGTATCGT CGTATCCCAC TACCGAGATA TCCGCACCAA CGCGCAGCCC 3950
GGACTCGGTA ATGGCGCGCA TTGCGCCCAG CGCCATCTGA TCGTTGGCAA 4000
CCAGCATCGC AGTGGGAACG ATGCCCTCAT TCAGCATTTG CATGGTTTGT 4050
TGAAAACCGG ACATGGCACT CCAGTCGCCT TCCCGTTCCG CTATCGGCTG 4100
AATTTGATTG CGAGTGAGAT ATTTATGCCA GCCAGCCAGA CGCAGACGCG 4150
CCGAGACAGA ACTTAATGGG CCCGCTAACA GCGCGATTTG CTGGTGACCC 4200
AATGCGACCA GATGCTCCAC GCCCAGTCGC GTACCGTCTT CATGGGAGAA 4250
AATAATACTG TTGATGGGTG TCTGGTCAGA GACATCAAGA AATAACGCCG 4300
GAACATTAGT GCAGGCAGCT TCCACAGCAA TGGCATCCTG GTCATCCAGC 4350
GGATAGTTAA TGATCAGCCC ACTGACGCGT TGCGCGAGAA GATTGTGCAC 4400
CGCCGCTTTA CAGGCTTCGA CGCCGCTTCG TTCTACCATC GACACCACCA 4450
CGCTGGCACC CAGTTGATCG GCGCGAGATT TAATCGCCGC GACAATTTGC 4500
GACGGCGCGT GCAGGGCCAG ACTGGAGGTG GCAACGCCAA TCAGCAACGA 4550
CTGTTTGCCC GCCAGTTGTT GTGCCACGCG GTTGGGAATG TAATTCAGCT 4600
CCGCCATCGC CGCTTCCACT TTTTCCCGCG TTTTCGCAGA AACGTGGCTG 4650
GCCTGGTTCA CCACGCGGGA AACGGTCTGA TAAGAGACAC CGGCATACTC 4700
TGCGACATCG TATAACGTTA CTGGTTTCAC ATTCACCACC CTGAATTGAC 4750
TCTCTTCCGG GCGCTATCAT GCCATACCGC GAAAGGTTTT GCGCCATTCG 4800
ATGGTGTCCG GGATCTCGAC GCTCTCCCTT ATGCGACTCC TGCATTAGGA 4850
AGCAGCCCAG TAGTAGGTTG AGGCCGTTGA GCACCGCCGC CGCAAGGAAT 4900
GGTGCATGCA AGGAGATGGC GCCCAACAGT CCCCCGGCCA CGGGGCCTGC 4950
CACCATACCC ACGCCGAAAC AAGCGCTCAT GAGCCCGAAG TGGCGAGCCC 5000
GATCTTCCCC ATCGGTGATG TCGGCGATAT AGGCGCCAGC AACCGCACCT 5050
GTGGCGCCGG TGATGCCGGC CACGATGCGT CCGGCGTAGA GGATCGAGAT 5100
CTCGACTGCA CGGGCACAAT GCTTCTGGCG TCAGGCAGCC ATCGGAAGCT 5150
GTGGTATGGC TGTGCAGGTC GTAAATCACT GCATAATTCG TGTCGCTCAA 5200

FIG._7D

```
GGCGCACTCC CGTTCTGGAT AATGTTTTTT GCGCCGACAT CATAACGGTT 5250
CTGGCAAATA TTCTGAAATG AGCTGTTGAC AATTAATCAT CGAACTAGTT 5300
TAATGTGTGG AATTGTGAGC GGATAACAAT TCCCCTCTAG AAATAATTTT 5350
GTTTAACTTT AAGAAGGAGA TATACATATG GCTAGCATGA CTGGTGGACA 5400
GCAAATGGGT CGCGGATCCG AATTCGAGCT CCGTCGACAA GCTTGCGGCC 5450
GCACTCGAGC ACCACCACCA CCACCACTGA GATCCGGCTG CTAACAAAGC 5500
CCGAAAGGAA GCTGAGTTGG CTGCTGCCAC CGCTGAGCAA TAACTAGCAT 5550
AACCCCTTGG GGCCTCTAAA CGGGTCTTGA GGGGTTTTTT GCTGAAAGGA 5600
GGAACTATAT CCGGAT 5616
```

FIG._7E

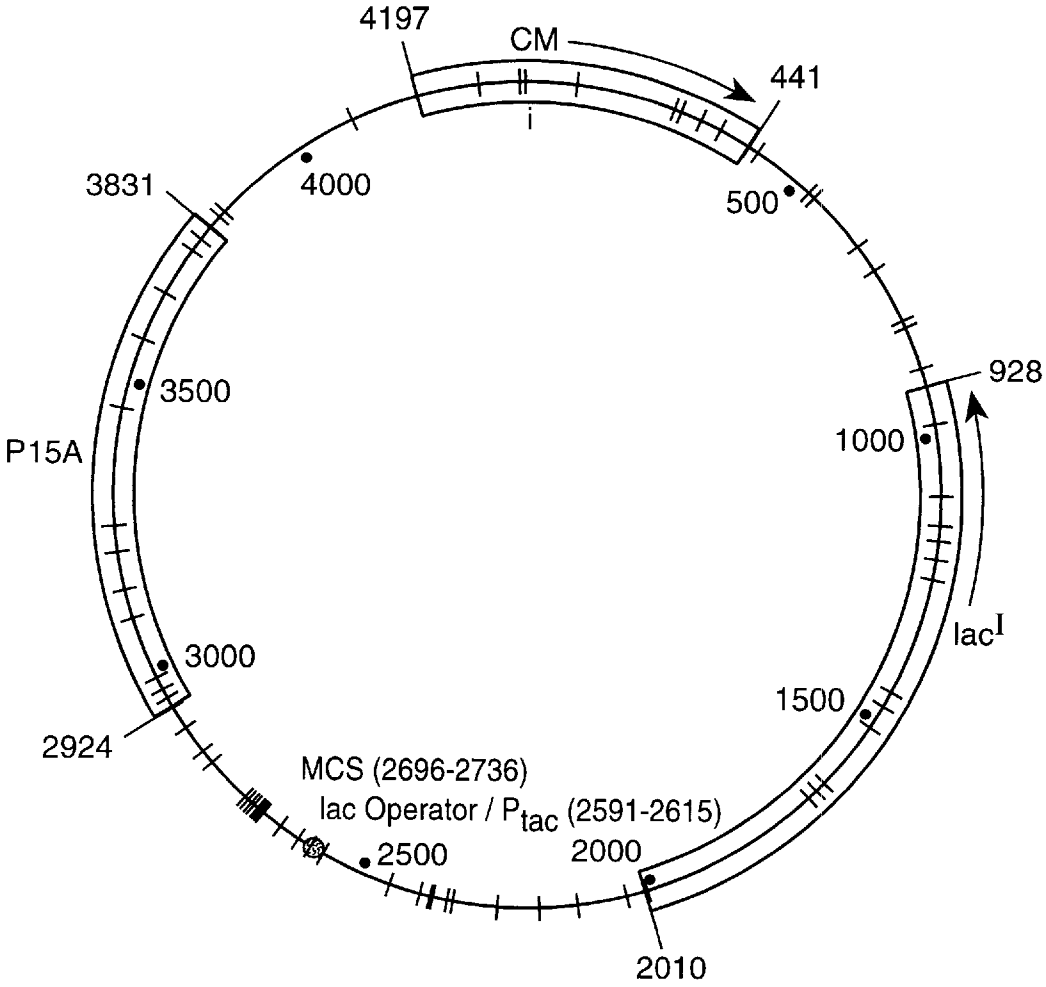
FIG._8

GAATTCCGGA TGAGCATTCA TCAGGCGGGC AAGAATGTGA ATAAAGGCCG 50
GATAAAACTT GTGCTTATTT TTCTTTACGG TCTTTAAAAA GGCCGTAATA 100
TCCAGCTGAA CGGTCTGGTT ATAGGTACAT TGAGCAACTG ACTGAAATGC 150
CTCAAAATGT TCTTTACGAT GCCATTGGGA TATATCAACG GTGGTATATC 200
CAGTGATTTT TTTCTCCATT TTAGCTTCCT TAGCTCCTGA AAATCTCGAT 250
AACTCAAAAA ATACGCCCGG TAGTGATCTT ATTTCATTAT GGTGAAAGTT 300
GGAACCTCTT ACGTGCCGAT CAACGTCTCA TTTTCGCCAA AAGTTGGCCC 350
AGGGCTTCCC GGTATCAACA GGGACACCAG GATTTATTTA TTCTGCGAAG 400
TGATCTTCCG TCACAGGTAT TTATTCGGCG CAAAGTGCGT CGGGTGATGC 450
TGCCAACTTA CTGATTTAGT GTATGATGGT GTTTTTGAGG TGCTCCAGTG 500
GCTTCTGTTT CTATCAGCTG TCCCTCCTGT TCAGCTACTG ACGGGGTGGT 550
GCGTAACGGC AAAAGCACCG CCGGACATCA GCGCTAGCGG AGTGTATACT 600
GGCTTACTAT GTTGGCACTG ATGAGGGTGT CAGTGAAGTG CTTCATGTGG 650
CAGGAGAAAA AAGGCTGCAC CGGTGCGTCA GCAGAATATG TGATACAGGA 700
TATATTCCGC TTCCTCGCTC ACTGACTCGC TACGCTCGGT CGTTCGACTG 750
CGGCGAGCGG AAATGGCTTA CGAACGGGGC GGAGATTTCC TGGAAGATGC 800
CAGGAAGATA CTTAACAGGG AAGTGAGAGG GCCGCGGCAA AGCCGTTTTT 850
CCATAGGCTC CGCCCCCCTG ACAAGCATCA CGAAATCTGA CGCTCAAATC 900
AGTGGTGGCG AAACCCGACA GGACTATAAA GATACCAGGC GTTTCCCCCT 950
GGCGGCTCCC TCGTGCGCTC TCCTGTTCCT GCCTTTCGGT TTACCGGTGT 1000
CATTCCGCTG TTATGGCCGC GTTTGTCTCA TTCCACGCCT GACACTCAGT 1050
TCCGGGTAGG CAGTTCGCTC CAAGCTGGAC TGTATGCACG AACCCCCCGT 1100
TCAGTCCGAC CGCTGCGCCT TATCCGGTAA CTATCGTCTT GAGTCCAACC 1150
CGGAAAGACA TGCAAAAGCA CCACTGGCAG CAGCCACTGG TAATTGATTT 1200
AGAGGAGTTA GTCTTGAAGT CATGCGCCGG TTAAGGCTAA ACTGAAAGGA 1250
CAAGTTTTGG TGACTGCGCT CCTCCAAGCC AGTTACCTCG GTTCAAAGAG 1300

FIG._9A

TTGGTAGCTC AGAGAACCTT CGAAAAACCG CCCTGCAAGG CGGTTTTTTC 1350
GTTTTCAGAG CAAGAGATTA CGCGCAGACC AAAACGATCT CAAGAAGATC 1400
ATCTTATTAA TCAGATAAAA TATTTCTAGA TTTCAGTGCA ATTTATCTCT 1450
TCAAATGTAG CACCTGAAGT CAGCCCCATA CGATATAAGT TGTAATTCTC 1500
ATGTTTGACA GCTTATCATC GATATAGTTC CTCCTTTCAG CAAAAAACCC 1550
CTCAAGACCC GTTTAGAGGC CCCAAGGGGT TATGCTAGTT ATTGCTCAGC 1600
GGTGGCAGCA GCCAACTCAG CTTCCTTTCG GGCTTTGTTA GCAGCCGGAT 1650
CTCAGTGGTG GTGGTGGTGG TGCTCGAGTG CGGCCGCAAG CTTGTCGACG 1700
GAGCTCGAAT TCGGATCCGC GACCCATTTG CTGTCCACCA GTCATGCTAG 1750
CCATATGTAT ATCTCCTTCT TAAAGTTAAA CAAAATTATT TCTAGAGGGG 1800
AATTGTTATC CGCTCACAAT TCCACACATT AAACTAGTTC GATGATTAAT 1850
TGTCAACAGC TCATTTCAGA ATATTTGCCA GAACCGTTAT GATGTCGGCG 1900
CAAAAAACAT TATCCAGAAC GGGAGTGCGC CTTGAGCGAC ACGAATTATG 1950
CAGTGATTTA CGACCTGCAC AGCCATACCA CAGCTTCCGA TGGCTGCCTG 2000
ACGCCAGAAG CATTGTGCCC GTGCAGTCGA GATCTCGATC CTCTACGCCG 2050
GACGCATCGT GGCCGGCATC ACCGGCGCCA CAGGTGCGGT TGCTGGCGCC 2100
TATATCGCCG ACATCACCGA TGGGGAAGAT CGGGCTCGCC ACTTCGGGCT 2150
CATGAGCGCT TGTTTCGGCG TGGGTATGGT GGCAGGCCCC GTGGCCGGGG 2200
GACTGTTGGG CGCCATCTCC TTGCATGCAC CATTCCTTGC GGCGGCGGTG 2250
CTCAACGGCC TCAACCTACT ACTGGGCTGC TTCCTAATGC AGGAGTCGCA 2300
TAAGGGAGAG CGTCGAGATC CCGGACACCA TCGAATGGCG CAAAACCTTT 2350
CGCGGTATGG CATGATAGCG CCCGGAAGAG AGTCAATTCA GGGTGGTGAA 2400
TGTGAAACCA GTAACGTTAT ACGATGTCGC AGAGTATGCC GGTGTCTCTT 2450
ATCAGACCGT TTCCCGCGTG GTGAACCAGG CCAGCCACGT TTCTGCGAAA 2500
ACGCGGGAAA AAGTGGAAGC GGCGATGGCG GAGCTGAATT ACATTCCCAA 2550
CCGCGTGGCA CAACAACTGG CGGGCAAACA GTCGTTGCTG ATTGGCGTTG 2600

FIG._9B

CCACCTCCAG TCTGGCCCTG CACGCGCCGT CGCAAATTGT CGCGGCGATT 2650
AAATCTCGCG CCGATCAACT GGGTGCCAGC GTGGTGGTGT CGATGGTAGA 2700
ACGAAGCGGC GTCGAAGCCT GTAAAGCGGC GGTGCACAAT CTTCTCGCGC 2750
AACGCGTCAG TGGGCTGATC ATTAACTATC CGCTGGATGA CCAGGATGCC 2800
ATTGCTGTGG AAGCTGCCTG CACTAATGTT CCGGCGTTAT TTCTTGATGT 2850
CTCTGACCAG ACACCCATCA ACAGTATTAT TTTCTCCCAT GAAGACGGTA 2900
CGCGACTGGG CGTGGAGCAT CTGGTCGCAT TGGGTCACCA GCAAATCGCG 2950
CTGTTAGCGG GCCCATTAAG TTCTGTCTCG GCGCGTCTGC GTCTGGCTGG 3000
CTGGCATAAA TATCTCACTC GCAATCAAAT TCAGCCGATA GCGGAACGGG 3050
AAGGCGACTG GAGTGCCATG TCCGGTTTTC AACAAACCAT GCAAATGCTG 3100
AATGAGGGCA TCGTTCCCAC TGCGATGCTG GTTGCCAACG ATCAGATGGC 3150
GCTGGGCGCA ATGCGCGCCA TTACCGAGTC CGGGCTGCGC GTTGGTGCGG 3200
ATATCTCGGT AGTGGGATAC GACGATACCG AAGACAGCTC ATGTTATATC 3250
CCGCCGTTAA CCACCATCAA ACAGGATTTT CGCCTGCTGG GGCAAACCAG 3300
CGTGGACCGC TTGCTGCAAC TCTCTCAGGG CCAGGCGGTG AAGGGCAATC 3350
AGCTGTTGCC CGTCTCACTG GTGAAAAGAA AAACCACCCT GGCGCCCAAT 3400
ACGCAAACCG CCTCTCCCCG CGCGTTGGCC GATTCATTAA TGCAGCTGGC 3450
ACGACAGGTT TCCCGACTGG AAAGCGGGCA GTGAGCGCAA CGCAATTAAT 3500
GTAAGTTAGC TCACTCATTA GGCCCCGGCA GCGCCCAACA GTCCCCCGGC 3550
CACGGGGCCT GCCACCATAC CCACGCCGAA ACAAGCGCCC TGCACCATTA 3600
TGTTCCGGAT CTGCATCGCA GGATGCTGCT GGCTACCCTG TGGAACACCT 3650
ACATCTGTAT TAACGAAGCG CTAACCGTTT TTATCAGGCT CTGGGAGGCA 3700
GAATAAATGA TCATATCGTC AATTATTACC TCCACGGGGA GAGCCTGAGC 3750
AAACTGGCCT CAGGCATTTG AGAAGCACAC GGTCACACTG CTTCCGGTAG 3800
TCAATAAACC GGTAAACCAG CAATAGACAT AAGCGGCTAT TTAACGACCC 3850
TGCCCTGAAC CGACGACCGG GTCGAATTTG CTTTCGAATT TCTGCCATTC 3900

FIG._9C

ATCCGCTTAT TATCACTTAT TCAGGCGTAG CACCAGGCGT TTAAGGGCAC 3950

CAATAACTGC CTTAAAAAAA TTACGCCCCG CCCTGCCACT CATCGCAGTA 4000

CTGTTGTAAT TCATTAAGCA TTCTGCCGAC ATGGAAGCCA TCACAGACGG 4050

CATGATGAAC CTGAATCGCC AGCGGCATCA GCACCTTGTC GCCTTGCGTA 4100

TAATATTTGC CCATGGTGAA AACGGGGGCG AAGAAGTTGT CCATATTGGC 4150

CACGTTTAAA TCAAAACTGG TGAAACTCAC CCAGGGATTG GCTGAGACGA 4200

AAAACATATT CTCAATAAAC CCTTTAGGGA AATAGGCCAG GTTTTCACCG 4250

TAACACGCCA CATCTTGCGA ATATATGTGT AGAAACTGCC GGAAATCGTC 4300

GTGGTATTCA CTCCAGAGCG ATGAAAACGT TTCAGTTTGC TCATGGAAAA 4350

CGGTGTAACA AGGGTGAACA CTATCCCATA TCACCAGCTC ACCGTCTTTC 4400

ATTGCCATAC G 4411

FIG._9D

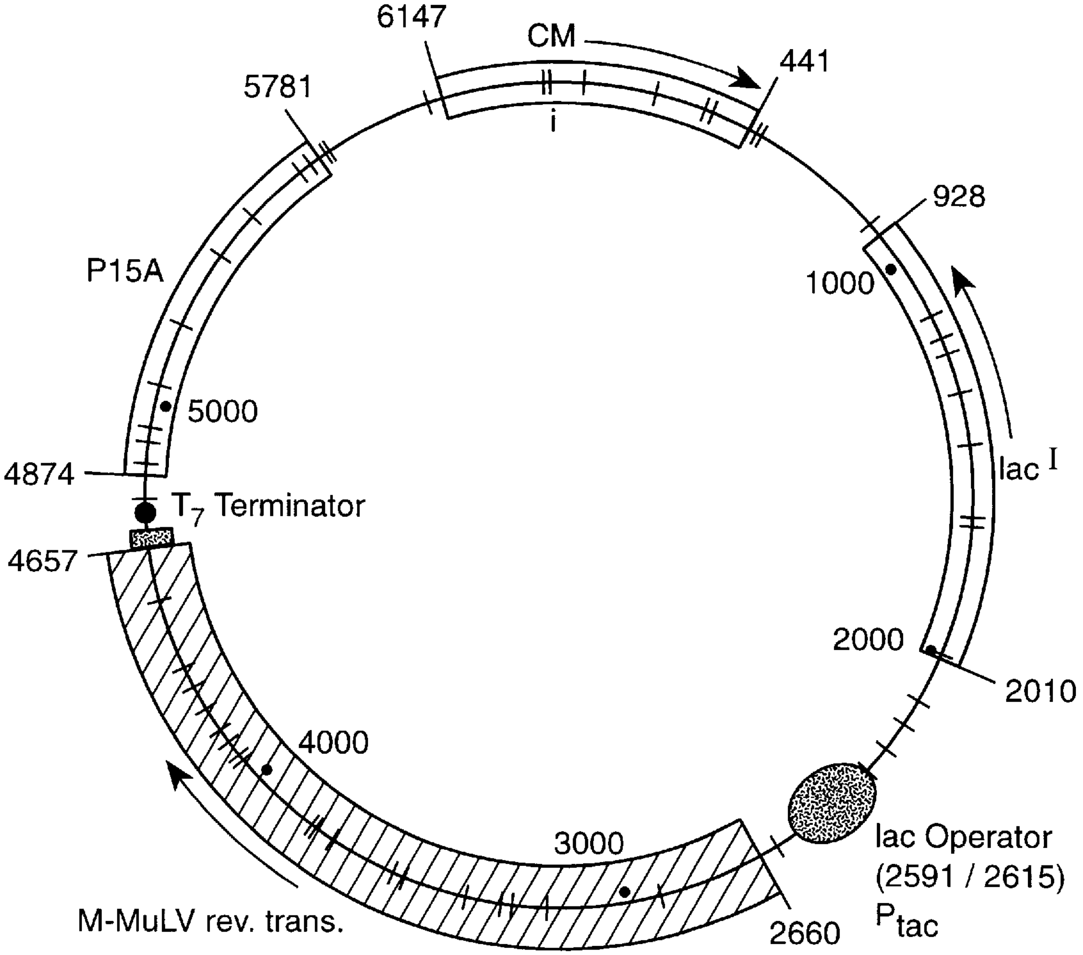
FIG._10

CGTATGGCAA TGAAAGACGG TGAGCTGGTG ATATGGGATA GTGTTCACCC 50

TTGTTACACC GTTTTCCATG AGCAAACTGA AACGTTTTCA TCGCTCTGGA 100

GTGAATACCA CGACGATTTC CGGCAGTTTC TACACATATA TTCGCAAGAT 150

GTGGCGTGTT ACGGTGAAAA CCTGGCCTAT TTCCCTAAAG GGTTTATTGA 200

GAATATGTTT TTCGTCTCAG CCAATCCCTG GGTGAGTTTC ACCAGTTTTG 250

ATTTAAACGT GGCCAATATG GACAACTTCT TCGCCCCCGT TTTCACCATG 300

GGCAAATATT ATACGCAAGG CGACAAGGTG CTGATGCCGC TGGCGATTCA 350

GGTTCATCAT GCCGTCTGTG ATGGCTTCCA TGTCGGCAGA ATGCTTAATG 400

AATTACAACA GTACTGCGAT GAGTGGCAGG GCGGGGCGTA ATTTTTTTAA 450

GGCAGTTATT GGTGCCCTTA AACGCCTGGT GCTACGCCTG AATAAGTGAT 500

AATAAGCGGA TGAATGGCAG AAATTCGAAA GCAAATTCGA CCCGGTCGTC 550

GGTTCAGGGC AGGGTCGTTA AATAGCCGCT TATGTCTATT GCTGGTTTAC 600

CGGTTTATTG ACTACCGGAA GCAGTGTGAC CGTGTGCTTC TCAAATGCCT 650

GAGGCCAGTT TGCTCAGGCT CTCCCCGTGG AGGTAATAAT TGACGATATG 700

ATCATTTATT CTGCCTCCCA GAGCCTGATA AAAACGGTTA GCGCTTCGTT 750

AATACAGATG TAGGTGTTCC ACAGGGTAGC CAGCAGCATC CTGCGATGCA 800

GATCCGGAAC ATAATGGTGC AGGGCGCTTG TTTCGGCGTG GGTATGGTGG 850

CAGGCCCCGT GGCCGGGGGA CTGTTGGGCG CTGCCGGGGC CTAATGAGTG 900

AGCTAACTTA CATTAATTGC GTTGCGCTCA CTGCCCGCTT TCCAGTCGGG 950

AAACCTGTCG TGCCAGCTGC ATTAATGAAT CGGCCAACGC GCGGGGAGAG 1000

GCGGTTTGCG TATTGGGCGC CAGGGTGGTT TTTCTTTTCA CCAGTGAGAC 1050

GGGCAACAGC TGATTGCCCT TCACCGCCTG GCCCTGAGAG AGTTGCAGCA 1100

AGCGGTCCAC GCTGGTTTGC CCCAGCAGGC GAAAATCCTG TTTGATGGTG 1150

GTTAACGGCG GGATATAACA TGAGCTGTCT TCGGTATCGT CGTATCCCAC 1200

TACCGAGATA TCCGCACCAA CGCGCAGCCC GGACTCGGTA ATGGCGCGCA 1250

TTGCGCCCAG CGCCATCTGA TCGTTGGCAA CCAGCATCGC AGTGGGAACG 1300

FIG._11A

ATGCCCTCAT TCAGCATTTG CATGGTTTGT TGAAAACCGG ACATGGCACT 1350

CCAGTCGCCT TCCCGTTCCG CTATCGGCTG AATTTGATTG CGAGTGAGAT 1400

ATTTATGCCA GCCAGCCAGA CGCAGACGCG CCGAGACAGA ACTTAATGGG 1450

CCCGCTAACA GCGCGATTTG CTGGTGACCC AATGCGACCA GATGCTCCAC 1500

GCCCAGTCGC GTACCGTCTT CATGGGAGAA AATAATACTG TTGATGGGTG 1550

TCTGGTCAGA GACATCAAGA AATAACGCCG GAACATTAGT GCAGGCAGCT 1600

TCCACAGCAA TGGCATCCTG GTCATCCAGC GGATAGTTAA TGATCAGCCC 1650

ACTGACGCGT TGCGCGAGAA GATTGTGCAC CGCCGCTTTA CAGGCTTCGA 1700

CGCCGCTTCG TTCTACCATC GACACCACCA CGCTGGCACC CAGTTGATCG 1750

GCGCGAGATT TAATCGCCGC GACAATTTGC GACGGCGCGT GCAGGGCCAG 1800

ACTGGAGGTG GCAACGCCAA TCAGCAACGA CTGTTTGCCC GCCAGTTGTT 1850

GTGCCACGCG GTTGGGAATG TAATTCAGCT CCGCCATCGC CGCTTCCACT 1900

TTTTCCCGCG TTTTCGCAGA AACGTGGCTG GCCTGGTTCA CCACGCGGGA 1950

AACGGTCTGA TAAGAGACAC CGGCATACTC TGCGACATCG TATAACGTTA 2000

CTGGTTTCAC ATTCACCACC CTGAATTGAC TCTCTTCCGG GCGCTATCAT 2050

GCCATACCGC GAAAGGTTTT GCGCCATTCG ATGGTGTCCG GGATCTCGAC 2100

GCTCTCCCTT ATGCGACTCC TGCATTAGGA AGCAGCCCAG TAGTAGGTTG 2150

AGGCCGTTGA GCACCGCCGC CGCAAGGAAT GGTGCATGCA AGGAGATGGC 2200

GCCCAACAGT CCCCCGGCCA CGGGGCCTGC CACCATACCC ACGCCGAAAC 2250

AAGCGCTCAT GAGCCCGAAG TGGCGAGCCC GATCTTCCCC ATCGGTGATG 2300

TCGGCGATAT AGGCGCCAGC AACCGCACCT GTGGCGCCGG TGATGCCGGC 2350

CACGATGCGT CCGGCGTAGA GGATCGAGAT CTCGACTGCA CGGGCACAAT 2400

GCTTCTGGCG TCAGGCAGCC ATCGGAAGCT GTGGTATGGC TGTGCAGGTC 2450

GTAAATCACT GCATAATTCG TGTCGCTCAA GGCGCACTCC CGTTCTGGAT 2500

AATGTTTTTT GCGCCGACAT CATAACGGTT CTGGCAAATA TTCTGAAATG 2550

AGCTGTTGAC AATTAATCAT CGAACTAGTT TAATGTGTGG AATTGTGAGC 2600

*FIG._11B*

GGATAACAAT TCCCCTCTAG AAATAATTTT GTTTAACTTT AAGAAGGAGA 2650
TATACATATG CCTTTGAATA TCGAAGATGA GCATCGTCTG CATGAGACCT 2700
CAAAAGAGCC GGATGTTTCT CTAGGGTCCA CATGGCTTTC TGCTTTCCCC 2750
CAGGCCTGGG CAGAAACCGG GGGCATGGGA CTGGCAGTTC GCCAAGCTCC 2800
TCTGATCATA CCTCTGAAGG CAACCTCTAC CCCCGTGTCC ATAAAACAAT 2850
ACCCCATGTC ACAAGAAGCC AGACTGGGGA TCAAGCCCCA CATACAGAGA 2900
CTGTTGGACC AGGGAATACT GGTACCCTGC CAGTCCCCCT GGAACACGCC 2950
CCTGCTACCC ATTAAGAAAC CAGGGACTAA TGATTACAGG CCTGTCCAAG 3000
ATCTGAGAGA AGTCAACAAG CGGGTGGAAG ACATCCACCC CACCGTGCCC 3050
AACCCTTACA ACCTCTTGAG TGGGCTCCCA CCGTCCCACC AGTGGTACAC 3100
TGTGCTTGAC TTAAAGGATG CCTTTTTCTG CCTGAGACTC CACCCCACCA 3150
GTCAGCCTCT CTTCGCCTTT GAGTGGAGAG ACCCAGAGAT GGGAATCTCA 3200
GGACAATTAA CCTGGACCAG ACTCCCACAG GGTTTCAAAA ACAGTCCCAC 3250
CCTGTTTGAT GAGGCACTGC ACAGAGACCT AGCAGGCTTC CGGATCCAGC 3300
ACCCAGACTT GATCCTGCTA CAGTACGTGG ATGACTTACT GCTGGCCGCC 3350
TCTTCTGAGC TCGACTGCCA ACAAGGTACT CGGGCCCTGT TACAAACCCT 3400
AGGGGACCTC GGGTATCGGG CCTCGGCCAA GAAAGCCCAA ATTTGCCAAA 3450
AACAGGTCAA ATATCTGGGG TATCTCCTAA AAGAGGGTCA GAGATGGCTG 3500
ACTGAGGCCA GAAAAGAGAC TGTGATGGGG CAGCCTACTC CGAAGACCCC 3550
TCGACAACTA AGGGAGTTCC TAGGGACGGC AGGCTTCTGT CGCCTCTGGA 3600
TCCCTGGGTT TGCAGAAATG GCAGCCCCCT TGTACCCTCT CACCAAAACG 3650
GGGACTCTGT TTAATTGGGG TCCAGACCAG CAAAAAGCCT ATCAAGAAAT 3700
CAAACAGGCT CTTCTAACTG CCCCAGCCCT GGGATTGCCA GACTTGACTA 3750
AGCCCTTTGA ACTCTTTGTC GACGAGAAAC AGGGCTACGC CAAAGGCGTC 3800
CTAACGCAAA AACTGGGACC TTGGCGTCGG CCGGTGGCCT ACCTGTCTAA 3850
AAAGCTAGAC CCAGTGGCAG CTGGCTGGCC CCCTTGCCTA CGGATGGTGG 3900

*FIG._11C*

CAGCCATTGC AGTTCTGACA AAAGATGCTG GTAAGCTCAC TATGGGACAG 3950
CCATTAGTCA TTCTGGCCCC CCATGCCGTA GAGACACTAG TTAAGCAACC 4000
CCCTGATCGC TGGCTCTCCA ACGCCCGGAT GACCCATTAC CAAGCCCTGC 4050
TCCTGGACAC GGACCGGGTC CAGTTCGGGC CAGTAGTGGC CCTAAATCCA 4100
GCTACGCTGC TCCCTCTGCC TAAGGAGGGG CTGCAACATG ACTGTCTTGA 4150
CATCTTGGCT GAAGCCCACG GAACTAGATC AGATCTTACG GACCAGCCCC 4200
TCCCAGACGC CGACCACACC TGGTACACGG ATGGGAGCAG CTTCCTGCAA 4250
GAAGGGCAGC GCAAGGCCGG AGCAGCGGTG ACCACCGAGA CTGAGGTAAT 4300
CTGGGCCAGG GCATTGCCAG CCGGGACATC GGCCCAAAGA GCTGAACTGA 4350
TAGCGCTCAC CCAAGCCCTA AAGATGGCAG AAGGTAAGAA GCTAAATGTT 4400
TATACTGATA GCCGTTATGC TTTTGCCACC GCTCATATTC ATGGAGAAAT 4450
ATACAGAAGA CGCGGGTTGC TCACATCAGA AGGAAAAGAA ATCAAGAACA 4500
AGGGCGAGAT CTTAGCCCTA CTAAAGGCTC TCTTCTTGCC CAAAAGACTT 4550
AGCATAATTC ATTGCCCGGG GCATCAAAAG GGAAACAGCG CAGAGGCCAG 4600
GGGCAACCGG ATGGCTGACC AAGCGGCGCG CAAGGCAGCC ATCACAGAGA 4650
CTTAAGAGCT CCGTCGACAA GCTTGCGGCC GCACTCGAGC ACCACCACCA 4700
CCACCACTGA GATCCGGCTG CTAACAAAGC CCGAAAGGAA GCTGAGTTGG 4750
CTGCTGCCAC CGCTGAGCAA TAACTAGCAT AACCCCTTGG GGCCTCTAAA 4800
CGGGTCTTGA GGGGTTTTTT GCTGAAAGGA GGAACTATAT ATCGATGATA 4850
AGCTGTCAAA CATGAGAATT ACAACTTATA TCGTATGGGG CTGACTTCAG 4900
GTGCTACATT TGAAGAGATA AATTGCACTG AAATCTAGAA ATATTTTATC 4950
TGATTAATAA GATGATCTTC TTGAGATCGT TTTGGTCTGC GCGTAATCTC 5000
TTGCTCTGAA AACGAAAAAA CCGCCTTGCA GGGCGGTTTT TCGAAGGTTC 5050
TCTGAGCTAC CAACTCTTTG AACCGAGGTA ACTGGCTTGG AGGAGCGCAG 5100
TCACCAAAAC TTGTCCTTTC AGTTTAGCCT TAACCGGCGC ATGACTTCAA 5150
GACTAACTCC TCTAAATCAA TTACCAGTGG CTGCTGCCAG TGGTGCTTTT 5200

FIG._11D

GCATGTCTTT CCGGGTTGGA CTCAAGACGA TAGTTACCGG ATAAGGCGCA 5250
GCGGTCGGAC TGAACGGGGG GTTCGTGCAT ACAGTCCAGC TTGGAGCGAA 5300
CTGCCTACCC GGAACTGAGT GTCAGGCGTG GAATGAGACA AACGCGGCCA 5350
TAACAGCGGA ATGACACCGG TAAACCGAAA GGCAGGAACA GGAGAGCGCA 5400
CGAGGGAGCC GCCAGGGGGA AACGCCTGGT ATCTTTATAG TCCTGTCGGG 5450
TTTCGCCACC ACTGATTTGA GCGTCAGATT TCGTGATGCT TGTCAGGGGG 5500
GCGGAGCCTA TGGAAAAACG GCTTTGCCGC GGCCCTCTCA CTTCCCTGTT 5550
AAGTATCTTC CTGGCATCTT CCAGGAAATC TCCGCCCCGT TCGTAAGCCA 5600
TTTCCGCTCG CCGCAGTCGA ACGACCGAGC GTAGCGAGTC AGTGAGCGAG 5650
GAAGCGGAAT ATATCCTGTA TCACATATTC TGCTGACGCA CCGGTGCAGC 5700
CTTTTTTCTC CTGCCACATG AAGCACTTCA CTGACACCCT CATCAGTGCC 5750
AACATAGTAA GCCAGTATAC ACTCCGCTAG CGCTGATGTC CGGCGGTGCT 5800
TTTGCCGTTA CGCACCACCC CGTCAGTAGC TGAACAGGAG GGACAGCTGA 5850
TAGAAACAGA AGCCACTGGA GCACCTCAAA AACACCATCA TACACTAAAT 5900
CAGTAAGTTG GCAGCATCAC CCGACGCACT TTGCGCCGAA TAAATACCTG 5950
TGACGGAAGA TCACTTCGCA GAATAAATAA ATCCTGGTGT CCCTGTTGAT 6000
ACCGGGAAGC CCTGGGCCAA CTTTTGGCGA AAATGAGACG TTGATCGGCA 6050
CGTAAGAGGT TCCAACTTTC ACCATAATGA AATAAGATCA CTACCGGGCG 6100
TATTTTTTGA GTTATCGAGA TTTTCAGGAG CTAAGGAAGC TAAAATGGAG 6150
AAAAAAATCA CTGGATATAC CACCGTTGAT ATATCCCAAT GGCATCGTAA 6200
AGAACATTTT GAGGCATTTC AGTCAGTTGC TCAATGTACC TATAACCAGA 6250
CCGTTCAGCT GGATATTACG GCCTTTTTAA AGACCGTAAA GAAAAATAAG 6300
CACAAGTTTT ATCCGGCCTT TATTCACATT CTTGCCCGCC TGATGAATGC 6350
TCATCCGGAA TTC 6363

FIG._11E

<ligation of ocdl2.3 and ocdl2.4 into NotI/SalI cut pRK5B deleting the original NotI site but recreating one 3' to new SceI site>
<changed CT to TC at 1270 11/24/92 based on sequencing results>

<sequence of CMV enhancer/promoter, from Cell 41, 1985>
T><from pPMLCMV beginning to HindIII,enhancers and promoter>
TCGAGCTCGCCCGACATTGATTA
TTGACTAGTTATTAATAGTAATCAATTACGGGGTCATTAGTTCATAGCCC
ATATATGGAGTTCCGCGTTACATAACTTACGGTAAATGGCCCGCCTGGCT
GACCGCCCAACGACCCCCGCCCATTGACGTCAATAATGACGTATGTTCCC
ATAGTAACGCCAATAGGGACTTTCCATTGACGTCAATGGGTGGAGTATTT
ACGGTAAACTGCCCACTTGGCAGTACATCAAGTGTATCATATGCCAAGTA
CGCCCCCTATTGACGTCAATGACGGTAAATGGCCCGCCTGGCATTATGCC
CAGTACATGACCTTATGGGACTTTCCTACTTGGCAGTACATCTACGTATT
AGTCATCGCTATTACCATGGTGATGCGGTTTTGGCAGTACATCAATGGGC
GTGGATAGCGGTTTGACTCACGGGGATTTCCAAGTCTCCACCCCATTGAC
GTCAATGGGAGTTTGTTTTGGCACCAAAATCAACGGGACTTTCCAAAATG
TCGTAACAACTCCGCCCCATTGACGCAAATGGGCGGTAGGCGTGTACGGT
GGGAGGTCTATATAAGCAGAGCTCGTTTAGTGAACCG
<Begin RNA>
TCAGATCGCCTGG
AGACGCCATCCACGCTGTTTTGACCTCCATAGAAGACACCGGGACCGATC
CAGCCTCCGCGGCCGGGAACGGTGCATTGGAACGCGGATTCCCCGTGCCA
AGAGTGACGTAAGTACCGCCTATAGAGTCTATAGGCCCA><remove 5C and bstXI site>CTTGGCT
T
><sp6 promoter>
<GGCCCACCCCCTTGGCTT>CGTTAGAACGCGGCTACAATTAATACATAACC
TTATGTATCATACACATACGATTTAGGTGACACTATA><sp6 RNA start>GAATA<ACATCCACTTTGCCTTTC>

FIG._12A

ACATCCACTTTGCCTTTCTCTCC
ACAGGTGTCCACTCCCAGGTCCAA<PstI-ClaI converter>CTGCA

><cloning linker>CCTCGGTTCTATCGATTGAATTCCCCGGGGATCCTCTAGA

><451 bp xba I from cdm7 inserted here>GATCCCTCGACC
TCGAGATCCATTGTGCTGGCGCGGATTCTTTATCACTGATAAGTTGGTGGACATATTATG
TTTATCAGTGATAAAGTGTCAAGCATGACAAAGTTGCAGCCGAATACAGTGATCCGTGCC
GCCCTAGACCTGTTGAACGAGGTCGGCGTAGACGGTCTGACGACACGCAAACTGGCGGAA
CGGTTGGGGGTTCAGCAGCCGGCGCTTTACTGGCACTTCAGGAACAAGCGGGCGCTGCTC
GACGCACTGGCCGAAGCCATGCTGGCGGAGAATCATAGCACTTCGGTGCCGAGAGCCGAC
GACGACTGGCGCTCATTTCTGATCGGGAATGCCCGCAGCTTCAGGCAGGCGCTGCTCGCC
TACCGCCAGCACAATGGATCTCGAGGGATCTTCCATACCTACCAGTTCTGCGCCTGCAGG
TCGC <linker to insert SceI site between NotI and SalI sites of pRK5B>
GGCCTAGGGATAACAGGGTAATGCGGCCGCG TCGACCTGCAGAAGCTT
GGCCGCCATGGCCC
><sv40 early poly A>AACTTGTTTATTGCAGCTTATAATGGTT
ACAAATAAAGCAATAGCATCACAAATTTCACAAATAAAGCATTTTTTTCACTGCATTCTA
GTTGTGGTTTGTCCAAACTCATCAATGTATCTTATCATGTCT
GGATCGG
><sv40 origin>G
AATTAATTCGGCGCAGCACCATGGCCTGAAATAACCTCTGAAAGAGGAACTTGGTTAGGTACCTTC
TGAGGCGGAAAGAACCAGCT
GTGGAATGTGTGTCAGTTAGGGTGTGGAAAGTCCCCAGGCTCCCCAGCAGGC
AGAAGTATGCAAAGCATGCATCTCAATTAGTCAGCAACCAGGTGTGGAAAGTCCCCAGGC
TCCCCAGCAGGCAGAAGTATGCAAAGCATGCATCTCAATTAGTCAGCAACCATAGTCCCG
CCCCTAACTCCGCCCATCCCGCCCCTAACTCCGCCCAGTTCCGCCCATTCTCCGCCCCAT
GGCTGACTAATTTTTTTTATTTATGCAGAGGCCGAGGCCGCCTCGGCCTCTGAGCTATTC
CAGAAGTAGTGAGGAGGCTTTTTTGGAGGCCTAGGCTTTTGCAAA

FIG._12B

```
><start pUC118>
AAGCTGTTAAC

<new pUC118>
AGCTTGGCACTGGCCGTCGTTTTACAACGTCGTGACTGGGAAAAC
CCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGG
CGCCTGATGCGGTATTTTCTCCTTACGCATCTGTGCGGTATTTCACACCGCATACGTCAA
AGCAACCATAGTACGCGCCCTGTAGCGGCGCATTAAGCGCGGCGGGTGTGGTGGTTACGC
GCAGCGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAAC
TTGATTTGGGTGATGGTTCACGTAGTGGGCCATCGCCCTGATAGACGGTTTTTCGCCCTT
TGACGTTGGAGTCCACGTTCTTTAATAGTGGACTCTTGTTCCAAACTGGAACAACACTCA
ACCCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGTTTA
CAATTTTATGGTGCACTCTCAGTACAATCTGCTCTGATGCCGCATAGTTAAGCCAGCCCC
GACACCCGCCAACACCCGCTGACGCGCCCTGACGGGCTTGTCTGCTCCCGGCATCCGCTT
ACAGACAAGCTGTGACCGTCTCCGGGAGCTGCATGTGTCAGAGGTTTTCACCGTCATCAC
CGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTA
TTTGTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAACTCG
GTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTT
TGCACAACATGGGGGATCATGTAACTCGCCTTGATCGTTGGGAACCGGAGCTGAATGAAG
CCATACCAAACGACGAGCGTGACACCACGATGCCTGTAGCAATGGCAACAACGTTGCGCA
AACTATTAACTGGCGAACTACTTACTCTAGCTTCCCGGCAACAATTAATAGACTGGATGG
```

FIG._12C

AGGCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTCGT
TCCACTGAGCGTCAGACCCCGTAGAAAAGATCAAAGGATCTTCTTGAGATCCTTTTTTTC
TGCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCGGGCT
GAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGATTTTTGT
GATGCTCGTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGATTCTG
TGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTCC
CCGCGCGTTGGCCGATTCATTAATGCAGCTGGCACGACAGGTTTCCCGACTGGAAAGCGG
GCAGTGAGCGCAACGCAATTAATGTGAGTTAGCTCACTCATTAGGCACCCCAGGCTTTAC
ACTTTATGCTTCCGGCTCGTATGTTGTGTGGAATTGTGAGCGGATAACAATTTCACACAG
GAAACAGCTATGACATGATTACGAATT
AA

FIG._12D

| | | |
|---|---|---|
| pRK5 | 1 | TTCGAGCTCGCCCGACATTGATTATTGACTAGTTATTAATAGTAATCAAT |
| pRK5C | 1 | TTCGAGCTCGCCCGACATTGATTATTGACTAGTTATTAATAGTAATCAAT |
| pRK5 | 51 | TACGGGGTCATTAGTTCATAGCCCATATATGGAGTTCCGCGTTACATAAC |
| pRK5C | 51 | TACGGGGTCATTAGTTCATAGCCCATATATGGAGTTCCGCGTTACATAAC |
| pRK5 | 101 | TTACGGTAAATGGCCCGCCTGGCTGACCGCCCAACGACCCCCGCCCATTG |
| pRK5C | 101 | TTACGGTAAATGGCCCGCCTGGCTGACCGCCCAACGACCCCCGCCCATTG |
| pRK5 | 151 | ACGTCAATAATGACGTATGTTCCCATAGTAACGCCAATAGGGACTTTCCA |
| pRK5C | 151 | ACGTCAATAATGACGTATGTTCCCATAGTAACGCCAATAGGGACTTTCCA |
| pRK5 | 201 | TTGACGTCAATGGGTGGAGTATTTACGGTAAACTGCCCACTTGGCAGTAC |
| pRK5C | 201 | TTGACGTCAATGGGTGGAGTATTTACGGTAAACTGCCCACTTGGCAGTAC |
| pRK5 | 251 | ATCAAGTGTATCATATGCCAAGTACGCCCCCTATTGACGTCAATGACGGT |
| pRK5C | 251 | ATCAAGTGTATCATATGCCAAGTACGCCCCCTATTGACGTCAATGACGGT |
| pRK5 | 301 | AAATGGCCCGCCTGGCATTATGCCCAGTACATGACCTTATGGGACTTTCC |
| pRK5C | 301 | AAATGGCCCGCCTGGCATTATGCCCAGTACATGACCTTATGGGACTTTCC |
| pRK5 | 351 | TACTTGGCAGTACATCTACGTATTAGTCATCGCTATTACCATGGTGATGC |
| pRK5C | 351 | TACTTGGCAGTACATCTACGTATTAGTCATCGCTATTACCATGGTGATGC |
| pRK5 | 401 | GGTTTTGGCAGTACATCAATGGGCGTGGATAGCGGTTTGACTCACGGGGA |
| pRK5C | 401 | GGTTTTGGCAGTACATCAATGGGCGTGGATAGCGGTTTGACTCACGGGGA |
| pRK5 | 451 | TTTCCAAGTCTCCACCCCATTGACGTCAATGGGAGTTTGTTTTGGCACCA |
| pRK5C | 451 | TTTCCAAGTCTCCACCCCATTGACGTCAATGGGAGTTTGTTTTGGCACCA |
| pRK5 | 501 | AAATCAACGGGACTTTCCAAAATGTCGTAACAACTCCGCCCCATTGACGC |
| pRK5C | 501 | AAATCAACGGGACTTTCCAAAATGTCGTAACAACTCCGCCCCATTGACGC |
| pRK5 | 551 | AAATGGGCGGTAGGCGTGTACGGTGGGAGGTCTATATAAGCAGAGCTCGT |
| pRK5C | 551 | AAATGGGCGGTAGGCGTGTACGGTGGGAGGTCTATATAAGCAGAGCTCGT |

FIG._13A

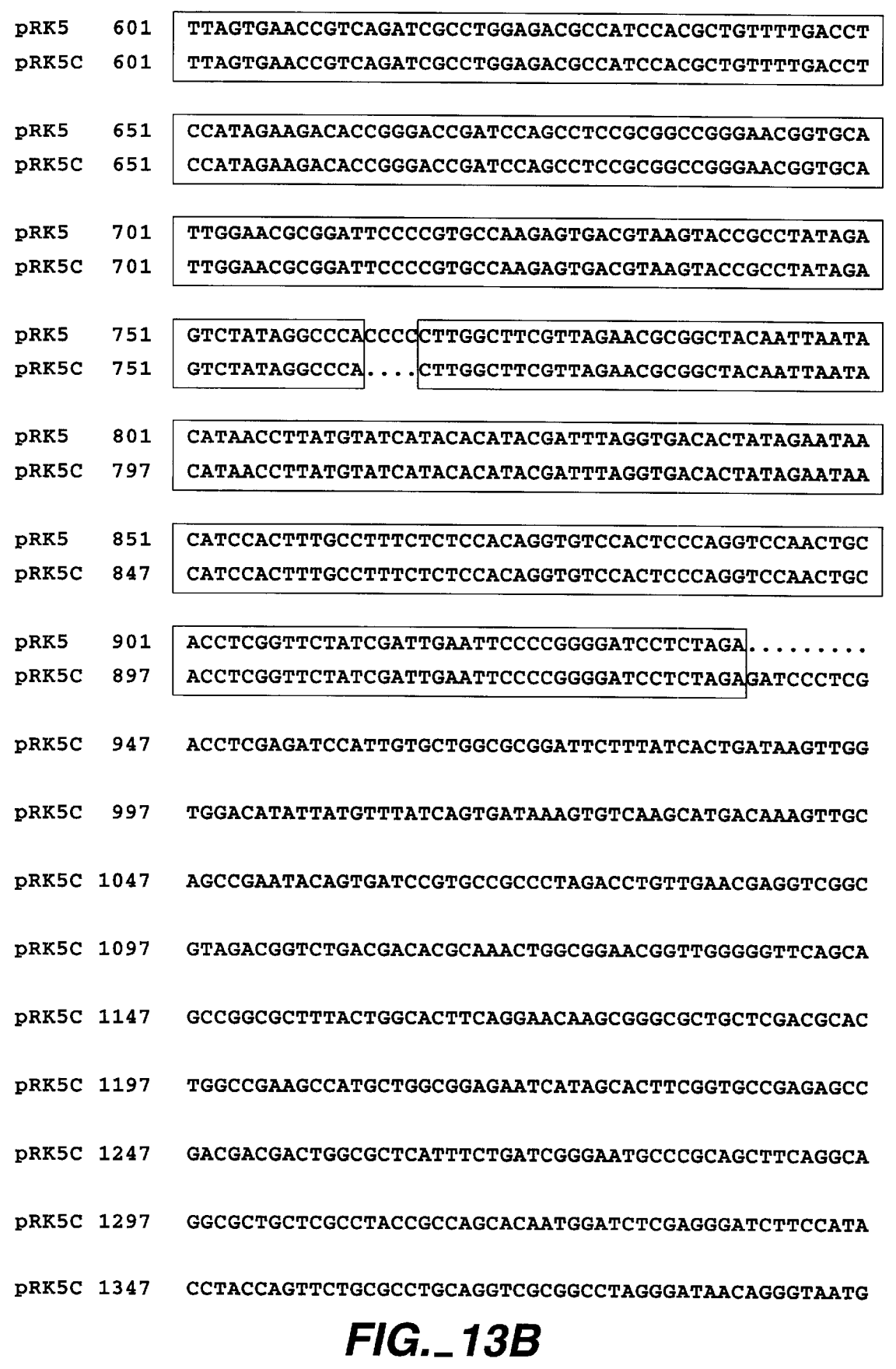

```
pRK5    601  TTAGTGAACCGTCAGATCGCCTGGAGACGCCATCCACGCTGTTTTGACCT
pRK5C   601  TTAGTGAACCGTCAGATCGCCTGGAGACGCCATCCACGCTGTTTTGACCT

pRK5    651  CCATAGAAGACACCGGGACCGATCCAGCCTCCGCGGCCGGGAACGGTGCA
pRK5C   651  CCATAGAAGACACCGGGACCGATCCAGCCTCCGCGGCCGGGAACGGTGCA

pRK5    701  TTGGAACGCGGATTCCCCGTGCCAAGAGTGACGTAAGTACCGCCTATAGA
pRK5C   701  TTGGAACGCGGATTCCCCGTGCCAAGAGTGACGTAAGTACCGCCTATAGA

pRK5    751  GTCTATAGGCCCACCCCCTTGGCTTCGTTAGAACGCGGCTACAATTAATA
pRK5C   751  GTCTATAGGCCCA....CTTGGCTTCGTTAGAACGCGGCTACAATTAATA

pRK5    801  CATAACCTTATGTATCATACACATACGATTTAGGTGACACTATAGAATAA
pRK5C   797  CATAACCTTATGTATCATACACATACGATTTAGGTGACACTATAGAATAA

pRK5    851  CATCCACTTTGCCTTTCTCTCCACAGGTGTCCACTCCCAGGTCCAACTGC
pRK5C   847  CATCCACTTTGCCTTTCTCTCCACAGGTGTCCACTCCCAGGTCCAACTGC

pRK5    901  ACCTCGGTTCTATCGATTGAATTCCCCGGGGATCCTCTAGA.........
pRK5C   897  ACCTCGGTTCTATCGATTGAATTCCCCGGGGATCCTCTAGAGATCCCTCG

pRK5C   947  ACCTCGAGATCCATTGTGCTGGCGCGGATTCTTTATCACTGATAAGTTGG

pRK5C   997  TGGACATATTATGTTTATCAGTGATAAAGTGTCAAGCATGACAAAGTTGC

pRK5C  1047  AGCCGAATACAGTGATCCGTGCCGCCCTAGACCTGTTGAACGAGGTCGGC

pRK5C  1097  GTAGACGGTCTGACGACACGCAAACTGGCGGAACGGTTGGGGGTTCAGCA

pRK5C  1147  GCCGGCGCTTTACTGGCACTTCAGGAACAAGCGGGCGCTGCTCGACGCAC

pRK5C  1197  TGGCCGAAGCCATGCTGGCGGAGAATCATAGCACTTCGGTGCCGAGAGCC

pRK5C  1247  GACGACGACTGGCGCTCATTTCTGATCGGGAATGCCCGCAGCTTCAGGCA

pRK5C  1297  GGCGCTGCTCGCCTACCGCCAGCACAATGGATCTCGAGGGATCTTCCATA

pRK5C  1347  CCTACCAGTTCTGCGCCTGCAGGTCGCGGCCTAGGGATAACAGGGTAATG
```

FIG._13B

```
pRK5    942  .......GTCGACCTGCAGAAGCTTGGCCGCCATGGCCCAACTTGTTTAT
pRK5C  1397  CGGCCGCGTCGACCTGCAGAAGCTTGGCCGCCATGGCCCAACTTGTTTAT

pRK5    985  TGCAGCTTATAATGGTTACAAATAAAGCAATAGCATCACAAATTTCACAA
pRK5C  1447  TGCAGCTTATAATGGTTACAAATAAAGCAATAGCATCACAAATTTCACAA

pRK5   1035  ATAAAGCATTTTTTTCACTGCATTCTAGTTGTGGTTTGTCCAAACTCATC
pRK5C  1497  ATAAAGCATTTTTTTCACTGCATTCTAGTTGTGGTTTGTCCAAACTCATC

pRK5   1085  AATGTATCTTATCATGTCTGGATCGGGAATTAATTCGGCGCAGCACCATG
pRK5C  1547  AATGTATCTTATCATGTCTGGATCGGGAATTAATTCGGCGCAGCACCATG

pRK5   1135  GCCTGAAATAACCTCTGAAAGAGGAACTTGGTTAGGTACCTTCTGAGGCG
pRK5C  1597  GCCTGAAATAACCTCTGAAAGAGGAACTTGGTTAGGTACCTTCTGAGGCG

pRK5   1185  GAAAGAACCAGCTGTGGAATGTGTGTCAGTTAGGGTGTGGAAAGTCCCCA
pRK5C  1647  GAAAGAACCAGCTGTGGAATGTGTGTCAGTTAGGGTGTGGAAAGTCCCCA

pRK5   1235  GGCTCCCCAGCAGGCAGAAGTATGCAAAGCATGCATCTCAATTAGTCAGC
pRK5C  1697  GGCTCCCCAGCAGGCAGAAGTATGCAAAGCATGCATCTCAATTAGTCAGC

pRK5   1285  AACCAGGTGTGGAAAGTCCCCAGGCTCCCCAGCAGGCAGAAGTATGCAAA
pRK5C  1747  AACCAGGTGTGGAAAGTCCCCAGGCTCCCCAGCAGGCAGAAGTATGCAAA

pRK5   1335  GCATGCATCTCAATTAGTCAGCAACCATAGTCCCGCCCCTAACTCCGCCC
pRK5C  1797  GCATGCATCTCAATTAGTCAGCAACCATAGTCCCGCCCCTAACTCCGCCC

pRK5   1385  ATCCCGCCCCTAACTCCGCCCAGTTCCGCCCATTCTCCGCCCCATGGCTG
pRK5C  1847  ATCCCGCCCCTAACTCCGCCCAGTTCCGCCCATTCTCCGCCCCATGGCTG

pRK5   1435  ACTAATTTTTTTTATTTATGCAGAGGCCGAGGCCGCCTCGGCCTCTGAGC
pRK5C  1897  ACTAATTTTTTTTATTTATGCAGAGGCCGAGGCCGCCTCGGCCTCTGAGC

pRK5   1485  TATTCCAGAAGTAGTGAGGAGGCTTTTTTGGAGGCCTAGGCTTTTGCAAA
pRK5C  1947  TATTCCAGAAGTAGTGAGGAGGCTTTTTTGGAGGCCTAGGCTTTTGCAAA
```

FIG._13C

| | | |
|---|---|---|
| pRK5 | 1535 | AAGCTGTTAACAGCTTGGCACTGGCCGTCGTTTTACAACGTCGTGACTGG |
| pRK5C | 1997 | AAGCTGTTAACAGCTTGGCACTGGCCGTCGTTTTACAACGTCGTGACTGG |
| pRK5 | 1585 | GAAAACCCTGGCGTTACCCAACTTAATCGCCTTGCAGCACATCCCCCTTT |
| pRK5C | 2047 | GAAAACCCTGGCGTTACCCAACTTAATCGCCTTGCAGCACATCCCCCTTT |
| pRK5 | 1635 | CGCCAGCTGGCGTAATAGCGAAGAGGCCCGCACCGATCGCCCTTCCCAAC |
| pRK5C | 2097 | CGCCAGCTGGCGTAATAGCGAAGAGGCCCGCACCGATCGCCCTTCCCAAC |
| pRK5 | 1685 | AGTTGCGCAGCCTGAATGGCGAATGGCGCCTGATGCGGTATTTTCTCCTT |
| pRK5C | 2147 | AGTTGCGCAGCCTGAATGGCGAATGGCGCCTGATGCGGTATTTTCTCCTT |
| pRK5 | 1735 | ACGCATCTGTGCGGTATTTCACACCGCATACGTCAAAGCAACCATAGTAC |
| pRK5C | 2197 | ACGCATCTGTGCGGTATTTCACACCGCATACGTCAAAGCAACCATAGTAC |
| pRK5 | 1785 | GCGCCCTGTAGCGGCGCATTAAGCGCGGCGGGTGTGGTGGTTACGCGCAG |
| pRK5C | 2247 | GCGCCCTGTAGCGGCGCATTAAGCGCGGCGGGTGTGGTGGTTACGCGCAG |
| pRK5 | 1835 | CGTGACCGCTACACTTGCCAGCGCCCTAGCGCCCGCTCCTTTCGCTTTCT |
| pRK5C | 2297 | CGTGACCGCTACACTTGCCAGCGCCCTAGCGCCCGCTCCTTTCGCTTTCT |
| pRK5 | 1885 | TCCCTTCCTTTCTCGCCACGTTCGCCGGCTTTCCCCGTCAAGCTCTAAAT |
| pRK5C | 2347 | TCCCTTCCTTTCTCGCCACGTTCGCCGGCTTTCCCCGTCAAGCTCTAAAT |
| pRK5 | 1935 | CGGGGGCTCCCTTTAGGGTTCCGATTTAGTGCTTTACGGCACCTCGACCC |
| pRK5C | 2397 | CGGGGGCTCCCTTTAGGGTTCCGATTTAGTGCTTTACGGCACCTCGACCC |
| pRK5 | 1985 | CAAAAAACTTGATTTGGGTGATGGTTCACGTAGTGGGCCATCGCCCTGAT |
| pRK5C | 2447 | CAAAAAACTTGATTTGGGTGATGGTTCACGTAGTGGGCCATCGCCCTGAT |
| pRK5 | 2035 | AGACGGTTTTTCGCCCTTTGACGTTGGAGTCCACGTTCTTTAATAGTGGA |
| pRK5C | 2497 | AGACGGTTTTTCGCCCTTTGACGTTGGAGTCCACGTTCTTTAATAGTGGA |
| pRK5 | 2085 | CTCTTGTTCCAAACTGGAACAACACTCAACCCTATCTCGGGCTATTCTTT |
| pRK5C | 2547 | CTCTTGTTCCAAACTGGAACAACACTCAACCCTATCTCGGGCTATTCTTT |

FIG._13D

| | | |
|---|---|---|
| pRK5 | 2135 | TGATTTATAAGGGATTTTGCCGATTTCGGCCTATTGGTTAAAAAATGAGC |
| pRK5C | 2597 | TGATTTATAAGGGATTTTGCCGATTTCGGCCTATTGGTTAAAAAATGAGC |
| pRK5 | 2185 | TGATTTAACAAAAATTTAACGCGAATTTTAACAAAATATTAACGTTTACA |
| pRK5C | 2647 | TGATTTAACAAAAATTTAACGCGAATTTTAACAAAATATTAACGTTTACA |
| pRK5 | 2235 | ATTTTATGGTGCACTCTCAGTACAATCTGCTCTGATGCCGCATAGTTAAG |
| pRK5C | 2697 | ATTTTATGGTGCACTCTCAGTACAATCTGCTCTGATGCCGCATAGTTAAG |
| pRK5 | 2285 | CCAGCCCCGACACCCGCCAACACCCGCTGACGCGCCCTGACGGGCTTGTC |
| pRK5C | 2747 | CCAGCCCCGACACCCGCCAACACCCGCTGACGCGCCCTGACGGGCTTGTC |
| pRK5 | 2335 | TGCTCCCGGCATCCGCTTACAGACAAGCTGTGACCGTCTCCGGGAGCTGC |
| pRK5C | 2797 | TGCTCCCGGCATCCGCTTACAGACAAGCTGTGACCGTCTCCGGGAGCTGC |
| pRK5 | 2385 | ATGTGTCAGAGGTTTTCACCGTCATCACCGAAACGCGCGAGACGAAAGGG |
| pRK5C | 2847 | ATGTGTCAGAGGTTTTCACCGTCATCACCGAAACGCGCGAGACGAAAGGG |
| pRK5 | 2435 | CCTCGTGATACGCCTATTTTTATAGGTTAATGTCATGATAATAATGGTTT |
| pRK5C | 2897 | CCTCGTGATACGCCTATTTTTATAGGTTAATGTCATGATAATAATGGTTT |
| pRK5 | 2485 | CTTAGACGTCAGGTGGCACTTTTCGGGGAAATGTGCGCGGAACCCCTATT |
| pRK5C | 2947 | CTTAGACGTCAGGTGGCACTTTTCGGGGAAATGTGCGCGGAACCCCTATT |
| pRK5 | 2535 | TGTTTATTTTTCTAAATACATTCAAATATGTATCCGCTCATGAGACAATA |
| pRK5C | 2997 | TGTTTATTTTTCTAAATACATTCAAATATGTATCCGCTCATGAGACAATA |
| pRK5 | 2585 | ACCCTGATAAATGCTTCAATAATATTGAAAAAGGAAGAGTATGAGTATTC |
| pRK5C | 3047 | ACCCTGATAAATGCTTCAATAATATTGAAAAAGGAAGAGTATGAGTATTC |
| pRK5 | 2635 | AACATTTCCGTGTCGCCCTTATTCCCTTTTTTGCGGCATTTTGCCTTCCT |
| pRK5C | 3097 | AACATTTCCGTGTCGCCCTTATTCCCTTTTTTGCGGCATTTTGCCTTCCT |
| pRK5 | 2685 | GTTTTTGCTCACCCAGAAACGCTGGTGAAAGTAAAAGATGCTGAAGATCA |
| pRK5C | 3147 | GTTTTTGCTCACCCAGAAACGCTGGTGAAAGTAAAAGATGCTGAAGATCA |

FIG._13E

| | | |
|---|---|---|
| pRK5 | 2735 | GTTGGGTGCACGAGTGGGTTACATCGAACTGGATCTCAACAGCGGTAAGA |
| pRK5C | 3197 | GTTGGGTGCACGAGTGGGTTACATCGAACTGGATCTCAACAGCGGTAAGA |
| pRK5 | 2785 | TCCTTGAGAGTTTTCGCCCCGAAGAACGTTTTCCAATGATGAGCACTTTT |
| pRK5C | 3247 | TCCTTGAGAGTTTTCGCCCCGAAGAACGTTTTCCAATGATGAGCACTTTT |
| pRK5 | 2835 | AAAGTTCTGCTATGTGGCGCGGTATTATCCCGTATTGACGCCGGGCAAGA |
| pRK5C | 3297 | AAAGTTCTGCTATGTGGCGCGGTATTATCCCGTATTGACGCCGGGCAAGA |
| pRK5 | 2885 | GCAACTCGGTCGCCGCATACACTATTCTCAGAATGACTTGGTTGAGTACT |
| pRK5C | 3347 | GCAACTCGGTCGCCGCATACACTATTCTCAGAATGACTTGGTTGAGTACT |
| pRK5 | 2935 | CACCAGTCACAGAAAAGCATCTTACGGATGGCATGACAGTAAGAGAATTA |
| pRK5C | 3397 | CACCAGTCACAGAAAAGCATCTTACGGATGGCATGACAGTAAGAGAATTA |
| pRK5 | 2985 | TGCAGTGCTGCCATAACCATGAGTGATAACACTGCGGCCAACTTACTTCT |
| pRK5C | 3447 | TGCAGTGCTGCCATAACCATGAGTGATAACACTGCGGCCAACTTACTTCT |
| pRK5 | 3035 | GACAACGATCGGAGGACCGAAGGAGCTAACCGCTTTTTTGCACAACATGG |
| pRK5C | 3497 | GACAACGATCGGAGGACCGAAGGAGCTAACCGCTTTTTTGCACAACATGG |
| pRK5 | 3085 | GGGATCATGTAACTCGCCTTGATCGTTGGGAACCGGAGCTGAATGAAGCC |
| pRK5C | 3547 | GGGATCATGTAACTCGCCTTGATCGTTGGGAACCGGAGCTGAATGAAGCC |
| pRK5 | 3135 | ATACCAAACGACGAGCGTGACACCACGATGCCTGTAGCAATGGCAACAAC |
| pRK5C | 3597 | ATACCAAACGACGAGCGTGACACCACGATGCCTGTAGCAATGGCAACAAC |
| pRK5 | 3185 | GTTGCGCAAACTATTAACTGGCGAACTACTTACTCTAGCTTCCCGGCAAC |
| pRK5C | 3647 | GTTGCGCAAACTATTAACTGGCGAACTACTTACTCTAGCTTCCCGGCAAC |
| pRK5 | 3235 | AATTAATAGACTGGATGGAGGCGGATAAAGTTGCAGGACCACTTCTGCGC |
| pRK5C | 3697 | AATTAATAGACTGGATGGAGGCGGATAAAGTTGCAGGACCACTTCTGCGC |
| pRK5 | 3285 | TCGGCCCTTCCGGCTGGCTGGTTTATTGCTGATAAATCTGGAGCCGGTGA |
| pRK5C | 3747 | TCGGCCCTTCCGGCTGGCTGGTTTATTGCTGATAAATCTGGAGCCGGTGA |

FIG._13F

| | | |
|---|---|---|
| pRK5 | 3335 | GCGTGGGTCTCGCGGTATCATTGCAGCACTGGGGCCAGATGGTAAGCCCT |
| pRK5C | 3797 | GCGTGGGTCTCGCGGTATCATTGCAGCACTGGGGCCAGATGGTAAGCCCT |
| pRK5 | 3385 | CCCGTATCGTAGTTATCTACACGACGGGGAGTCAGGCAACTATGGATGAA |
| pRK5C | 3847 | CCCGTATCGTAGTTATCTACACGACGGGGAGTCAGGCAACTATGGATGAA |
| pRK5 | 3435 | CGAAATAGACAGATCGCTGAGATAGGTGCCTCACTGATTAAGCATTGGTA |
| pRK5C | 3897 | CGAAATAGACAGATCGCTGAGATAGGTGCCTCACTGATTAAGCATTGGTA |
| pRK5 | 3485 | ACTGTCAGACCAAGTTTACTCATATATACTTTAGATTGATTTAAAACTTC |
| pRK5C | 3947 | ACTGTCAGACCAAGTTTACTCATATATACTTTAGATTGATTTAAAACTTC |
| pRK5 | 3535 | ATTTTTAATTTAAAAGGATCTAGGTGAAGATCCTTTTTGATAATCTCATG |
| pRK5C | 3997 | ATTTTTAATTTAAAAGGATCTAGGTGAAGATCCTTTTTGATAATCTCATG |
| pRK5 | 3585 | ACCAAAATCCCTTAACGTGAGTTTTCGTTCCACTGAGCGTCAGACCCCGT |
| pRK5C | 4047 | ACCAAAATCCCTTAACGTGAGTTTTCGTTCCACTGAGCGTCAGACCCCGT |
| pRK5 | 3635 | AGAAAAGATCAAAGGATCTTCTTGAGATCCTTTTTTTCTGCGCGTAATCT |
| pRK5C | 4097 | AGAAAAGATCAAAGGATCTTCTTGAGATCCTTTTTTTCTGCGCGTAATCT |
| pRK5 | 3685 | GCTGCTTGCAAACAAAAAAACCACCGCTACCAGCGGTGGTTTGTTTGCCG |
| pRK5C | 4147 | GCTGCTTGCAAACAAAAAAACCACCGCTACCAGCGGTGGTTTGTTTGCCG |
| pRK5 | 3735 | GATCAAGAGCTACCAACTCTTTTTCCGAAGGTAACTGGCTTCAGCAGAGC |
| pRK5C | 4197 | GATCAAGAGCTACCAACTCTTTTTCCGAAGGTAACTGGCTTCAGCAGAGC |
| pRK5 | 3785 | GCAGATACCAAATACTGTTCTTCTAGTGTAGCCGTAGTTAGGCCACCACT |
| pRK5C | 4247 | GCAGATACCAAATACTGTTCTTCTAGTGTAGCCGTAGTTAGGCCACCACT |
| pRK5 | 3835 | TCAAGAACTCTGTAGCACCGCCTACATACCTCGCTCTGCTAATCCTGTTA |
| pRK5C | 4297 | TCAAGAACTCTGTAGCACCGCCTACATACCTCGCTCTGCTAATCCTGTTA |
| pRK5 | 3885 | CCAGTGGCTGCTGCCAGTGGCGATAAGTCGTGTCTTACCGGGTTGGACTC |
| pRK5C | 4347 | CCAGTGGCTGCTGCCAGTGGCGATAAGTCGTGTCTTACCGGGTTGGACTC |

FIG._13G

| | | |
|---|---|---|
| pRK5 | 3935 | AAGACGATAGTTACCGGATAAGGCGCAGCGGTCGGGCTGAACGGGGGGTT |
| pRK5C | 4397 | AAGACGATAGTTACCGGATAAGGCGCAGCGGTCGGGCTGAACGGGGGGTT |
| pRK5 | 3985 | CGTGCACACAGCCCAGCTTGGAGCGAACGACCTACACCGAACTGAGATAC |
| pRK5C | 4447 | CGTGCACACAGCCCAGCTTGGAGCGAACGACCTACACCGAACTGAGATAC |
| pRK5 | 4035 | CTACAGCGTGAGCTATGAGAAAGCGCCACGCTTCCCGAAGGGAGAAAGGC |
| pRK5C | 4497 | CTACAGCGTGAGCTATGAGAAAGCGCCACGCTTCCCGAAGGGAGAAAGGC |
| pRK5 | 4085 | GGACAGGTATCCGGTAAGCGGCAGGGTCGGAACAGGAGAGCGCACGAGGG |
| pRK5C | 4547 | GGACAGGTATCCGGTAAGCGGCAGGGTCGGAACAGGAGAGCGCACGAGGG |
| pRK5 | 4135 | AGCTTCCAGGGGGAAACGCCTGGTATCTTTATAGTCCTGTCGGGTTTCGC |
| pRK5C | 4597 | AGCTTCCAGGGGGAAACGCCTGGTATCTTTATAGTCCTGTCGGGTTTCGC |
| pRK5 | 4185 | CACCTCTGACTTGAGCGTCGATTTTTGTGATGCTCGTCAGGGGGGCGGAG |
| pRK5C | 4647 | CACCTCTGACTTGAGCGTCGATTTTTGTGATGCTCGTCAGGGGGGCGGAG |
| pRK5 | 4235 | CCTATGGAAAAACGCCAGCAACGCGGCCTTTTTACGGTTCCTGGCCTTTT |
| pRK5C | 4697 | CCTATGGAAAAACGCCAGCAACGCGGCCTTTTTACGGTTCCTGGCCTTTT |
| pRK5 | 4285 | GCTGGCCTTTTGCTCACATGTTCTTTCCTGCGTTATCCCCTGATTCTGTG |
| pRK5C | 4747 | GCTGGCCTTTTGCTCACATGTTCTTTCCTGCGTTATCCCCTGATTCTGTG |
| pRK5 | 4335 | GATAACCGTATTACCGCCTTTGAGTGAGCTGATACCGCTCGCCGCAGCCG |
| pRK5C | 4797 | GATAACCGTATTACCGCCTTTGAGTGAGCTGATACCGCTCGCCGCAGCCG |
| pRK5 | 4385 | AACGACCGAGCGCAGCGAGTCAGTGAGCGAGGAAGCGGAAGAGCGCCCAA |
| pRK5C | 4847 | AACGACCGAGCGCAGCGAGTCAGTGAGCGAGGAAGCGGAAGAGCGCCCAA |
| pRK5 | 4435 | TACGCAAACCGCCTCTCCCCGCGCGTTGGCCGATTCATTAATGCAGCTGG |
| pRK5C | 4897 | TACGCAAACCGCCTCTCCCCGCGCGTTGGCCGATTCATTAATGCAGCTGG |
| pRK5 | 4485 | CACGACAGGTTTCCCGACTGGAAAGCGGGCAGTGAGCGCAACGCAATTAA |
| pRK5C | 4947 | CACGACAGGTTTCCCGACTGGAAAGCGGGCAGTGAGCGCAACGCAATTAA |

FIG._13H

| | | |
|---|---|---|
| pRK5 | 4535 | TGTGAGTTAGCTCACTCATTAGGCACCCCAGGCTTTACACTTTATGCTTC |
| pRK5C | 4997 | TGTGAGTTAGCTCACTCATTAGGCACCCCAGGCTTTACACTTTATGCTTC |
| pRK5 | 4585 | CGGCTCGTATGTTGTGTGGAATTGTGAGCGGATAACAATTTCACACAGGA |
| pRK5C | 5047 | CGGCTCGTATGTTGTGTGGAATTGTGAGCGGATAACAATTTCACACAGGA |
| pRK5 | 4635 | AACAGCTATGACATGATTACGAATTAA |
| pRK5C | 5097 | AACAGCTATGACATGATTACGAATTAA |

FIG._13I

CONSTRUCTION OF FULL LENGTH CDNA LIBRARIES

This application is a continuation of 08/782,861 filed Oct. 15, 1996 now abandoned.

FIELD OF THE INVENTION

The present invention relates to the construction of cDNA libraries, and in particular to methods of producing double stranded cDNA from mRNA, to methods of constructing full-length, directionally cloned cDNA libraries, to methods of screening these libraries for nucleic acid encoding a desired polypeptide, and to prokaryotic and eukaryotic cells and cell lines useful in these methods.

It is well known in the art to construct complementary DNA (cDNA) libraries from mRNA isolated from a cellular source, and to screen these libraries for nucleic acid encoding a desired polypeptide. General protocols are, for example, described in Chapter 5 of Ausubel et al., Current Protocols in Molecular Biology, Volume 1, Greene Publishing Ass. and Wiley-Interscience, 1991. Two commonly used methods of producing cDNA from mRNA are described in Okayama and Berg, *Mol. Cell Biol.* 2, 161–170 (1982) and Gubler and Hoffman, *Gene* 25 263–269, (1983).

In a typical procedure, poly$(A)^+$ mRNAs are isolated from cells, preferably a cell type in which the mRNA encoding the desired polypeptide is produced in large quantities. The mRNAs are then converted into double stranded cDNA (dscDNA) in vitro using the enzyme reverse transcriptase to synthesize complementary cDNA strands from the mRNA template.

Reverse transcriptases have been traditionally purified from retroviruses, such as avian myoblastosis virus (AMV) and Moloney murine leukemia virus (M-MuLV), which use them to make DNA copies of their own RNA genomes. The M-MuLV reverse transcriptase has also been purified from overproducing *E. coli* cells containing the cloned gene. Tanese et al. in *PNAS USA* 82, 4944–4948 (1985) and Roth et al. in *J. Biol. Chem.* 260(16), 9326–9335 (1985) report on the expression, isolation and characterization of a reverse transcriptase isolated from Moloney murine leukemia virus (M-MuLV). This reverse transcriptase is encoded by the viral pol gene and is a monomer having a molecular weight of about 80 kD. The authors demonstrate that in addition to reverse transcriptase activity, the enzyme has nuclease activity (RNase H), which degrades RNA in RNA:DNA hybrids produced when the reverse transcriptase produces the first strand of the cDNA using mRNA as a template (see also U.S. Pat. No. 4,943,531).

In the process of converting mRNA into double stranded cDNA in vitro, a first cDNA strand is synthesized by the reverse transcriptase and separated from the mRNA by treatment with alkali or using a nuclease such as the enzyme RNase H. Conveniently, this step can be achieved using a reverse transcriptase that also has RNase H activity. *E. coli* DNA polymerase then uses the first cDNA strand as a template for the synthesis of the second cDNA strand, thereby producing a population of dscDNA molecules from the original poly$(A)^+$ mRNA. After converting the 5' and 3' ends into blunt ends, the dscDNA can be ligated to linkers/adaptors and subsequently ligated into suitable vectors and transformed or packaged into a cell line, thereby forming the library.

According to a different method of synthesizing cDNA in vitro (Kato et al. *Gene* 25, 243–250 (1994)), full length poly$(A)^+$ mRNA is selected by treatment with bacterial alkaline phosphatase and tobacco acid pyrophosphatase, and the 5' end of the mRNA then ligated to a chimeric DNA-RNA linker containing a restriction site, e.g., EcoRI. The poly(A) 3' end of the mRNA is then hybridized to an oligo d(T) sequence of an open vector and the oligo d(T) used to prime cDNA synthesis. After the synthesis of the first strand of cDNA, the cDNA intermediate is digested with a restriction enzyme (e.g., EcoRI) and self-ligated. The second strand cDNA is synthesized using RNase H, *E. coli*-DNA polymerase I and *E. coli* DNA ligase. The obtained cDNA vectors are used to transform *E. coli.*

The library is then screened for cells transformed with nucleic acid encoding the desired polypeptide.

Typically, screening is carried out using either radiolabelled oligonucleotide probes that are complementary to a target sequence in the cDNA or by expressing and detecting the target polypeptide, e.g., using a labelled antibody that recognizes an epitope on the polypeptide. Alternatively, the library can be screened by hybridization with a nucleic acid probe.

Honjo et al. (U.S. Pat. No. 5,525,486) describe a different method for isolating polypeptides including a signal sequence from a cDNA library prepared in a conventional route. In this method, the cDNA is inserted into a vector upstream of a reporter gene that lacks a signal sequence. This means that cells transformed with the full length cDNA including the signal sequence of the target polypeptide will produce polypeptide fused to the reporter, which will be exported from the cells, allowing the library to be screened using a labelled antibody specific to the reporter. Thus, this approach can be used to clone polypeptides without first isolating the polypeptide in sufficient quantity to generate antibody for the screening step.

In yet another approach, Jacobs (U.S. Pat. No. 5,536,637) and Klein et al. , *Proc. Natl. Acad. Sci. USA* 93(14) 7108–7113 (1996), describe a method of screening a cDNA library for a secreted polypeptide by ligating the cDNA molecules in a cDNA library to a non-secreted yeast invertase gene. This nucleic acid is then transformed into yeast cells that do not contain the invertase gene and the cells grown in a medium containing sucrose or raffinose to produce the cDNA library. In this system, cells containing cDNA including the secretory leader sequence, or a sequence having the overall characteristics of the hydrophobic core of a signal sequence, will secrete invertase into the medium with the polypeptide where it can convert the sucrose or raffinose, providing an energy source for the yeast cells. Thus, the library can be screened for yeast cells transformed with cDNA comprising a signal sequence or a sequence encoding a hydrophobic sequence similar to a signal peptide, as these will be the only cells which grow on this medium.

While the general approaches described above have been used to successfully clone a large number of polypeptides, they do have certain disadvantages. The most basic step in constructing a cDNA library is the process of generating a double-stranded DNA copy of the mRNA. This can be accomplished by a number of different procedures, all of which involve the action of reverse transcriptase and oligonucleotide-primed synthesis of cDNA. An intrinsic problem in the construction of high quality full-length cDNA libraries is that, under in vitro conditions, the reverse transcriptase very often does not extend the first strand cDNA up to the ultimate 5' end of the mRNA, with the result that some mRNA sequences are not represented in the library. This is thought to occur due to hairpin formation in the mRNA leading to early termination in the conversion to cDNA. In addition, due to degradation during mRNA preparation procedures, some mRNAs do not contain the ultimate 5' ends and thus, even if the reverse transcriptase extends the first strand cDNA to the ultimate 5' end of a partially degraded mRNA molecule, the real 5' sequences are missing. This is especially a problem in the cloning of polypeptides having a signal sequence located at the 5' end of the gene, as these libraries are often screened by detecting polypeptide exported from the transformed cells. Thus, these methods require full-length cDNA, including the signal sequence.

Other disadvantages inherent in conventional methods of producing cDNA include the loss of mRNA sequences due to the RNase H activity of the reverse transcriptase degrading mRNA molecules and due to manipulations carried out at the 5' end of the mRNA, e.g., using S1 nuclease. In addition, the use of reverse transcriptase in vitro means that some of the enzymes or proteins present in the cell that normally repair nicks or correct mistakes during cDNA synthesis are not present when the cDNA is synthesized in vitro, leading to the loss of further mRNA sequences.

Accordingly, it is an object of the present invention to provide a method for producing double stranded cDNA (dscDNA) from mRNA. It is another object of the present invention to construct a high quality, normalized cDNA library of full-length secreted proteins and unsecreted proteins. It is a further object, to provide a method for screening a library thus created. It is yet another object of this invention to provide recombinant host cells transformed with vectors containing regions of single stranded mRNA sequences and a nucleic acid encoding a reverse transcriptase. These and further objects will be apparent from the following detailed description.

SUMMARY OF THE INVENTION

In one aspect, the present invention provides a method of producing double stranded cDNA (dscDNA) from mRNA comprising treating a cDNA cloning vector containing the mRNA with reverse transcriptase. According to a preferred embodiment, (a) the authentic 5' end of the mRNA molecules, defined as to have a so called cap structure (Gppp.triphosphate), is modified and ligated to an oligonucleotide cap; (b) a vector having a single stranded 5' overhang complementary to the oligonucleotide cap and single stranded 3' overhang complementary to the 3' end of the mRNA is used to capture the tagged mRNA so that both ends of the mRNA are annealed to the vector; and, (c) the mRNA is converted into dscDNA using reverse transcriptase.

Preferably, the mRNA is poly$(A)^+$ mRNA in which case the 3' poly(A) end can be captured by a vector having a 3' oligo d(T) overhang. More preferably, the mRNA is normalized. It is not absolutely necessary to isolated poly(A)+ mRNA; total RNA, which also includes poly$(A)^+$ mRNA, may be used, although its use is less preferred.

Thus, in this aspect, the present invention tags the mRNA molecules so that both ends of the mRNA can be annealed into a vector, and makes use of the property of reverse transcriptase that it can synthesize cDNA from a mRNA/DNA hybrid template by elongating the primer oligo d(T) annealed to the 3' terminus of the mRNA. According to the present invention, the conversion of the mRNA to dscDNA is performed in vivo, by transforming a cell that already expresses reverse transcriptase. It is also possible to partially or completely synthesize the first cDNA strand in vitro to stabilize the mRNA, transforming a reverse transcriptase producing cell line with this intermediate and complete the first cDNA strand in vivo. The second strand cDNA synthesis is initiated by the intrinsic RNase H activity of the reverse transcriptase and completed by the host cell's enzymes including DNA polymerases and DNA ligases. Any gaps, nicks, etc. will be corrected by the host upon replication initiation. It is also foreseen that a single host cell can be stably cotransfected with two separate vectors, one containing and capable of expressing DNA encoding reverse transcriptase and the other one containing the mRNA to be converted into dscDNA. In this case, the two vectors have different and compatible origins of replication and selection markers. In another embodiment, the coding sequence of reverse transcriptase and the mRNA will be present in the same vector.

In a further aspect, the present invention provides a method of constructing a cDNA library from a population of mRNA molecules by transforming reverse transcriptase-producing host cells with vectors containing the mRNA molecules so that the reverse transcriptase converts the mRNAs into dscDNA to form the cDNA library. In a preferred embodiment, this process comprises: (a) ligating the 5' end of the mRNA molecules to an oligonucleotide cap; (b) using a vector having a single stranded 5' overhang complementary to the oligonucleotide cap and single stranded 3' overhang complementary to the 3' end of the mRNA to capture the tagged mRNA so that both ends of the mRNA are annealed to the vector; and, (c) transforming a prokaryotic or eukaryotic cell containing the reverse transcriptase producing vector with the vectors so that the reverse transcriptase converts the mRNAs into dscDNA to form the cDNA library. This method also permits the type of variations detailed above in connection with the conversion of mRNA into dscDNA.

In another aspect, the present invention provides a method which comprises the screening of a cDNA library constructed from a population of poly$(A)^+$ mRNA molecules as described above, for target dscDNA or expression of a target polypeptide. Screening can be performed by any method known in the art, including those specifically mentioned hereinabove.

In yet another aspect, the present invention provides a recombinant host cell transformed with nucleic acid encoding reverse transcriptase and a vector comprising a single stranded mRNA sequence. In a preferred embodiment, the host cell is transformed with: (a) a first vector comprising a single stranded mRNA sequence, the mRNA sequence having a 5' oligonucleotide cap sequence which is complementary to a 5' overhang of the vector and a 3' sequence which is complementary to a 3' overhang of the vector, the overhangs and sequences annealing together to retain the mRNA sequence in the vector; and, (b) a second vector comprising nucleic acid encoding reverse transcriptase; wherein expression of the reverse transcriptase converts the mRNA into dscDNA.

The invention also concerns a novel reverse transcriptase disclosed herein.

Thus, the present invention is based on the recognition that modifying the mRNA so that it can be inserted into a vector provides a convenient way of priming it for cDNA synthesis. Further, in the aspects of the invention which use reverse transcriptase to convert mRNA to dscDNA in vivo provide a fast and clean way of synthesizing cDNA clones, compared to the prior art in vitro use of reverse transcriptase. In addition, cells transformed with the vectors conveniently provide other materials required for syntheses, such as ligases, nick repair enzymes, and single stranded binding proteins which help to relax hairpins in the mRNA, promoting full length cDNA synthesis.

BRIEF DESCRIPTION OF THE DRAWINGS

Embodiments of the present invention will now be further described by way of example with reference to the accompanying drawings in which:

FIGS. 1–5 show schematically the steps to produce a cDNA library using vector primed cDNA synthesis.

FIG. 1 illustrates the normalization of mRNA.

FIG. 2 shows the procedure of oligo capping of mRNA.

FIGS. 3A and 3B show the construction of a pRK5C-based cDNA cloning vector.

FIG. 4 illustrates the annealing of 5'-tagged mRNA to the cDNA cloning vector.

FIG. 5 shows the conversion of the mRNA into double stranded cDNA (dscDNA) using an *E. coli* host cell expressing Moloney murine leukemia virus reverse transcriptase and transformed with the mRNA/cDNA cloning vector.

FIG. 6 shows the restriction map of the plasmid pET21.tac.

FIGS. 7A–7E show the nucleotide sequence of the plasmid pET21.tac. (SEQ. ID. NO: 3) This includes the sequence of the BglII/XbaI fragment containing the PtacII promoter obtained from the plasmid Dsb1 (SEQ. ID. NO: 2—for the BglII/XbaI fragment). (Dsb1 is a derivative of the vector pACYC184) (Biolabs).

FIG. 8 shows the structure of the pACYC.tac vector prepared from pACYC184 (Biolabs).

FIGS. 9A–9D show the nucleotide sequence of the vector pACYC.tac (SEQ. ID. NO: 5).

FIG. 10 shows the structure of the plasmid pACYC.pol.

FIGS. 11A–11E show the nucleotide sequence of pACYC.pol (SEQ. ID. NO: 6).

FIGS. 12A–12D show the nucleotide sequence of the vector pRK5C (SEQ. ID. NO: 16).

FIGS. 13A–13I show the alignment of the nucleotide sequences of the vectors pRK5 (SEQ. ID. NO: 15) and pRK5C (SEQ. ID. NO: 16).

DETAILED DESCRIPTION OF THE INVENTION

Overview

As set out above, the present invention concerns the construction of a cDNA library in a eukaryotic or prokaryotic expression vector from which a cloned polypeptide encoded by the cDNA can be expressed. In the past, it has sometimes been difficult to obtain full-length cDNA libraries for the expression of secreted proteins as these usually have a signal peptide sequence located at the 5' end of the coding region. We realized that some of the reasons underlying this problem is degradation of the mRNA, thereby eliminating the 5' sequences from the usually captured 3' end, and that under in vitro conditions, the reverse transcriptase used to synthesize the cDNA from the mRNA template very often does not extend the first strand cDNA up to the ultimate 5' end of the mRNA due, for example, to hairpin formation. In addition, some mRNA sequences are lost because of the RNase H activity of reverse transcriptase and due to the manipulations carried out at the 5' end of the mRNA.

Accordingly, the present invention provides a method for the conversion of mRNA into dscDNA, by incorporating the single stranded mRNA molecules into a vector and using flanking double stranded sequence in the vector to prime cDNA synthesis. The cDNA synthesis can take place using reverse transcriptase in vitro, in vivo (e.g., in a prokaryotic or eukaryotic cell), or using a combination of these approaches. In a preferred embodiment, the vector including the mRNA sequence is transformed into a cell expressing reverse transcriptase, e.g., by being transformed by a second vector containing nucleic acid encoding the enzyme, so that the dscDNA synthesis is carried out under in vivo conditions in the cells. The mRNA may be poly(A)$^+$ mRNA or total RNA.

Detailed Description

The present invention concerns the most basic step in constructing a cDNA library, the process of generating a double-stranded DNA copy of the mRNA. Published procedures for performing this step might vary considerably. The conversion of mRNA into double-stranded cDNA involves the use of reverse transcriptase.

Methods for isolating RNA from eukaryotic and prokaryotic cells are well known in the art and are, for example, described in Ausubel et al., supra, Chapter 4. Poly(A)$^+$ mRNA, which is greatly enriched in mRNA can be separated from the remainder of total RNA, which is largely ribosomal RNA (rRNA) and transfer RNA (tRNA), for example, by binding to oligo(dT) cellulose (e.g., latex beads) while the remainder washes through. The poly(A)$^+$ mRNA can be eluted from the beads following known procedures, such as the protocol described in Ausubel et al., supra, Unit 4.5. Some other protocols use poly(U)Sephadex instead of oligo (dT). See, e.g. Moore and Sharp, *Cell* 36, 581–591 (1984). The poly(A)$^+$ mRNA starting material for the procedure may optionally be "normalized", i.e., highly abundant mRNAs will be deselected and low abundant mRNAs will be enriched, increasing the relative representation and facilitating the detection of the low abundant species in the cDNA library. Typically, normalization is carried out prior to tagging and comprises the following steps:

(i) binding the poly(A)$^+$ mRNAs to oligo d(T) coated substrate;

(ii) synthesizing all or part of a cDNA strands that are complementary to the mRNA;

(iii) denaturing the cDNA and mRNA strands;

(iv) annealing the mRNAs to the substrate bound cDNAs under conditions such that high abundant mRNAs anneal to the substrate bound cDNAs and low abundant mRNAs do not anneal; and, (v) collecting a fraction containing the low abundant mRNAs.

These steps may be repeated until the desired level of normalization is achieved in the population of mRNAs.

After this step, a combination of enzymes are used to select full length poly(A)$^+$ mRNA and tag their ultimate 5' ends. Starting from a population of poly(A)$^+$ mRNAs including sequences that are not full length, a phosphatase (such as HK thermolabile phosphatase) can be used to remove the phosphate moiety from mRNAs that are not full length, leaving 5'-OH ends at those mRNAs. Full length poly(A)$^+$ mRNAs are protected due to the Gppp cap. Tobacco Acid Pyrophosphatase is then used to digest the Gppp cap, leaving a 5' phosphate moiety at the 5' end of the full length mRNA. T4 RNA ligase is then used to tag the full length poly(A)$^+$ mRNAs at their 5' ends with "oligo-caps". The oligo caps have a 3'-OH end and thus can be ligated only to poly(A)$^+$ mRNAs displaying a 5' phosphate moiety. Thus, at the end of this procedure, the full-length mRNAs are tagged at the 5' end by an oligonucleotide and naturally at the 3' end by poly(A). Conveniently, the oligonucleotide cap is an RNA oligonucleotide, made by in vitro transcription or made by using an oligonucleotide synthesizer, or a hybrid RNA/DNA oligonucleotide made in an oligonucleotide synthesizer. Advantageously, a restriction site can be engineered into the oligonucleotide cap to allow the dscDNA produced in this method to be excised from the vector and manipulated, for example by being inserted into an expression system to express the encoded protein. In this event, a rare cutter site (such as SacI or XcmI, etc.) is preferably used. The oligonucleotide cap or the flanking sequence of the vector can also be engineered to include other sequences.

At the end of these procedures, the full length mRNA, tagged at its 3' end with the poly(A) tail and at its 5' end with an oligonucleotide cap can be captured by a suitable compatible cloning vector, the vector having an oligo-d(T) 3' overhang and an oligonucleotide 5' overhang complementary to the 5' end of the modified mRNA. In order to avoid the ends of the vector self annealing, the 5' and 3' ends are preferably non-complementary, and should not have significant self-complementarity, thus avoiding, e.g. hairpin formation. When the mRNA is captured by the vector, the vector will have a single stranded mRNA section, primed for cDNA synthesis. As mentioned above, the conversion of the mRNA to dscDNA can be carried out in vitro, using commercially available reverse transcriptase, in vivo, by transforming the vectors into a cell or cell line that expresses reverse transcriptase, or using a combination of these approaches.

In a preferred embodiment, cDNA synthesis is carried out by transforming the primed vectors into a suitable cell or cell line that produces reverse transcriptase. Conveniently, the reverse transcriptase is encoded by nucleic acid contained in a second vector transformed into the cell or cell line. Although the mRNA and the nucleic acid encoding revers transcriptase can be transformed into the host cells simultaneously (cotransformation) or in either order, preferably, the production of reverse transcriptase is induced prior to transformation with the mRNA containing vector. As a step in the dscDNA synthesis involves the degradation of the mRNA strand, conveniently the reverse transcriptase expressed in the cell or cell line also has RNase H activity. The reverse transcriptase then extends the 3' overhang (d(T)) in the vectors to produce the first cDNA strand, and then degrades the RNA in the resulting RNA/DNA intermediate. Host cell enzymes, e.g. DNA polymerases, DNA ligases, etc. synthesize the second cDNA strand using the first cDNA strand as a template.

Thus, in a preferred embodiment, the mRNA vector containing the single stranded mRNA captured by its tags is transformed directly into *E. coli* (or another prokaryotic or eukaryotic host cell) which contains an expression plasmid for Moloney murine leukemia virus reverse transcriptase. Under the in vivo conditions, the mRNA is then converted into dscDNA by the reverse transcriptase in the cells. In one embodiment, the reverse transcriptase used is the M-MuLV reverse transcriptase described in Tanese et al., supra, or a M-MuLV which is first described in the present application. In this method, other enzymes required for the conversion process, such as DNA polymerases and DNA ligase, are conveniently provided by the cell into which the hybrid vector has been transformed (eg, *E. coli*) . The use of in vivo conditions to convert the mRNA captured in the first vector into dscDNA has the advantage of increasing the fidelity of cDNA production by reverse transcriptase, which has a lower error rate when used in vivo as compared to in vitro. Further, under in vivo conditions, the method can take advantage of the mechanisms present in the cell to ameliorate hairpin production (eg, single stranded binding proteins) thereby helping to improve the yield of full length cDNA. Nicks and gaps are "repaired" during replication of the plasmid.

It is also possible to insert the mRNA and the coding sequence of reverse transcriptase in the same vector, which is then used to transform a suitable recombinant host cell.

Although this step will be illustrated by using *E. coli* as a host, other prokaryotic or eukaryotic host cells are also suitable for converting mRNA into dscDNA according to the present invention. Such host cells are, for example, disclosed in U.S. Pat. No. 5,108,901 issued Apr. 28 1992, and in PCT Publication No. WO95/33051. Suitable prokaryotes include gram negative or gram positive organisms, for example *E. coli* or *bacilli*. A preferred cloning host is *E. coli* 294 (ATCC 31,446) although other gram negative or gram positive prokaryotes such as *E. coli B, E. coli x* 1776 (ATCC 31,537), *E. coli W*3110 (ATCC 27,325), Pseudomonas species, or Serratia Marcesans are suitable. In addition to prokaryotes, eukaryotic microbes such as filamentous fungi and yeasts are suitable hosts for appropriate vectors of the invention. *Saccharomyces cerevisiae,* or common baker's yeast, is the most commonly used among lower eukaryotic host microorganisms. However, a number of other genera, species and strains are commonly available and useful herein, such as those disclosed in the above-cited patent and patent applications. A preferred yeast strain for the present invention is *Saccharomyces cerevisiae HF*7*c* (CLONTECH). Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plant and insect cells, see, e.g. Luckow et al., *Bio/Technology* 6, 47–55 (1988); Miller et al. in: *Genetic Engineering,* Setlow et al., eds., Vol. 8 (Plenum Publishing, 1986), pp. 277–279; and Maeda et al., *Nature* 315, 592–594 (1985). Interest has been greatest in vertebrate cells, and propagation of vertebrate cells in culture (tissue culture) is per se known. See, *Tissue Culture,* Academic Press, Kruse and Patterson, eds. (1973). Examples of useful mammalian host cell lines are monkey kidney CV1 line transformed by SV40 (COS-7, ATCC CRL 1651); human embryonic kidney cell line (293 or 293 cells subcloned for growth in suspension culture, Graham et al., *J. Gen. Virol.* 36, 59 [1977]); baby hamster kidney cells 9BHK, (ATCC CCL 10); Chinese hamster ovary cells/-DHFR (CHO, Urlaub and Chasin, *Proc. Natl. Acad. Sci. USA* 77, 4216 [1980]); mouse sertolli cells (TM4, Mather, *Biol. Reprod.* 23, 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep. G2, HB 8065); mouse mammary tumor (MMT 060562, ATCC CCL51); TRI cells (Mather et al., *Annals N.Y. Acad. Sci.* 383, 44068 [1982]); MRC 5 cells; FS4 cells; and a human hepatoma cell line (Hep G2). Preferred host cells are human embryonic kidney 293 and Chinese hamster ovary cells.

Once the cDNA library has been constructed as described above it can be screened by conventional methods designed to quickly determine whether a particular clone contains the desired nucleic acid sequence. In general, bacteriophage, cosmid or plasmid libraries are usually screened by hybridization to nick-translated DNA and synthetic oligonucleotides, or using immunoreactivity-based assays, or by hybrid selection of mRNA and translation. Libraries are usually spread out on agarose plates, transferred to nitrocellulose filters and hybridized to labelled oligonucleotide probes complementary to a target sequence in the cDNA, or the target polypeptides are expressed and bound to labelled antibodies which recognize an epitope on a target polypeptide. In both instances, preferably the label is radioactive (e.g., $^{32}P$), fluorescent, or biotin. Such screening techniques are described, for example, in Chapter 6 of Ausubel et al., supra. Alternatively, other known screening approaches such as the methods described in Honjo et al., supra or Jacobs, supra, can be used. When clones containing cDNA encoding the target polypeptide have been found, the cDNA can be readily isolated for larger scale expression, eg, by cutting the cDNA from the vector and amplifying it using PCR. This step can be facilitated where restriction sites have been engineered in the cDNA sequence corresponding to the oligonucleotide cap or in the flanking sequence of the vector.

In the following Examples, the steps mentioned above will be described in detail with reference to the schematic drawings shown in the Figures. Modifications to the steps described below and the materials and methods used will be readily apparent to the skilled person and are within the scope of the present invention. In particular, while the protocol below is described uses poly(A)$^+$ mRNA, it could be readily adapted to use other types of RNA, eg hnRNA.

EXAMPLE 1

Normalization of mRNA

Normalization is depicted in FIG. 1 and is an optional step to be used when the abundance of the target mRNA is low, enriching the abundance of low abundant mRNA species as compared to more highly abundant ones. The subtraction protocol detailed below can be repeated as necessary.

Poly(A)$^+$ mRNA is directly isolated from either tissue or cells (e.g., white blood cells) by binding the mRNA to commercially available oligo d(T) latex beads or similar material. In the normalization process, the oligo d(T) serves as a primer for first strand cDNA synthesis. As the first strand cDNA needs to serve only as a hybridization tag later in the procedure, in this instance, it does not matter if the reverse transcriptase does not synthesize full length cDNA.

The RNA/DNA hybrid thus produced is then heat denatured and a hybridization reaction carried out in which between the mRNAs and the cDNA fragments. In this reaction, highly abundant mRNAs will hybridize to the first strand cDNA faster than low abundant mRNAs, with the population of mRNA species obtained being controlled by the annealing time and conditions. Either incubation temperature can be adjusted, or the RNA homopolymer poly(A) can be added to prevent hybridization to the oligo d(T) beads. The highly abundant mRNAs can then be separated from the low abundant species by centrifugation as the highly abundant mRNAs will spin down as they are hybridized to the latex beads. The low abundance species can then be recovered from the supernatant. The whole subtraction procedure can be repeated as many times as necessary to obtain the desired enrichment.

EXAMPLE 2

Oligonucleotide Capping of mRNA

This step is depicted in FIG. 2 and uses either the normalized mRNA from the step above or poly(A)$^+$ mRNA directly (i.e., no normalization) and serves to select full length capped mRNAs and modify their 5' ends so that they are capped by an oligonucleotide and can be captured by the vector having a complementary 5' overhang sequence.

In the first step, poly(A)$^+$ mRNA is dephosphorylated using a phosphatase to remove the 5' phosphates of uncapped RNAs, but not full length capped mRNAs, leaving a hydroxyl group on their 5' ends. The phosphatase could be either HK thermolabile phosphatase, which has the advantage that it can be inactivated, or bacterial alkaline phosphatase (BAP).

Next, tobacco acid pyrophosphatase removes the cap structure from full length mRNAs, leaving them with a 5' phosphate group. T4 RNA ligase is then used to ligate a ribo-oligonucleotide or a DNA/RNA hybrid oligonucleotide to the 5' end of the full length mRNAs which have a phosphate group and can act as donors for the 3' OH group of the oligonucleotide. T4 RNA ligase, the product of the phage gene 63, has been purified from phage-infected cells. It catalyzes the ATP-dependent covalent joining of single-stranded 5'-phosphoryl termini of DNA or RNA to single-stranded 3'hydroxyl termini of DNA or RNA. Reaction conditions for performing the annealing are described, for example, in Ausubel et al., supra, Unit 3.15. According to Uhlenbech and Gumport, *The Enzymes* 15, 31–58 (1982), T4 RNA ligase accepts a hybrid oligonucleotide as an acceptor, if at least two or three subsites of the acceptor are ribonucleotides, the preferred nucleotide being A. As mRNAs which are uncapped or short will have 5'-OH groups they will not be tagged with the oligonucleotide, having a 3'-OH. The sequence of the DNA part of the oligonucleotide can either be chosen at random or engineered in some way, e.g., to contain a rare cutter restriction site or engineered to contain e.g. promoter sequences for e.g. SP6 T3, T7 RNA polymerases. Upon the final subcloning of the resulting dscDNA fragments into any vector the constructs can be used to generate RNA in vitro which subsequently can be used for translation and protein analysis. In addition, the 5' oligonucleotide tag can serve as a target sequence suitable for 5' RACE technology. Using this sequence, the ultimate 5' end of the full-length mRNA can be characterized. The oligonucleotides can be synthesized using standard phosphoramidite chemistry on an e.g. Perkin-ELMER (ABI) 394 DNA/RNA synthesizer.

The addition of the oligonucleotide tag has the further advantage that it opens up the possibility of using the tagged mRNA as a substrate for in vitro full length cDNA synthesis. This is possible because of the 5' tag attached to the mRNA, which, after completing the first cDNA strand, is also transcribed into cDNA. After degradation of the mRNA in the resulting RNA/DNA hybrid by either RNase H, alkali treatment or heat denaturation, an oligonucleotide complementary to the oligo cap, can be annealed to it and be used as a primer for the second strand cDNA synthesis.

EXAMPLE 3

Construction of a cDNA Cloning Vector pRK5C

The construction of a pRK5C-based cloning vector is shown in FIGS. 3A and 3B. A vector adapted to capture oligonucleotide tagged, full length mRNAs was prepared from vector pRK5C (a derivative of pRK5 described in EP 307,247 published Mar. 15 1989—SEQ. ID. NO: 15). The complete nucleotide sequence of pRK5C is shown in FIGS. 12A–12D (SEQ. ID. NO: 16). As apparent from the alignment in FIGS. 13A–13I, the main difference between pRK5 and pRK5C is the insertion of a staffer fragment after nucleotide position 941 of pRK5. Vector pRK5C was chosen as a starting vector because of this stuffer fragment which can be released by digestion with BstXI, generating non compatible 3' overhanging ends as the BstXI sites flanking the stuffer fragment have different sequences. It is noted, however, that a variety of other cloning vectors, such as the multifunctional shuttle vector pKA1 described by Kato et al., supra, would be similarly suitable for the purposes of the present invention.

After purification of the BstXI digested vector fragment, a BstXI adapter/oligo d(T) oligonucleotide was ligated to the BstXI generated 3' oligo d(T) overhang on the plasmid. As some of the adapter oligonucleotide will become ligated to the 5' overhang of the vector, digestion with BamHI was then used to get rid of the end portion of the 5' overhang, forming a new overhang. The 3' end was unaffected by digestion with BamHI, see the restriction map. The BamHI site was then used to ligate a BamHI adapter oligonucleotide that forms a 5' overhang. Both of the adapter oligonucleotides were then engineered to include a convenient restriction site, preferably a rare, unique restriction site such as I-CeuI or XcmI, to facilitate the recovery of cDNA fragments from the vector synthesized using mRNAs ligated into the vector. Finally, the vector containing a 3' oligo d(T) overhang and a 5' tag overhang was gel purified. The overhangs and adjacent portions of the vector were then sequenced which confirmed that the adaptors had been inserted in the correct orientation, and were of correct sequence.

The above protocol could be modified in several ways to produce similar vectors. For example, the 3' oligo (d)T overhang could be added using terminal transferase. Terminal transferase is a template-independent DNA polymerase which catalyzes the incorporation of deoxynucleotides to the 3'-hydroxyl termini of DNA accompanied by the release of inorganic phosphatase. The reaction conditions for performing this reaction are described in standard textbooks of recombinant DNA technology, such as, for example, in Ausubel et al., supra, Unit 3.6. The 5' overhang could be added using exonuclease III (ExoIII), an enzyme which has several known activities, including double-strand specific 3' to 5' exonuclease activity. Using exonuclease III to modify the 5' end of the vector results in an overhang (similar to the one shown in FIG. 3/2) to which the tagged mRNA can be annealed.

EXAMPLE 4

Annealing the 5' tagged mRNA to the cDNA cloning vector

This step is illustrated in FIG. 4. The 5' tagged mRNA obtained in Example 2 is annealed to the cDNA cloning vector constructed as described Example 3, taking advantage of the complementarity of the respective overhangs attached to the mRNA sequence and the cloning vector. The 5' nick is then closed by T4 DNA ligase. T4 DNA ligase, the product of gene 30 of phage T4, was originally purified from phase-infected cells of *E. coli*. The phage T4 gene 30 has been cloned, and the enzyme is now prepared from overproducing strains. Using ATP as a cofactor, T4 ligase catalyzed the repair of single-stranded nicks in Duplex DNA and joins duplex DNA restriction fragments having either blunt or cohesive ends. A detailed ligation protocol is described, for example, in Ausubel et al., supra, Unit 3.14. The result of this step is a closed cDNA cloning vector, comprising a single-stranded region corresponding to the mRNA.

EXAMPLE 5

Construction of Reverse Transcriptase Producing Vector pACYC.pol

The following protocol describes the construction of a reverse transcriptase expressing plasmid (pACYC.pol) suitable for use in *E. coli*.

A plasmid providing the reverse transcriptase in *E. coli*, needs to be maintained in *E. coli* together with the cDNA/mRNA cloning construct. Therefore, the two plasmids need to carry different origins of replication. The pRK5C vector described above as the mRNA capture vector is a derivative of pBR322, and so contains the Col E1 origin of replication and the ampicillin resistance gene. Thus, the other plasmid could carry a different origin of replication, such as p15A, and another selectable marker, such as the chloramphenicol resistance gene (Cm) , each of which can be obtained, for example, from the commercially available plasmid pACYC184 (Biolabs).

In order to construct pACYC.pol several intermediate cloning steps were employed. The following protocol describes the cloning steps to produce this vector. However, the skilled person could readily adapt the procedure described below to produce a functionally equivalent construct.

The starting plasmid used was pET21a (Novagen, Madison, Wis., Catalog Number: 69740-1). This plasmid, the reverse complement sequence of which is shown in SEQ. ID. NO: 1, has a T7 RNA polymerase promoter, a T7 transcriptional terminator, amp/ColE1/ROP, a $lac^I$ gene, polylinkers to insert foreign genes to be expressed, allowing N- and C-terminal fusions to be produced. In pET21a, the T7 RNA polymerase promoter and lac operator reside on a small BglII/XbaI fragment. This fragment was excised and replaced by a promoter fragment containing the $tac_{II}$ promoter (PtacII, de Boer et al, PNAS, 80, 21–25, (1983)). The fragment containing the $tac_{II}$ promoter and the lac operator sequence was generated by PCR using the plasmid Dsb1 (a derivative of the original vector pACYC184, SEQ. ID. NO: 4, GenBank, containing an unrelated insert provided by Daniel Yansura), and oligonucleotide primers #RS 103 and #RS 104, containing BglII and XbaI restriction sites, respectively.

#RS 103: 5'-GGAAGATCTCGACTGCACGGTGCACCA ATGCTTC-3' (SEQ. ID. NO: 9)

#RS 104: 5'-AGGTCTAGAGGGGAATTGTTATCCGC TCACAATTCCACAC-3' (SEQ. ID. NO: 10)

The sequence of the BglII/XbaI fragment containing the PtacII promoter obtained from the plasmid Dsb1 is shown in SEQ. ID. NO: 2.

After digestion of the PCR fragment with BqlII/XbaI, the resultant fragment was cloned into BqlII/XbaI digested pET21a (Novagen), thereby replacing the T7 RNA polymerase promoter to produce plasmid pET21.tac. The restriction map of this plasmid is shown in FIG. 6. The complete nucleotide sequence of plasmid pET21.tac is shown in FIGS. 7A–7E (SEQ. ID. NO: 3). This plasmid allows the expression of any foreign protein under e.g., IPTG induced conditions and is independent of the host. The T7 RNA polymerase promoter required a host to provide the enzyme T7 RNA polymerase.

In the next step, a ClaI/XmaI PCR fragment containing the $Ptac_{II}$ promoter, the lac operator, the transcription terminator, and the $lac^I$ gene was amplified from pET21.tac using PCR and transferred into pACYC184 (Biolabs). pACYC184 is a small, low copy *E. coli* cloning vector that is 4,244 base pairs in length (GenBank Accession #X06403—SEQ. ID. NO: 4). It carries a p15A origin of replication, which enables it to coexist with pBR322-based vectors, chloramphenicol (Cm) and tetracycline (Tet) resistance genes, a unique ClaI site within Tet promoter region and several NaeI/NgoMI sites which take out the complete Tet gene and flanking sequence at its 3' end. The PCR fragment was generated using the oligonucleotides #RS105 and #RS106.

#RS105: 5'-GAATCCCGGGGCCTAATGAGTGAGCTAACTTAC-3' (SEQ. ID NO: 11)

#RS 106: 5'-AGGATCGATATAGTTCCTCCTTTCAGCAAAAAACCCC-3' (SEQ. ID. NO: 12)

The PCR fragment was inserted into the ClaI/NgoMI (NaeI) sites of pACYC184. The resultant plasmid was pACYC.tac (FIGS. 9A–9D, SEQ. ID. NO: 5).

In the following step, a PCR product encoding Moloney murine leukemia virus reverse transcriptase, was transferred into a multiple cloning site of pACYC.tac. The PCR fragment was generated using the oligonucleotides #RS 107 (containing an NdeI restriction site) and #RS 108 (containing BssHII/SacI sites).

#RS 107: 5'GAACATATGACTTTGAATATCGAAGATGAGCATCGTCTGCATGAGACCTCAAAAGAGC C-3' (SEQ. ID. NO: 13)

#RS 108: 5'TTTTGAGCTCTTAAGTCTCTGTGATGGCTGCCTTGCGCGCCGCTTGGTCAGCCATCC-3' (SEQ. ID. NO: 14)

Mink lung cells infected with X-MuLV (X-MuLV E.10) were obtained from Christos Petropoulos. In order to extract DNA from those cells, cells were washed with PBS, and resuspended in a solution containing 50 mM Tris (pH 8.0), 10 mM EDTA, 100 mM NaCl, 1% SDS and 100 μg/ml proteinase K (65° C.) . This was followed by the addition of 0.3M NaAC, extraction with 2× phenol, 1× chloroform, and 1× $CHCl_3$, and ethanol precipitation. The precipitated DNA was rinsed in 80% ethanol and resuspended in 10/0.1 TE. The DNA extracted from the cells, was used as a template in the PCR reaction. The resulting PCR fragment was digested with NdeI and SacI and subcloned into NdeI/SacI cut pACYC.tac vector, to yield plasmid pACYC.pol (FIG. 10), the sequence of which is shown in FIGS. 11A–11E (SEQ. ID. NO: 6). A restriction analysis was then performed which confirmed that the plasmid contained the fragments of the expected size. In addition, the fragment containing the M-MuLV pol gene was sequenced and was found to contain over 100 (128)point mutations as compared to the corresponding part of the sequence published in Tanese et al. (SEQ. ID. NO: 7, Dayhoff data base). While most of these mutations were in the third codon position, this still led to 14 amino acid mutations. The protein sequence of the XENOTROPIC Moloney Murine leukemia virus reverse transcriptase (xM-MuLV) of the present invention, as deduced from the sequence of the pACYC.pol gene is shown in SEQ. ID. NO: 8.

Vector pACYC.pol was then transformed into a range of *E. coli* strains to establish that production of enzymatically active reverse transcriptase could be induced. These experiments checked the production of an approximately 70 kD protein (based on the predicted size of xM-MuLV; 665 aa–MW 73942.34) at various time points after induction by IPTG. The expression was analyzed by SDS-PAGE (7.8%). The experiments confirmed that in *E. coli* strains HB101, DH10B, HMS174(DE3), BL21, XL1 Blue, *E. coli* SURE, and DH5α, a~70 kD protein was induced after IPTG administration. This corresponds to the approximate molecular weight expected by the coding capacity of the subcloned fragment encoding the reverse transcriptase from xenotropic murine leukemia virus. This protein was also the major protein component produced in all the tested strains, indicating that this is an efficient way of producing reverse transcriptase, either commercially or in the protocols described here. The gels did not indicate many major breakdown products, although some strains did show an induced band at ~50 kD which could be related to the reverse transcriptase.

The fact that induction of the pol gene worked in the strains which do not include an inducible RNA polymerase and/or lacI repressor indicates that the pol gene can be expressed in virtually every *E. coli* strain. This means that, subject to the requirement of having a different origin of replication mentioned above, all of these strains are potential recipients of mRNA/cDNA cloning vector.

The enzymatic activity of the reverse transcriptase produced in these experiments is then determined.

EXAMPLE 5

Transformation of Cell Lines with pACYC.pol and pRK5C

In order to confirm that the pRK5C and pACYC.pol vector could be stably maintained in the same cell without recombination or rearrangement, electrocompetent cells of *E. coli* strain XL1 Blue was transformed with both constructs and cells grown up for 24 hours. DNA was then isolated from the cells, digested using HincII and ApoI and subjected to gel electrophoresis. The pattern of fragments produced confirmed that both plasmids were stably maintained in the cell and had not rearranged or recombined.

*E. coli* cells (e.g., XL1 Blue), transformed with pACYC.pol, were used to prepare transformation competent cells according to standard procedures. Prior to long term storage, the cells were treated with IPTG to induce expression of the xM-MuLV reverse transcriptase. Induction of xM-MuLV reverse transcriptase was analyzed as described before. Expression of xM-MuLV reverse transcriptase was evident.

The foregoing examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are hereby expressly incorporated by reference.

---

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 5443 base pairs
( B ) TYPE: Nucleic Acid
( C ) STRANDEDNESS: Single -continued ( D ) TOPOLOGY: Linear ( x i ) SEQUENCE DESCRIPTION: SEQ ID NO:1:

```
TGGCGAATGG GACGCGCCCT GTAGCGGCGC ATTAAGCGCG GCGGGTGTGG     50
TGGTTACGCG CAGCGTGACC GCTACACTTG CCAGCGCCCT AGCGCCCGCT    100
CCTTTCGCTT TCTTCCCTTC CTTTCTCGCC ACGTTCGCCG GCTTTCCCCG    150
TCAAGCTCTA AATCGGGGGC TCCCTTTAGG GTTCCGATTT AGTGCTTTAC    200
GGCACCTCGA CCCCAAAAAA CTTGATTAGG GTGATGGTTC ACGTAGTGGG    250
CCATCGCCCT GATAGACGGT TTTTCGCCCT TTGACGTTGG AGTCCACGTT    300
CTTTAATAGT GGACTCTTGT TCCAAACTGG AACAACACTC AACCCTATCT    350
CGGTCTATTC TTTTGATTTA TAAGGGATTT TGCCGATTTC GGCCTATTGG    400
TTAAAAAATG AGCTGATTTA ACAAAAATTT AACGCGAATT TTAACAAAAT    450
ATTAACGTTT ACAATTTCAG GTGGCACTTT TCGGGGAAAT GTGCGCGGAA    500
CCCCTATTTG TTTATTTTTC TAAATACATT CAAATATGTA TCCGCTCATG    550
AGACAATAAC CCTGATAAAT GCTTCAATAA TATTGAAAAA GGAAGAGTAT    600
GAGTATTCAA CATTTCCGTG TCGCCCTTAT TCCCTTTTTT GCGGCATTTT    650
GCCTTCCTGT TTTTGCTCAC CCAGAAACGC TGGTGAAAGT AAAAGATGCT    700
GAAGATCAGT TGGGTGCACG AGTGGGTTAC ATCGAACTGG ATCTCAACAG    750
CGGTAAGATC CTTGAGAGTT TTCGCCCCGA AGAACGTTTT CCAATGATGA    800
GCACTTTTAA AGTTCTGCTA TGTGGCGCGG TATTATCCCG TATTGACGCC    850
GGGCAAGAGC AACTCGGTCG CCGCATACAC TATTCTCAGA ATGACTTGGT    900
TGAGTACTCA CCAGTCACAG AAAAGCATCT TACGGATGGC ATGACAGTAA    950
GAGAATTATG CAGTGCTGCC ATAACCATGA GTGATAACAC TGCGGCCAAC   1000
TTACTTCTGA CAACGATCGG AGGACCGAAG GAGCTAACCG CTTTTTTGCA   1050
CAACATGGGG GATCATGTAA CTCGCCTTGA TCGTTGGGAA CCGGAGCTGA   1100
ATGAAGCCAT ACCAAACGAC GAGCGTGACA CCACGATGCC TGCAGCAATG   1150
GCAACAACGT TGCGCAAACT ATTAACTGGC GAACTACTTA CTCTAGCTTC   1200
CCGGCAACAA TTAATAGACT GGATGGAGGC GGATAAAGTT GCAGGACCAC   1250
TTCTGCGCTC GGCCCTTCCG GCTGGCTGGT TTATTGCTGA TAAATCTGGA   1300
GCCGGTGAGC GTGGGTCTCG CGGTATCATT GCAGCACTGG GGCCAGATGG   1350
TAAGCCCTCC CGTATCGTAG TTATCTACAC GACGGGGAGT CAGGCAACTA   1400
TGGATGAACG AAATAGACAG ATCGCTGAGA TAGGTGCCTC ACTGATTAAG   1450
CATTGGTAAC TGTCAGACCA AGTTTACTCA TATATACTTT AGATTGATTT   1500
AAAACTTCAT TTTTAATTTA AAAGGATCTA GGTGAAGATC CTTTTTGATA   1550
ATCTCATGAC CAAAATCCCT TAACGTGAGT TTTCGTTCCA CTGAGCGTCA   1600
GACCCCGTAG AAAAGATCAA AGGATCTTCT TGAGATCCTT TTTTTCTGCG   1650
CGTAATCTGC TGCTTGCAAA CAAAAAAACC ACCGCTACCA GCGGTGGTTT   1700
GTTTGCCGGA TCAAGAGCTA CCAACTCTTT TTCCGAAGGT AACTGGCTTC   1750
AGCAGAGCGC AGATACCAAA TACTGTCCTT CTAGTGTAGC CGTAGTTAGG   1800
CCACCACTTC AAGAACTCTG TAGCACCGCC TACATACCTC GCTCTGCTAA   1850
TCCTGTTACC AGTGGCTGCT GCCAGTGGCG ATAAGTCGTG TCTTACCGGG   1900
```

-continued

| | | | | | |
|---|---|---|---|---|---|
| TTGGACTCAA | GACGATAGTT | ACCGGATAAG | GCGCAGCGGT | CGGGCTGAAC | 1950 |
| GGGGGGTTCG | TGCACACAGC | CCAGCTTGGA | GCGAACGACC | TACACCGAAC | 2000 |
| TGAGATACCT | ACAGCGTGAG | CTATGAGAAA | GCGCCACGCT | TCCCGAAGGG | 2050 |
| AGAAAGGCGG | ACAGGTATCC | GGTAAGCGGC | AGGGTCGGAA | CAGGAGAGCG | 2100 |
| CACGAGGGAG | CTTCCAGGGG | GAAACGCCTG | GTATCTTTAT | AGTCCTGTCG | 2150 |
| GGTTTCGCCA | CCTCTGACTT | GAGCGTCGAT | TTTTGTGATG | CTCGTCAGGG | 2200 |
| GGGCGGAGCC | TATGGAAAAA | CGCCAGCAAC | GCGGCCTTTT | TACGGTTCCT | 2250 |
| GGCCTTTTGC | TGGCCTTTTG | CTCACATGTT | CTTTCCTGCG | TTATCCCCTG | 2300 |
| ATTCTGTGGA | TAACCGTATT | ACCGCCTTTG | AGTGAGCTGA | TACCGCTCGC | 2350 |
| CGCAGCCGAA | CGACCGAGCG | CAGCGAGTCA | GTGAGCGAGG | AAGCGGAAGA | 2400 |
| GCGCCTGATG | CGGTATTTTC | TCCTTACGCA | TCTGTGCGGT | ATTTCACACC | 2450 |
| GCATATATGG | TGCACTCTCA | GTACAATCTG | CTCTGATGCC | GCATAGTTAA | 2500 |
| GCCAGTATAC | ACTCCGCTAT | CGCTACGTGA | CTGGGTCATG | GCTGCGCCCC | 2550 |
| GACACCCGCC | AACACCCGCT | GACGCGCCCT | GACGGGCTTG | TCTGCTCCCG | 2600 |
| GCATCCGCTT | ACAGACAAGC | TGTGACCGTC | TCCGGGAGCT | GCATGTGTCA | 2650 |
| GAGGTTTTCA | CCGTCATCAC | CGAAACGCGC | GAGGCAGCTG | CGGTAAAGCT | 2700 |
| CATCAGCGTG | GTCGTGAAGC | GATTCACAGA | TGTCTGCCTG | TTCATCCGCG | 2750 |
| TCCAGCTCGT | TGAGTTTCTC | CAGAAGCGTT | AATGTCTGGC | TTCTGATAAA | 2800 |
| GCGGGCCATG | TTAAGGGCGG | TTTTTTCCTG | TTTGGTCACT | GATGCCTCCG | 2850 |
| TGTAAGGGGG | ATTTCTGTTC | ATGGGGGTAA | TGATACCGAT | GAAACGAGAG | 2900 |
| AGGATGCTCA | CGATACGGGT | TACTGATGAT | GAACATGCCC | GGTTACTGGA | 2950 |
| ACGTTGTGAG | GGTAAACAAC | TGGCGGTATG | GATGCGGCGG | GACCAGAGAA | 3000 |
| AAATCACTCA | GGGTCAATGC | CAGCGCTTCG | TTAATACAGA | TGTAGGTGTT | 3050 |
| CCACAGGGTA | GCCAGCAGCA | TCCTGCGATG | CAGATCCGGA | ACATAATGGT | 3100 |
| GCAGGGCGCT | GACTTCCGCG | TTTCCAGACT | TTACGAAACA | CGGAAACCGA | 3150 |
| AGACCATTCA | TGTTGTTGCT | CAGGTCGCAG | ACGTTTTGCA | GCAGCAGTCG | 3200 |
| CTTCACGTTC | GCTCGCGTAT | CGGTGATTCA | TTCTGCTAAC | CAGTAAGGCA | 3250 |
| ACCCCGCCAG | CCTAGCCGGG | TCCTCAACGA | CAGGAGCACG | ATCATGCGCA | 3300 |
| CCCGTGGGGC | CGCCATGCCG | GCGATAATGG | CCTGCTTCTC | GCCGAAACGT | 3350 |
| TTGGTGGCGG | GACCAGTGAC | GAAGGCTTGA | GCGAGGGCGT | GCAAGATTCC | 3400 |
| GAATACCGCA | AGCGACAGGC | CGATCATCGT | CGCGCTCCAG | CGAAAGCGGT | 3450 |
| CCTCGCCGAA | AATGACCCAG | AGCGCTGCCG | GCACCTGTCC | TACGAGTTGC | 3500 |
| ATGATAAAGA | AGACAGTCAT | AAGTGCGGCG | ACGATAGTCA | TGCCCCGCGC | 3550 |
| CCACCGGAAG | GAGCTGACTG | GGTTGAAGGC | TCTCAAGGGC | ATCGGTCGAG | 3600 |
| ATCCCGGTGC | CTAATGAGTG | AGCTAACTTA | CATTAATTGC | GTTGCGCTCA | 3650 |
| CTGCCCGCTT | TCCAGTCGGG | AAACCTGTCG | TGCCAGCTGC | ATTAATGAAT | 3700 |
| CGGCCAACGC | GCGGGGAGAG | GCGGTTTGCG | TATTGGGCGC | CAGGGTGGTT | 3750 |
| TTTCTTTTCA | CCAGTGAGAC | GGGCAACAGC | TGATTGCCCT | TCACCGCCTG | 3800 |
| GCCCTGAGAG | AGTTGCAGCA | AGCGGTCCAC | GCTGGTTTGC | CCCAGCAGGC | 3850 |
| GAAAATCCTG | TTTGATGGTG | GTTAACGGCG | GGATATAACA | TGAGCTGTCT | 3900 |

-continued

TCGGTATCGT CGTATCCCAC TACCGAGATA TCCGCACCAA CGCGCAGCCC 3950

GGACTCGGTA ATGGCGCGCA TTGCGCCCAG CGCCATCTGA TCGTTGGCAA 4000

CCAGCATCGC AGTGGGAACG ATGCCCTCAT TCAGCATTTG CATGGTTTGT 4050

TGAAAACCGG ACATGGCACT CCAGTCGCCT TCCCGTTCCG CTATCGGCTG 4100

AATTTGATTG CGAGTGAGAT ATTTATGCCA GCCAGCCAGA CGCAGACGCG 4150

CCGAGACAGA ACTTAATGGG CCCGCTAACA GCGCGATTTG CTGGTGACCC 4200

AATGCGACCA GATGCTCCAC GCCCAGTCGC GTACCGTCTT CATGGGAGAA 4250

AATAATACTG TTGATGGGTG TCTGGTCAGA GACATCAAGA AATAACGCCG 4300

GAACATTAGT GCAGGCAGCT TCCACAGCAA TGGCATCCTG GTCATCCAGC 4350

GGATAGTTAA TGATCAGCCC ACTGACGCGT TGCGCGAGAA GATTGTGCAC 4400

CGCCGCTTTA CAGGCTTCGA CGCCGCTTCG TTCTACCATC GACACCACCA 4450

CGCTGGCACC CAGTTGATCG GCGCGAGATT TAATCGCCGC GACAATTTGC 4500

GACGGCGCGT GCAGGGCCAG ACTGGAGGTG GCAACGCCAA TCAGCAACGA 4550

CTGTTTGCCC GCCAGTTGTT GTGCCACGCG GTTGGGAATG TAATTCAGCT 4600

CCGCCATCGC CGCTTCCACT TTTTCCCGCG TTTTCGCAGA AACGTGGCTG 4650

GCCTGGTTCA CCACGCGGGA AACGGTCTGA TAAGAGACAC CGGCATACTC 4700

TGCGACATCG TATAACGTTA CTGGTTTCAC ATTCACCACC CTGAATTGAC 4750

TCTCTTCCGG GCGCTATCAT GCCATACCGC GAAAGGTTTT GCGCCATTCG 4800

ATGGTGTCCG GGATCTCGAC GCTCTCCCTT ATGCGACTCC TGCATTAGGA 4850

AGCAGCCCAG TAGTAGGTTG AGGCCGTTGA GCACCGCCGC CGCAAGGAAT 4900

GGTGCATGCA AGGAGATGGC GCCCAACAGT CCCCCGGCCA CGGGGCCTGC 4950

CACCATACCC ACGCCGAAAC AAGCGCTCAT GAGCCCGAAG TGGCGAGCCC 5000

GATCTTCCCC ATCGGTGATG TCGGCGATAT AGGCGCCAGC AACCGCACCT 5050

GTGGCGCCGG TGATGCCGGC CACGATGCGT CCGGCGTAGA GGATCGAGAT 5100

CTCGATCCCG CGAAATTAAT ACGACTCACT ATAGGGGAAT TGTGAGCGGA 5150

TAACAATTCC CCTCTAGAAA TAATTTTGTT TAACTTTAAG AAGGAGATAT 5200

ACATATGGCT AGCATGACTG GTGGACAGCA AATGGGTCGC GGATCCGAAT 5250

TCGAGCTCCG TCGACAAGCT TGCGGCCGCA CTCGAGCACC ACCACCACCA 5300

CCACTGAGAT CCGGCTGCTA ACAAAGCCCG AAAGGAAGCT GAGTTGGCTG 5350

CTGCCACCGC TGAGCAATAA CTAGCATAAC CCCTTGGGGC CTCTAAACGG 5400

GTCTTGAGGG GTTTTTTGCT GAAAGGAGGA ACTATATCCG GAT 5443

( 2 ) INFORMATION FOR SEQ ID NO:2:

( i ) SEQUENCE CHARACTERISTICS:
( A ) LENGTH: 236 base pairs
( B ) TYPE: Nucleic Acid
( C ) STRANDEDNESS: Single
( D ) TOPOLOGY: Linear ( x i ) SEQUENCE DESCRIPTION: SEQ ID NO:2:

TCGACTGCAC GGTGCACCAA TGCTTCTGGC GTCAGGCAGC CATCGGAAGC 50

TGTGGTATGG CTGTGCAGGT CGTAAATCAT CGCATAATTC GTGTCGCTCA 100

AGGCGCACTC CCGTTCTGGA TAATGTTTTT TGCGCCGACA TCATAACGGT 150

TCTGGCAAAT ATTCTGAAAT GAGCTGTTGA CAATTAATCA TCGAACTAGT 200

-continued

TTAATGTGTG GAATTGTGAG CGGATAACAA TTCCCC 236

(2) INFORMATION FOR SEQ ID NO:3:

(i) SEQUENCE CHARACTERISTICS:
(A) LENGTH: 5616 base pairs
(B) TYPE: Nucleic Acid
(C) STRANDEDNESS: Single
(D) TOPOLOGY: Linear (xi) SEQUENCE DESCRIPTION: SEQ ID NO:3:

TGGCGAATGG GACGCGCCCT GTAGCGGCGC ATTAAGCGCG GCGGGTGTGG 50

TGGTTACGCG CAGCGTGACC GCTACACTTG CCAGCGCCCT AGCGCCCGCT 100

CCTTTCGCTT TCTTCCCTTC CTTTCTCGCC ACGTTCGCCG GCTTTCCCCG 150

TCAAGCTCTA AATCGGGGGC TCCCTTTAGG GTTCCGATTT AGTGCTTTAC 200

GGCACCTCGA CCCCAAAAAA CTTGATTAGG GTGATGGTTC ACGTAGTGGG 250

CCATCGCCCT GATAGACGGT TTTTCGCCCT TTGACGTTGG AGTCCACGTT 300

CTTTAATAGT GGACTCTTGT TCCAAACTGG AACAACACTC AACCCTATCT 350

CGGTCTATTC TTTTGATTTA TAAGGGATTT TGCCGATTTC GGCCTATTGG 400

TTAAAAAATG AGCTGATTTA ACAAAAATTT AACGCGAATT TTAACAAAAT 450

ATTAACGTTT ACAATTTCAG GTGGCACTTT TCGGGGAAAT GTGCGCGGAA 500

CCCCTATTTG TTTATTTTTC TAAATACATT CAAATATGTA TCCGCTCATG 550

AGACAATAAC CCTGATAAAT GCTTCAATAA TATTGAAAAA GGAAGAGTAT 600

GAGTATTCAA CATTTCCGTG TCGCCCTTAT TCCCTTTTTT GCGGCATTTT 650

GCCTTCCTGT TTTTGCTCAC CCAGAAACGC TGGTGAAAGT AAAAGATGCT 700

GAAGATCAGT TGGGTGCACG AGTGGGTTAC ATCGAACTGG ATCTCAACAG 750

CGGTAAGATC CTTGAGAGTT TTCGCCCCGA AGAACGTTTT CCAATGATGA 800

GCACTTTTAA AGTTCTGCTA TGTGGCGCGG TATTATCCCG TATTGACGCC 850

GGGCAAGAGC AACTCGGTCG CCGCATACAC TATTCTCAGA ATGACTTGGT 900

TGAGTACTCA CCAGTCACAG AAAAGCATCT TACGGATGGC ATGACAGTAA 950

GAGAATTATG CAGTGCTGCC ATAACCATGA GTGATAACAC TGCGGCCAAC 1000

TTACTTCTGA CAACGATCGG AGGACCGAAG GAGCTAACCG CTTTTTTGCA 1050

CAACATGGGG GATCATGTAA CTCGCCTTGA TCGTTGGGAA CCGGAGCTGA 1100

ATGAAGCCAT ACCAAACGAC GAGCGTGACA CCACGATGCC TGCAGCAATG 1150

GCAACAACGT TGCGCAAACT ATTAACTGGC GAACTACTTA CTCTAGCTTC 1200

CCGGCAACAA TTAATAGACT GGATGGAGGC GGATAAAGTT GCAGGACCAC 1250

TTCTGCGCTC GGCCCTTCCG GCTGGCTGGT TTATTGCTGA TAAATCTGGA 1300

GCCGGTGAGC GTGGGTCTCG CGGTATCATT GCAGCACTGG GGCCAGATGG 1350

TAAGCCCTCC CGTATCGTAG TTATCTACAC GACGGGGAGT CAGGCAACTA 1400

TGGATGAACG AAATAGACAG ATCGCTGAGA TAGGTGCCTC ACTGATTAAG 1450

CATTGGTAAC TGTCAGACCA AGTTTACTCA TATATACTTT AGATTGATTT 1500

AAAACTTCAT TTTTAATTTA AAAGGATCTA GGTGAAGATC CTTTTTGATA 1550

ATCTCATGAC CAAAATCCCT TAACGTGAGT TTTCGTTCCA CTGAGCGTCA 1600

GACCCCGTAG AAAAGATCAA AGGATCTTCT TGAGATCCTT TTTTTCTGCG 1650

-continued

| | | | | | |
|---|---|---|---|---|---|
| CGTAATCTGC | TGCTTGCAAA | CAAAAAAACC | ACCGCTACCA | GCGGTGGTTT | 1700 |
| GTTTGCCGGA | TCAAGAGCTA | CCAACTCTTT | TTCCGAAGGT | AACTGGCTTC | 1750 |
| AGCAGAGCGC | AGATACCAAA | TACTGTCCTT | CTAGTGTAGC | CGTAGTTAGG | 1800 |
| CCACCACTTC | AAGAACTCTG | TAGCACCGCC | TACATACCTC | GCTCTGCTAA | 1850 |
| TCCTGTTACC | AGTGGCTGCT | GCCAGTGGCG | ATAAGTCGTG | TCTTACCGGG | 1900 |
| TTGGACTCAA | GACGATAGTT | ACCGGATAAG | GCGCAGCGGT | CGGGCTGAAC | 1950 |
| GGGGGGTTCG | TGCACACAGC | CCAGCTTGGA | GCGAACGACC | TACACCGAAC | 2000 |
| TGAGATACCT | ACAGCGTGAG | CTATGAGAAA | GCGCCACGCT | TCCCGAAGGG | 2050 |
| AGAAAGGCGG | ACAGGTATCC | GGTAAGCGGC | AGGGTCGGAA | CAGGAGAGCG | 2100 |
| CACGAGGGAG | CTTCCAGGGG | GAAACGCCTG | GTATCTTTAT | AGTCCTGTCG | 2150 |
| GGTTTCGCCA | CCTCTGACTT | GAGCGTCGAT | TTTTGTGATG | CTCGTCAGGG | 2200 |
| GGGCGGAGCC | TATGGAAAAA | CGCCAGCAAC | GCGGCCTTTT | TACGGTTCCT | 2250 |
| GGCCTTTTGC | TGGCCTTTTG | CTCACATGTT | CTTTCCTGCG | TTATCCCCTG | 2300 |
| ATTCTGTGGA | TAACCGTATT | ACCGCCTTTG | AGTGAGCTGA | TACCGCTCGC | 2350 |
| CGCAGCCGAA | CGACCGAGCG | CAGCGAGTCA | GTGAGCGAGG | AAGCGGAAGA | 2400 |
| GCGCCTGATG | CGGTATTTTC | TCCTTACGCA | TCTGTGCGGT | ATTTCACACC | 2450 |
| GCATATATGG | TGCACTCTCA | GTACAATCTG | CTCTGATGCC | GCATAGTTAA | 2500 |
| GCCAGTATAC | ACTCCGCTAT | CGCTACGTGA | CTGGGTCATG | GCTGCGCCCC | 2550 |
| GACACCCGCC | AACACCCGCT | GACGCGCCCT | GACGGGCTTG | TCTGCTCCCG | 2600 |
| GCATCCGCTT | ACAGACAAGC | TGTGACCGTC | TCCGGGAGCT | GCATGTGTCA | 2650 |
| GAGGTTTTCA | CCGTCATCAC | CGAAACGCGC | GAGGCAGCTG | CGGTAAAGCT | 2700 |
| CATCAGCGTG | GTCGTGAAGC | GATTCACAGA | TGTCTGCCTG | TTCATCCGCG | 2750 |
| TCCAGCTCGT | TGAGTTTCTC | CAGAAGCGTT | AATGTCTGGC | TTCTGATAAA | 2800 |
| GCGGGCCATG | TTAAGGGCGG | TTTTTTCCTG | TTTGGTCACT | GATGCCTCCG | 2850 |
| TGTAAGGGGG | ATTTCTGTTC | ATGGGGGTAA | TGATACCGAT | GAAACGAGAG | 2900 |
| AGGATGCTCA | CGATACGGGT | TACTGATGAT | GAACATGCCC | GGTTACTGGA | 2950 |
| ACGTTGTGAG | GGTAAACAAC | TGGCGGTATG | GATGCGGCGG | GACCAGAGAA | 3000 |
| AAATCACTCA | GGGTCAATGC | CAGCGCTTCG | TTAATACAGA | TGTAGGTGTT | 3050 |
| CCACAGGGTA | GCCAGCAGCA | TCCTGCGATG | CAGATCCGGA | ACATAATGGT | 3100 |
| GCAGGGCGCT | GACTTCCGCG | TTTCCAGACT | TTACGAAACA | CGGAAACCGA | 3150 |
| AGACCATTCA | TGTTGTTGCT | CAGGTCGCAG | ACGTTTTGCA | GCAGCAGTCG | 3200 |
| CTTCACGTTC | GCTCGCGTAT | CGGTGATTCA | TTCTGCTAAC | CAGTAAGGCA | 3250 |
| ACCCCGCCAG | CCTAGCCGGG | TCCTCAACGA | CAGGAGCACG | ATCATGCGCA | 3300 |
| CCCGTGGGGC | CGCCATGCCG | GCGATAATGG | CCTGCTTCTC | GCCGAAACGT | 3350 |
| TTGGTGGCGG | GACCAGTGAC | GAAGGCTTGA | GCGAGGGCGT | GCAAGATTCC | 3400 |
| GAATACCGCA | AGCGACAGGC | CGATCATCGT | CGCGCTCCAG | CGAAAGCGGT | 3450 |
| CCTCGCCGAA | AATGACCCAG | AGCGCTGCCG | GCACCTGTCC | TACGAGTTGC | 3500 |
| ATGATAAAGA | AGACAGTCAT | AAGTGCGGCG | ACGATAGTCA | TGCCCCGCGC | 3550 |
| CCACCGGAAG | GAGCTGACTG | GGTTGAAGGC | TCTCAAGGGC | ATCGGTCGAG | 3600 |
| ATCCCGGTGC | CTAATGAGTG | AGCTAACTTA | CATTAATTGC | GTTGCGCTCA | 3650 |

-continued

| | | | | | |
|---|---|---|---|---|---|
| CTGCCCGCTT | TCCAGTCGGG | AAACCTGTCG | TGCCAGCTGC | ATTAATGAAT | 3700 |
| CGGCCAACGC | GCGGGGAGAG | GCGGTTTGCG | TATTGGGCGC | CAGGGTGGTT | 3750 |
| TTTCTTTTCA | CCAGTGAGAC | GGGCAACAGC | TGATTGCCCT | TCACCGCCTG | 3800 |
| GCCCTGAGAG | AGTTGCAGCA | AGCGGTCCAC | GCTGGTTTGC | CCCAGCAGGC | 3850 |
| GAAAATCCTG | TTTGATGGTG | GTTAACGGCG | GGATATAACA | TGAGCTGTCT | 3900 |
| TCGGTATCGT | CGTATCCCAC | TACCGAGATA | TCCGCACCAA | CGCGCAGCCC | 3950 |
| GGACTCGGTA | ATGGCGCGCA | TTGCGCCCAG | CGCCATCTGA | TCGTTGGCAA | 4000 |
| CCAGCATCGC | AGTGGGAACG | ATGCCCTCAT | TCAGCATTTG | CATGGTTTGT | 4050 |
| TGAAAACCGG | ACATGGCACT | CCAGTCGCCT | TCCCGTTCCG | CTATCGGCTG | 4100 |
| AATTTGATTG | CGAGTGAGAT | ATTTATGCCA | GCCAGCCAGA | CGCAGACGCG | 4150 |
| CCGAGACAGA | ACTTAATGGG | CCCGCTAACA | GCGCGATTTG | CTGGTGACCC | 4200 |
| AATGCGACCA | GATGCTCCAC | GCCCAGTCGC | GTACCGTCTT | CATGGGAGAA | 4250 |
| AATAATACTG | TTGATGGGTG | TCTGGTCAGA | GACATCAAGA | AATAACGCCG | 4300 |
| GAACATTAGT | GCAGGCAGCT | TCCACAGCAA | TGGCATCCTG | GTCATCCAGC | 4350 |
| GGATAGTTAA | TGATCAGCCC | ACTGACGCGT | TGCGCGAGAA | GATTGTGCAC | 4400 |
| CGCCGCTTTA | CAGGCTTCGA | CGCCGCTTCG | TTCTACCATC | GACACCACCA | 4450 |
| CGCTGGCACC | CAGTTGATCG | GCGCGAGATT | TAATCGCCGC | GACAATTTGC | 4500 |
| GACGGCGCGT | GCAGGGCCAG | ACTGGAGGTG | GCAACGCCAA | TCAGCAACGA | 4550 |
| CTGTTTGCCC | GCCAGTTGTT | GTGCCACGCG | GTTGGGAATG | TAATTCAGCT | 4600 |
| CCGCCATCGC | CGCTTCCACT | TTTTCCCGCG | TTTTCGCAGA | AACGTGGCTG | 4650 |
| GCCTGGTTCA | CCACGCGGGA | AACGGTCTGA | TAAGAGACAC | CGGCATACTC | 4700 |
| TGCGACATCG | TATAACGTTA | CTGGTTTCAC | ATTCACCACC | CTGAATTGAC | 4750 |
| TCTCTTCCGG | GCGCTATCAT | GCCATACCGC | GAAAGGTTTT | GCGCCATTCG | 4800 |
| ATGGTGTCCG | GGATCTCGAC | GCTCTCCCTT | ATGCGACTCC | TGCATTAGGA | 4850 |
| AGCAGCCCAG | TAGTAGGTTG | AGGCCGTTGA | GCACCGCCGC | CGCAAGGAAT | 4900 |
| GGTGCATGCA | AGGAGATGGC | GCCCAACAGT | CCCCCGGCCA | CGGGGCCTGC | 4950 |
| CACCATACCC | ACGCCGAAAC | AAGCGCTCAT | GAGCCCGAAG | TGGCGAGCCC | 5000 |
| GATCTTCCCC | ATCGGTGATG | TCGGCGATAT | AGGCGCCAGC | AACCGCACCT | 5050 |
| GTGGCGCCGG | TGATGCCGGC | CACGATGCGT | CCGGCGTAGA | GGATCGAGAT | 5100 |
| CTCGACTGCA | CGGGCACAAT | GCTTCTGGCG | TCAGGCAGCC | ATCGGAAGCT | 5150 |
| GTGGTATGGC | TGTGCAGGTC | GTAAATCACT | GCATAATTCG | TGTCGCTCAA | 5200 |
| GGCGCACTCC | CGTTCTGGAT | AATGTTTTTT | GCGCCGACAT | CATAACGGTT | 5250 |
| CTGGCAAATA | TTCTGAAATG | AGCTGTTGAC | AATTAATCAT | CGAACTAGTT | 5300 |
| TAATGTGTGG | AATTGTGAGC | GGATAACAAT | TCCCCTCTAG | AAATAATTTT | 5350 |
| GTTTAACTTT | AAGAAGGAGA | TATACATATG | GCTAGCATGA | CTGGTGGACA | 5400 |
| GCAAATGGGT | CGCGGATCCG | AATTCGAGCT | CCGTCGACAA | GCTTGCGGCC | 5450 |
| GCACTCGAGC | ACCACCACCA | CCACCACTGA | GATCCGGCTG | CTAACAAAGC | 5500 |
| CCGAAAGGAA | GCTGAGTTGG | CTGCTGCCAC | CGCTGAGCAA | TAACTAGCAT | 5550 |
| AACCCCTTGG | GGCCTCTAAA | CGGGTCTTGA | GGGGTTTTTT | GCTGAAAGGA | 5600 |
| GGAACTATAT | CCGGAT | | | | 5616 |

( 2 ) INFORMATION FOR SEQ ID NO:4:

( i ) SEQUENCE CHARACTERISTICS:
( A ) LENGTH: 4245 base pairs
( B ) TYPE: Nucleic Acid
( C ) STRANDEDNESS: Single
( D ) TOPOLOGY: Linear ( x i ) SEQUENCE DESCRIPTION: SEQ ID NO:4:

```
GAATTCCGGA TGAGCATTCA TCAGGCGGGC AAGAATGTGA ATAAAGGCCG    50
GATAAAACTT GTGCTTATTT TTCTTTACGG TCTTTAAAAA GGCCGTAATA   100
TCCAGCTGAA CGGTCTGGTT ATAGGTACAT TGAGCAACTG ACTGAAATGC   150
CTCAAAATGT TCTTTACGAT GCCATTGGGA TATATCAACG GTGGTATATC   200
CAGTGATTTT TTTCTCCATT TTAGCTTCCT TAGCTCCTGA AAATCTCGAT   250
AACTCAAAAA ATACGCCCGG TAGTGATCTT ATTTCATTAT GGTGAAAGTT   300
GGAACCTCTT ACGTGCCGAT CAACGTCTCA TTTTCGCCAA AAGTTGGCCC   350
AGGGCTTCCC GGTATCAACA GGGACACCAG GATTTATTTA TTCTGCGAAG   400
TGATCTTCCG TCACAGGTAT TTATTCGGCG CAAAGTGCGT CGGGTGATGC   450
TGCCAACTTA CTGATTTAGT GTATGATGGT GTTTTTGAGG TGCTCCAGTG   500
GCTTCTGTTT CTATCAGCTG TCCCTCCTGT TCAGCTACTG ACGGGGTGGT   550
GCGTAACGGC AAAAGCACCG CCGGACATCA GCGCTAGCGG AGTGTATACT   600
GGCTTACTAT GTTGGCACTG ATGAGGGTGT CAGTGAAGTG CTTCATGTGG   650
CAGGAGAAAA AAGGCTGCAC CGGTGCGTCA GCAGAATATG TGATACAGGA   700
TATATTCCGC TTCCTCGCTC ACTGACTCGC TACGCTCGGT CGTTCGACTG   750
CGGCGAGCGG AAATGGCTTA CGAACGGGGC GGAGATTTCC TGGAAGATGC   800
CAGGAAGATA CTTAACAGGG AAGTGAGAGG GCCGCGGCAA AGCCGTTTTT   850
CCATAGGCTC CGCCCCCCTG ACAAGCATCA CGAAATCTGA CGCTCAAATC   900
AGTGGTGGCG AAACCCGACA GGACTATAAA GATACCAGGC GTTTCCCCCT   950
GGCGGCTCCC TCGTGCGCTC TCCTGTTCCT GCCTTTCGGT TTACCGGTGT  1000
CATTCCGCTG TTATGGCCGC GTTTGTCTCA TTCCACGCCT GACACTCAGT  1050
TCCGGGTAGG CAGTTCGCTC CAAGCTGGAC TGTATGCACG AACCCCCCGT  1100
TCAGTCCGAC CGCTGCGCCT TATCCGGTAA CTATCGTCTT GAGTCCAACC  1150
CGGAAAGACA TGCAAAAGCA CCACTGGCAG CAGCCACTGG TAATTGATTT  1200
AGAGGAGTTA GTCTTGAAGT CATGCGCCGG TTAAGGCTAA ACTGAAAGGA  1250
CAAGTTTTGG TGACTGCGCT CCTCCAAGCC AGTTACCTCG GTTCAAAGAG  1300
TTGGTAGCTC AGAGAACCTT CGAAAAACCG CCCTGCAAGG CGGTTTTTTC  1350
GTTTTCAGAG CAAGAGATTA CGCGCAGACC AAAACGATCT CAAGAAGATC  1400
ATCTTATTAA TCAGATAAAA TATTTCTAGA TTTCAGTGCA ATTTATCTCT  1450
TCAAATGTAG CACCTGAAGT CAGCCCCATA CGATATAAGT TGTAATTCTC  1500
ATGTTTGACA GCTTATCATC GATAAGCTTT AATGCGGTAG TTTATCACAG  1550
TTAAATTGCT AACGCAGTCA GGCACCGTGT ATGAAATCTA ACAATGCGCT  1600
CATCGTCATC CTCGGCACCG TCACCCTGGA TGCTGTAGGC ATAGGCTTGG  1650
TTATGCCGGT ACTGCCGGGC CTCTTGCGGG ATATCGTCCA TTCCGACAGC  1700
ATCGCCAGTC ACTATGGCGT GCTGCTAGCG CTATATGCGT TGATGCAATT  1750
```

-continued

TCTATGCGCA CCCGTTCTCG GAGCACTGTC CGACCGCTTT GGCCGCCGCC 1800

CAGTCCTGCT CGCTTCGCTA CTTGGAGCCA CTATCGACTA CGCGATCATG 1850

GCGACCACAC CCGTCCTGTG GATCCTCTAC GCCGGACGCA TCGTGGCCGG 1900

CATCACCGGC GCCACAGGTG CGGTTGCTGG CGCCTATATC GCCGACATCA 1950

CCGATGGGGA AGATCGGGCT CGCCACTTCG GGCTCATGAG CGCTTGTTTC 2000

GGCGTGGGTA TGGTGGCAGG CCCCGTGGCC GGGGGACTGT TGGGCGCCAT 2050

CTCCTTGCAT GCACCATTCC TTGCGGCGGC GGTGCTCAAC GGCCTCAACC 2100

TACTACTGGG CTGCTTCCTA ATGCAGGAGT CGCATAAGGG AGAGCGTCGA 2150

CCGATGCCCT TGAGAGCCTT CAACCCAGTC AGCTCCTTCC GGTGGGCGCG 2200

GGGCATGACT ATCGTCGCCG CACTTATGAC TGTCTTCTTT ATCATGCAAC 2250

TCGTAGGACA GGTGCCGGCA GCGCTCTGGG TCATTTTCGG CGAGGACCGC 2300

TTTCGCTGGA GCGCGACGAT GATCGGCCTG TCGCTTGCGG TATTCGGAAT 2350

CTTGCACGCC CTCGCTCAAG CCTTCGTCAC TGGTCCCGCC ACCAAACGTT 2400

TCGGCGAGAA GCAGGCCATT ATCGCCGGCA TGGCGGCCGA CGCGCTGGGC 2450

TACGTCTTGC TGGCGTTCGC GACGCGAGGC TGGATGGCCT TCCCCATTAT 2500

GATTCTTCTC GCTTCCGGCG GCATCGGGAT GCCCGCGTTG CAGGCCATGC 2550

TGTCCAGGCA GGTAGATGAC GACCATCAGG GACAGCTTCA AGGATCGCTC 2600

GCGGCTCTTA CCAGCCTAAC TTCGATCACT GGACCGCTGA TCGTCACGGC 2650

GATTTATGCC GCCTCGGCGA GCACATGGAA CGGGTTGGCA TGGATTGTAG 2700

GCGCCGCCCT ATACCTTGTC TGCCTCCCCG CGTTGCGTCG CGGTGCATGG 2750

AGCCGGGCCA CCTCGACCTG AATGGAAGCC GGCGGCACCT CGCTAACGGA 2800

TTCACCACTC CAAGAATTGG AGCCAATCAA TTCTTGCGGA GAACTGTGAA 2850

TGCGCAAACC AACCCTTGGC AGAACATATC CATCGCGTCC GCCATCTCCA 2900

GCAGCCGCAC GCGGCGCATC TCGGGCAGCG TTGGGTCCTG GCCACGGGTG 2950

CGCATGATCG TGCTCCTGTC GTTGAGGACC CGGCTAGGCT GGCGGGGTTG 3000

CCTTACTGGT TAGCAGAATG AATCACCGAT ACGCGAGCGA ACGTGAAGCG 3050

ACTGCTGCTG CAAAACGTCT GCGACCTGAG CAACAACATG AATGGTCTTC 3100

GGTTTCCGTG TTTCGTAAAG TCTGGAAACG CGGAAGTCCC CTACGTGCTG 3150

CTGAAGTTGC CCGCAACAGA GAGTGGAACC AACCGGTGAT ACCACGATAC 3200

TATGACTGAG AGTCAACGCC ATGAGCGGCC TCATTTCTTA TTCTGAGTTA 3250

CAACAGTCCG CACCGCTGTC CGGTAGCTCC TTCCGGTGGG CGCGGGGCAT 3300

GACTATCGTC GCCGCACTTA TGACTGTCTT CTTTATCATG CAACTCGTAG 3350

GACAGGTGCC GGCAGCGCCC AACAGTCCCC CGGCCACGGG GCCTGCCACC 3400

ATACCCACGC CGAAACAAGC GCCCTGCACC ATTATGTTCC GGATCTGCAT 3450

CGCAGGATGC TGCTGGCTAC CCTGTGGAAC ACCTACATCT GTATTAACGA 3500

AGCGCTAACC GTTTTTATCA GGCTCTGGGA GGCAGAATAA ATGATCATAT 3550

CGTCAATTAT TACCTCCACG GGGAGAGCCT GAGCAAACTG GCCTCAGGCA 3600

TTTGAGAAGC ACACGGTCAC ACTGCTTCCG GTAGTCAATA AACCGGTAAA 3650

CCAGCAATAG ACATAAGCGG CTATTTAACG ACCCTGCCCT GAACCGACGA 3700

CCGGGTCGAA TTTGCTTTCG AATTTCTGCC ATTCATCCGC TTATTATCAC 3750

-continued

TTATTCAGGC GTAGCACCAG GCGTTTAAGG GCACCAATAA CTGCCTTAAA 3800

AAAATTACGC CCCGCCCTGC CACTCATCGC AGTACTGTTG TAATTCATTA 3850

AGCATTCTGC CGACATGGAA GCCATCACAG ACGGCATGAT GAACCTGAAT 3900

CGCCAGCGGC ATCAGCACCT TGTCGCCTTG CGTATAATAT TTGCCCATGG 3950

TGAAAACGGG GGCGAAGAAG TTGTCCATAT TGGCCACGTT TAAATCAAAA 4000

CTGGTGAAAC TCACCCAGGG ATTGGCTGAG ACGAAAAACA TATTCTCAAT 4050

AAACCCTTTA GGGAAATAGG CCAGGTTTTC ACCGTAACAC GCCACATCTT 4100

GCGAATATAT GTGTAGAAAC TGCCGGAAAT CGTCGTGGTA TTCACTCCAG 4150

AGCGATGAAA ACGTTTCAGT TTGCTCATGG AAAACGGTGT AACAAGGGTG 4200

AACACTATCC CATATCACCA GCTCACCGTC TTTCATTGCC ATACG 4245

( 2 ) INFORMATION FOR SEQ ID NO:5:

( i ) SEQUENCE CHARACTERISTICS:
( A ) LENGTH: 4411 base pairs
( B ) TYPE: Nucleic Acid
( C ) STRANDEDNESS: Single
( D ) TOPOLOGY: Linear ( x i ) SEQUENCE DESCRIPTION: SEQ ID NO:5:

GAATTCCGGA TGAGCATTCA TCAGGCGGGC AAGAATGTGA ATAAAGGCCG 50

GATAAAACTT GTGCTTATTT TTCTTTACGG TCTTTAAAAA GGCCGTAATA 100

TCCAGCTGAA CGGTCTGGTT ATAGGTACAT TGAGCAACTG ACTGAAATGC 150

CTCAAAATGT TCTTTACGAT GCCATTGGGA TATATCAACG GTGGTATATC 200

CAGTGATTTT TTTCTCCATT TTAGCTTCCT TAGCTCCTGA AAATCTCGAT 250

AACTCAAAAA ATACGCCCGG TAGTGATCTT ATTTCATTAT GGTGAAAGTT 300

GGAACCTCTT ACGTGCCGAT CAACGTCTCA TTTTCGCCAA AAGTTGGCCC 350

AGGGCTTCCC GGTATCAACA GGGACACCAG GATTTATTTA TTCTGCGAAG 400

TGATCTTCCG TCACAGGTAT TTATTCGGCG CAAAGTGCGT CGGGTGATGC 450

TGCCAACTTA CTGATTTAGT GTATGATGGT GTTTTTGAGG TGCTCCAGTG 500

GCTTCTGTTT CTATCAGCTG TCCCTCCTGT TCAGCTACTG ACGGGGTGGT 550

GCGTAACGGC AAAAGCACCG CCGGACATCA GCGCTAGCGG AGTGTATACT 600

GGCTTACTAT GTTGGCACTG ATGAGGGTGT CAGTGAAGTG CTTCATGTGG 650

CAGGAGAAAA AAGGCTGCAC CGGTGCGTCA GCAGAATATG TGATACAGGA 700

TATATTCCGC TTCCTCGCTC ACTGACTCGC TACGCTCGGT CGTTCGACTG 750

CGGCGAGCGG AAATGGCTTA CGAACGGGGC GGAGATTTCC TGGAAGATGC 800

CAGGAAGATA CTTAACAGGG AAGTGAGAGG GCCGCGGCAA AGCCGTTTTT 850

CCATAGGCTC CGCCCCCCTG ACAAGCATCA CGAAATCTGA CGCTCAAATC 900

AGTGGTGGCG AAACCCGACA GGACTATAAA GATACCAGGC GTTTCCCCCT 950

GGCGGCTCCC TCGTGCGCTC TCCTGTTCCT GCCTTTCGGT TTACCGGTGT 1000

CATTCCGCTG TTATGGCCGC GTTTGTCTCA TTCCACGCCT GACACTCAGT 1050

TCCGGGTAGG CAGTTCGCTC CAAGCTGGAC TGTATGCACG AACCCCCCGT 1100

TCAGTCCGAC CGCTGCGCCT TATCCGGTAA CTATCGTCTT GAGTCCAACC 1150

CGGAAAGACA TGCAAAAGCA CCACTGGCAG CAGCCACTGG TAATTGATTT 1200

-continued

AGAGGAGTTA GTCTTGAAGT CATGCGCCGG TTAAGGCTAA ACTGAAAGGA 1250

CAAGTTTTGG TGACTGCGCT CCTCCAAGCC AGTTACCTCG GTTCAAAGAG 1300

TTGGTAGCTC AGAGAACCTT CGAAAAACCG CCCTGCAAGG CGGTTTTTTC 1350

GTTTTCAGAG CAAGAGATTA CGCGCAGACC AAAACGATCT CAAGAAGATC 1400

ATCTTATTAA TCAGATAAAA TATTTCTAGA TTTCAGTGCA ATTTATCTCT 1450

TCAAATGTAG CACCTGAAGT CAGCCCCATA CGATATAAGT TGTAATTCTC 1500

ATGTTTGACA GCTTATCATC GATATAGTTC CTCCTTTCAG CAAAAAACCC 1550

CTCAAGACCC GTTTAGAGGC CCCAAGGGGT TATGCTAGTT ATTGCTCAGC 1600

GGTGGCAGCA GCCAACTCAG CTTCCTTTCG GGCTTTGTTA GCAGCCGGAT 1650

CTCAGTGGTG GTGGTGGTGG TGCTCGAGTG CGGCCGCAAG CTTGTCGACG 1700

GAGCTCGAAT TCGGATCCGC GACCCATTTG CTGTCCACCA GTCATGCTAG 1750

CCATATGTAT ATCTCCTTCT TAAAGTTAAA CAAAATTATT TCTAGAGGGG 1800

AATTGTTATC CGCTCACAAT TCCACACATT AAACTAGTTC GATGATTAAT 1850

TGTCAACAGC TCATTTCAGA ATATTTGCCA GAACCGTTAT GATGTCGGCG 1900

CAAAAAACAT TATCCAGAAC GGGAGTGCGC CTTGAGCGAC ACGAATTATG 1950

CAGTGATTTA CGACCTGCAC AGCCATACCA CAGCTTCCGA TGGCTGCCTG 2000

ACGCCAGAAG CATTGTGCCC GTGCAGTCGA GATCTCGATC CTCTACGCCG 2050

GACGCATCGT GGCCGGCATC ACCGGCGCCA CAGGTGCGGT TGCTGGCGCC 2100

TATATCGCCG ACATCACCGA TGGGGAAGAT CGGGCTCGCC ACTTCGGGCT 2150

CATGAGCGCT TGTTTCGGCG TGGGTATGGT GGCAGGCCCC GTGGCCGGGG 2200

GACTGTTGGG CGCCATCTCC TTGCATGCAC CATTCCTTGC GGCGGCGGTG 2250

CTCAACGGCC TCAACCTACT ACTGGGCTGC TTCCTAATGC AGGAGTCGCA 2300

TAAGGGAGAG CGTCGAGATC CCGGACACCA TCGAATGGCG CAAAACCTTT 2350

CGCGGTATGG CATGATAGCG CCCGGAAGAG AGTCAATTCA GGGTGGTGAA 2400

TGTGAAACCA GTAACGTTAT ACGATGTCGC AGAGTATGCC GGTGTCTCTT 2450

ATCAGACCGT TTCCCGCGTG GTGAACCAGG CCAGCCACGT TTCTGCGAAA 2500

ACGCGGGAAA AAGTGGAAGC GGCGATGGCG GAGCTGAATT ACATTCCCAA 2550

CCGCGTGGCA CAACAACTGG CGGGCAAACA GTCGTTGCTG ATTGGCGTTG 2600

CCACCTCCAG TCTGGCCCTG CACGCGCCGT CGCAAATTGT CGCGGCGATT 2650

AAATCTCGCG CCGATCAACT GGGTGCCAGC GTGGTGGTGT CGATGGTAGA 2700

ACGAAGCGGC GTCGAAGCCT GTAAAGCGGC GGTGCACAAT CTTCTCGCGC 2750

AACGCGTCAG TGGGCTGATC ATTAACTATC CGCTGGATGA CCAGGATGCC 2800

ATTGCTGTGG AAGCTGCCTG CACTAATGTT CCGGCGTTAT TTCTTGATGT 2850

CTCTGACCAG ACACCCATCA ACAGTATTAT TTTCTCCCAT GAAGACGGTA 2900

CGCGACTGGG CGTGGAGCAT CTGGTCGCAT TGGGTCACCA GCAAATCGCG 2950

CTGTTAGCGG GCCCATTAAG TTCTGTCTCG GCGCGTCTGC GTCTGGCTGG 3000

CTGGCATAAA TATCTCACTC GCAATCAAAT TCAGCCGATA GCGGAACGGG 3050

AAGGCGACTG GAGTGCCATG TCCGGTTTTC AACAAACCAT GCAAATGCTG 3100

AATGAGGGCA TCGTTCCCAC TGCGATGCTG GTTGCCAACG ATCAGATGGC 3150

GCTGGGCGCA ATGCGCGCCA TTACCGAGTC CGGGCTGCGC GTTGGTGCGG 3200

-continued

| | | | | | |
|---|---|---|---|---|---|
| ATATCTCGGT | AGTGGGATAC | GACGATACCG | AAGACAGCTC | ATGTTATATC | 3250 |
| CCGCCGTTAA | CCACCATCAA | ACAGGATTTT | CGCCTGCTGG | GGCAAACCAG | 3300 |
| CGTGGACCGC | TTGCTGCAAC | TCTCTCAGGG | CCAGGCGGTG | AAGGGCAATC | 3350 |
| AGCTGTTGCC | CGTCTCACTG | GTGAAAAGAA | AAACCACCCT | GGCGCCCAAT | 3400 |
| ACGCAAACCG | CCTCTCCCCG | CGCGTTGGCC | GATTCATTAA | TGCAGCTGGC | 3450 |
| ACGACAGGTT | TCCCGACTGG | AAAGCGGGCA | GTGAGCGCAA | CGCAATTAAT | 3500 |
| GTAAGTTAGC | TCACTCATTA | GGCCCCGGCA | GCGCCCAACA | GTCCCCCGGC | 3550 |
| CACGGGGCCT | GCCACCATAC | CCACGCCGAA | ACAAGCGCCC | TGCACCATTA | 3600 |
| TGTTCCGGAT | CTGCATCGCA | GGATGCTGCT | GGCTACCCTG | TGGAACACCT | 3650 |
| ACATCTGTAT | TAACGAAGCG | CTAACCGTTT | TTATCAGGCT | CTGGGAGGCA | 3700 |
| GAATAAATGA | TCATATCGTC | AATTATTACC | TCCACGGGGA | GAGCCTGAGC | 3750 |
| AAACTGGCCT | CAGGCATTTG | AGAAGCACAC | GGTCACACTG | CTTCCGGTAG | 3800 |
| TCAATAAACC | GGTAAACCAG | CAATAGACAT | AAGCGGCTAT | TTAACGACCC | 3850 |
| TGCCCTGAAC | CGACGACCGG | GTCGAATTTG | CTTTCGAATT | TCTGCCATTC | 3900 |
| ATCCGCTTAT | TATCACTTAT | TCAGGCGTAG | CACCAGGCGT | TTAAGGGCAC | 3950 |
| CAATAACTGC | CTTAAAAAAA | TTACGCCCCG | CCCTGCCACT | CATCGCAGTA | 4000 |
| CTGTTGTAAT | TCATTAAGCA | TTCTGCCGAC | ATGGAAGCCA | TCACAGACGG | 4050 |
| CATGATGAAC | CTGAATCGCC | AGCGGCATCA | GCACCTTGTC | GCCTTGCGTA | 4100 |
| TAATATTTGC | CCATGGTGAA | AACGGGGGCG | AAGAAGTTGT | CCATATTGGC | 4150 |
| CACGTTTAAA | TCAAAACTGG | TGAAACTCAC | CCAGGGATTG | GCTGAGACGA | 4200 |
| AAAACATATT | CTCAATAAAC | CCTTTAGGGA | AATAGGCCAG | GTTTTCACCG | 4250 |
| TAACACGCCA | CATCTTGCGA | ATATATGTGT | AGAAACTGCC | GGAAATCGTC | 4300 |
| GTGGTATTCA | CTCCAGAGCG | ATGAAAACGT | TTCAGTTTGC | TCATGGAAAA | 4350 |
| CGGTGTAACA | AGGGTGAACA | CTATCCCATA | TCACCAGCTC | ACCGTCTTTC | 4400 |
| ATTGCCATAC | G | | | | 4411 |

( 2 ) INFORMATION FOR SEQ ID NO:6:

( i ) SEQUENCE CHARACTERISTICS:
( A ) LENGTH: 6363 base pairs
( B ) TYPE: Nucleic Acid
( C ) STRANDEDNESS: Single
( D ) TOPOLOGY: Linear ( x i ) SEQUENCE DESCRIPTION: SEQ ID NO:6:

| | | | | | |
|---|---|---|---|---|---|
| CGTATGGCAA | TGAAAGACGG | TGAGCTGGTG | ATATGGGATA | GTGTTCACCC | 50 |
| TTGTTACACC | GTTTTCCATG | AGCAAACTGA | AACGTTTTCA | TCGCTCTGGA | 100 |
| GTGAATACCA | CGACGATTTC | CGGCAGTTTC | TACACATATA | TTCGCAAGAT | 150 |
| GTGGCGTGTT | ACGGTGAAAA | CCTGGCCTAT | TTCCCTAAAG | GGTTTATTGA | 200 |
| GAATATGTTT | TTCGTCTCAG | CCAATCCCTG | GGTGAGTTTC | ACCAGTTTTG | 250 |
| ATTTAAACGT | GGCCAATATG | GACAACTTCT | TCGCCCCCGT | TTTCACCATG | 300 |
| GGCAAATATT | ATACGCAAGG | CGACAAGGTG | CTGATGCCGC | TGGCGATTCA | 350 |
| GGTTCATCAT | GCCGTCTGTG | ATGGCTTCCA | TGTCGGCAGA | ATGCTTAATG | 400 |
| AATTACAACA | GTACTGCGAT | GAGTGGCAGG | GCGGGGCGTA | ATTTTTTTAA | 450 |
| GGCAGTTATT | GGTGCCCTTA | AACGCCTGGT | GCTACGCCTG | AATAAGTGAT | 500 |

-continued

AATAAGCGGA TGAATGGCAG AAATTCGAAA GCAAATTCGA CCCGGTCGTC 550

GGTTCAGGGC AGGGTCGTTA AATAGCCGCT TATGTCTATT GCTGGTTTAC 600

CGGTTTATTG ACTACCGGAA GCAGTGTGAC CGTGTGCTTC TCAAATGCCT 650

GAGGCCAGTT TGCTCAGGCT CTCCCCGTGG AGGTAATAAT TGACGATATG 700

ATCATTTATT CTGCCTCCCA GAGCCTGATA AAAACGGTTA GCGCTTCGTT 750

AATACAGATG TAGGTGTTCC ACAGGGTAGC CAGCAGCATC CTGCGATGCA 800

GATCCGGAAC ATAATGGTGC AGGGCGCTTG TTTCGGCGTG GGTATGGTGG 850

CAGGCCCCGT GGCCGGGGGA CTGTTGGGCG CTGCCGGGGC CTAATGAGTG 900

AGCTAACTTA CATTAATTGC GTTGCGCTCA CTGCCCGCTT TCCAGTCGGG 950

AAACCTGTCG TGCCAGCTGC ATTAATGAAT CGGCCAACGC GCGGGGAGAG 1000

GCGGTTTGCG TATTGGGCGC CAGGGTGGTT TTTCTTTTCA CCAGTGAGAC 1050

GGGCAACAGC TGATTGCCCT TCACCGCCTG GCCCTGAGAG AGTTGCAGCA 1100

AGCGGTCCAC GCTGGTTTGC CCCAGCAGGC GAAAATCCTG TTTGATGGTG 1150

GTTAACGGCG GGATATAACA TGAGCTGTCT TCGGTATCGT CGTATCCCAC 1200

TACCGAGATA TCCGCACCAA CGCGCAGCCC GGACTCGGTA ATGGCGCGCA 1250

TTGCGCCCAG CGCCATCTGA TCGTTGGCAA CCAGCATCGC AGTGGGAACG 1300

ATGCCCTCAT TCAGCATTTG CATGGTTTGT TGAAAACCGG ACATGGCACT 1350

CCAGTCGCCT TCCCGTTCCG CTATCGGCTG AATTTGATTG CGAGTGAGAT 1400

ATTTATGCCA GCCAGCCAGA CGCAGACGCG CCGAGACAGA ACTTAATGGG 1450

CCCGCTAACA GCGCGATTTG CTGGTGACCC AATGCGACCA GATGCTCCAC 1500

GCCCAGTCGC GTACCGTCTT CATGGGAGAA AATAATACTG TTGATGGGTG 1550

TCTGGTCAGA GACATCAAGA AATAACGCCG GAACATTAGT GCAGGCAGCT 1600

TCCACAGCAA TGGCATCCTG GTCATCCAGC GGATAGTTAA TGATCAGCCC 1650

ACTGACGCGT TGCGCGAGAA GATTGTGCAC CGCCGCTTTA CAGGCTTCGA 1700

CGCCGCTTCG TTCTACCATC GACACCACCA CGCTGGCACC CAGTTGATCG 1750

GCGCGAGATT TAATCGCCGC GACAATTTGC GACGGCGCGT GCAGGGCCAG 1800

ACTGGAGGTG GCAACGCCAA TCAGCAACGA CTGTTTGCCC GCCAGTTGTT 1850

GTGCCACGCG GTTGGGAATG TAATTCAGCT CCGCCATCGC CGCTTCCACT 1900

TTTTCCCGCG TTTTCGCAGA AACGTGGCTG GCCTGGTTCA CCACGCGGGA 1950

AACGGTCTGA TAAGAGACAC CGGCATACTC TGCGACATCG TATAACGTTA 2000

CTGGTTTCAC ATTCACCACC CTGAATTGAC TCTCTTCCGG GCGCTATCAT 2050

GCCATACCGC GAAAGGTTTT GCGCCATTCG ATGGTGTCCG GGATCTCGAC 2100

GCTCTCCCTT ATGCGACTCC TGCATTAGGA AGCAGCCCAG TAGTAGGTTG 2150

AGGCCGTTGA GCACCGCCGC CGCAAGGAAT GGTGCATGCA AGGAGATGGC 2200

GCCCAACAGT CCCCCGGCCA CGGGGCCTGC CACCATACCC ACGCCGAAAC 2250

AAGCGCTCAT GAGCCCGAAG TGGCGAGCCC GATCTTCCCC ATCGGTGATG 2300

TCGGCGATAT AGGCGCCAGC AACCGCACCT GTGGCGCCGG TGATGCCGGC 2350

CACGATGCGT CCGGCGTAGA GGATCGAGAT CTCGACTGCA CGGGCACAAT 2400

GCTTCTGGCG TCAGGCAGCC ATCGGAAGCT GTGGTATGGC TGTGCAGGTC 2450

GTAAATCACT GCATAATTCG TGTCGCTCAA GGCGCACTCC CGTTCTGGAT 2500

-continued

AATGTTTTTT GCGCCGACAT CATAACGGTT CTGGCAAATA TTCTGAAATG 2550

AGCTGTTGAC AATTAATCAT CGAACTAGTT TAATGTGTGG AATTGTGAGC 2600

GGATAACAAT TCCCCTCTAG AAATAATTTT GTTTAACTTT AAGAAGGAGA 2650

TATACATATG CCTTTGAATA TCGAAGATGA GCATCGTCTG CATGAGACCT 2700

CAAAAGAGCC GGATGTTTCT CTAGGGTCCA CATGGCTTTC TGCTTTCCCC 2750

CAGGCCTGGG CAGAAACCGG GGGCATGGGA CTGGCAGTTC GCCAAGCTCC 2800

TCTGATCATA CCTCTGAAGG CAACCTCTAC CCCCGTGTCC ATAAAACAAT 2850

ACCCCATGTC ACAAGAAGCC AGACTGGGGA TCAAGCCCCA CATACAGAGA 2900

CTGTTGGACC AGGGAATACT GGTACCCTGC CAGTCCCCCT GGAACACGCC 2950

CCTGCTACCC ATTAAGAAAC CAGGGACTAA TGATTACAGG CCTGTCCAAG 3000

ATCTGAGAGA AGTCAACAAG CGGGTGGAAG ACATCCACCC CACCGTGCCC 3050

AACCCTTACA ACCTCTTGAG TGGGCTCCCA CCGTCCCACC AGTGGTACAC 3100

TGTGCTTGAC TTAAAGGATG CCTTTTTCTG CCTGAGACTC CACCCCACCA 3150

GTCAGCCTCT CTTCGCCTTT GAGTGGAGAG ACCCAGAGAT GGGAATCTCA 3200

GGACAATTAA CCTGGACCAG ACTCCCACAG GGTTTCAAAA ACAGTCCCAC 3250

CCTGTTTGAT GAGGCACTGC ACAGAGACCT AGCAGGCTTC CGGATCCAGC 3300

ACCCAGACTT GATCCTGCTA CAGTACGTGG ATGACTTACT GCTGGCCGCC 3350

TCTTCTGAGC TCGACTGCCA ACAAGGTACT CGGGCCCTGT TACAAACCCT 3400

AGGGGACCTC GGGTATCGGG CCTCGGCCAA GAAAGCCCAA ATTTGCCAAA 3450

AACAGGTCAA ATATCTGGGG TATCTCCTAA AAGAGGGTCA GAGATGGCTG 3500

ACTGAGGCCA GAAAAGAGAC TGTGATGGGG CAGCCTACTC CGAAGACCCC 3550

TCGACAACTA AGGGAGTTCC TAGGGACGGC AGGCTTCTGT CGCCTCTGGA 3600

TCCCTGGGTT TGCAGAAATG GCAGCCCCCT TGTACCCTCT CACCAAAACG 3650

GGGACTCTGT TTAATTGGGG TCCAGACCAG CAAAAAGCCT ATCAAGAAAT 3700

CAAACAGGCT CTTCTAACTG CCCCAGCCCT GGGATTGCCA GACTTGACTA 3750

AGCCCTTTGA ACTCTTTGTC GACGAGAAAC AGGGCTACGC CAAAGGCGTC 3800

CTAACGCAAA AACTGGGACC TTGGCGTCGG CCGGTGGCCT ACCTGTCTAA 3850

AAAGCTAGAC CCAGTGGCAG CTGGCTGGCC CCCTTGCCTA CGGATGGTGG 3900

CAGCCATTGC AGTTCTGACA AAAGATGCTG GTAAGCTCAC TATGGGACAG 3950

CCATTAGTCA TTCTGGCCCC CCATGCCGTA GAGACACTAG TTAAGCAACC 4000

CCCTGATCGC TGGCTCTCCA ACGCCCGGAT GACCCATTAC CAAGCCCTGC 4050

TCCTGGACAC GGACCGGGTC CAGTTCGGGC CAGTAGTGGC CCTAAATCCA 4100

GCTACGCTGC TCCCTCTGCC TAAGGAGGGG CTGCAACATG ACTGTCTTGA 4150

CATCTTGGCT GAAGCCCACG GAACTAGATC AGATCTTACG GACCAGCCCC 4200

TCCCAGACGC CGACCACACC TGGTACACGG ATGGGAGCAG CTTCCTGCAA 4250

GAAGGGCAGC GCAAGGCCGG AGCAGCGGTG ACCACCGAGA CTGAGGTAAT 4300

CTGGGCCAGG GCATTGCCAG CCGGGACATC GGCCCAAAGA GCTGAACTGA 4350

TAGCGCTCAC CCAAGCCCTA AAGATGGCAG AAGGTAAGAA GCTAAATGTT 4400

TATACTGATA GCCGTTATGC TTTTGCCACC GCTCATATTC ATGGAGAAAT 4450

ATACAGAAGA CGCGGGTTGC TCACATCAGA AGGAAAAGAA ATCAAGAACA 4500

AGGGCGAGAT CTTAGCCCTA CTAAAGGCTC TCTTCTTGCC CAAAAGACTT 4550
AGCATAATTC ATTGCCCGGG GCATCAAAAG GGAAACAGCG CAGAGGCCAG 4600
GGGCAACCGG ATGGCTGACC AAGCGGCGCG CAAGGCAGCC ATCACAGAGA 4650
CTTAAGAGCT CCGTCGACAA GCTTGCGGCC GCACTCGAGC ACCACCACCA 4700
CCACCACTGA GATCCGGCTG CTAACAAAGC CCGAAAGGAA GCTGAGTTGG 4750
CTGCTGCCAC CGCTGAGCAA TAACTAGCAT AACCCCTTGG GGCCTCTAAA 4800
CGGGTCTTGA GGGGTTTTTT GCTGAAAGGA GGAACTATAT ATCGATGATA 4850
AGCTGTCAAA CATGAGAATT ACAACTTATA TCGTATGGGG CTGACTTCAG 4900
GTGCTACATT TGAAGAGATA AATTGCACTG AAATCTAGAA ATATTTTATC 4950
TGATTAATAA GATGATCTTC TTGAGATCGT TTTGGTCTGC GCGTAATCTC 5000
TTGCTCTGAA AACGAAAAAA CCGCCTTGCA GGGCGGTTTT TCGAAGGTTC 5050
TCTGAGCTAC CAACTCTTTG AACCGAGGTA ACTGGCTTGG AGGAGCGCAG 5100
TCACCAAAAC TTGTCCTTTC AGTTTAGCCT TAACCGGCGC ATGACTTCAA 5150
GACTAACTCC TCTAAATCAA TTACCAGTGG CTGCTGCCAG TGGTGCTTTT 5200
GCATGTCTTT CCGGGTTGGA CTCAAGACGA TAGTTACCGG ATAAGGCGCA 5250
GCGGTCGGAC TGAACGGGGG GTTCGTGCAT ACAGTCCAGC TTGGAGCGAA 5300
CTGCCTACCC GGAACTGAGT GTCAGGCGTG GAATGAGACA AACGCGGCCA 5350
TAACAGCGGA ATGACACCGG TAAACCGAAA GGCAGGAACA GGAGAGCGCA 5400
CGAGGGAGCC GCCAGGGGGA AACGCCTGGT ATCTTTATAG TCCTGTCGGG 5450
TTTCGCCACC ACTGATTTGA GCGTCAGATT TCGTGATGCT TGTCAGGGGG 5500
GCGGAGCCTA TGGAAAAACG GCTTTGCCGC GGCCCTCTCA CTTCCCTGTT 5550
AAGTATCTTC CTGGCATCTT CCAGGAAATC TCCGCCCCGT TCGTAAGCCA 5600
TTTCCGCTCG CCGCAGTCGA ACGACCGAGC GTAGCGAGTC AGTGAGCGAG 5650
GAAGCGGAAT ATATCCTGTA TCACATATTC TGCTGACGCA CCGGTGCAGC 5700
CTTTTTTCTC CTGCCACATG AAGCACTTCA CTGACACCCT CATCAGTGCC 5750
AACATAGTAA GCCAGTATAC ACTCCGCTAG CGCTGATGTC CGGCGGTGCT 5800
TTTGCCGTTA CGCACCACCC CGTCAGTAGC TGAACAGGAG GGACAGCTGA 5850
TAGAAACAGA AGCCACTGGA GCACCTCAAA AACACCATCA TACACTAAAT 5900
CAGTAAGTTG GCAGCATCAC CCGACGCACT TTGCGCCGAA TAAATACCTG 5950
TGACGGAAGA TCACTTCGCA GAATAAATAA ATCCTGGTGT CCCTGTTGAT 6000
ACCGGGAAGC CCTGGGCCAA CTTTTGGCGA AAATGAGACG TTGATCGGCA 6050
CGTAAGAGGT TCCAACTTTC ACCATAATGA AATAAGATCA CTACCGGGCG 6100
TATTTTTTGA GTTATCGAGA TTTTCAGGAG CTAAGGAAGC TAAAATGGAG 6150
AAAAAAATCA CTGGATATAC CACCGTTGAT ATATCCCAAT GGCATCGTAA 6200
AGAACATTTT GAGGCATTTC AGTCAGTTGC TCAATGTACC TATAACCAGA 6250
CCGTTCAGCT GGATATTACG GCCTTTTTAA AGACCGTAAA GAAAAATAAG 6300
CACAAGTTTT ATCCGGCCTT TATTCACATT CTTGCCCGCC TGATGAATGC 6350
TCATCCGGAA TTC 6363

( 2 ) INFORMATION FOR SEQ ID NO:7:

-continued ( i ) SEQUENCE CHARACTERISTICS:
( A ) LENGTH: 665 amino acids
( B ) TYPE: Amino Acid
( D ) TOPOLOGY: Linear ( x i ) SEQUENCE DESCRIPTION: SEQ ID NO:7:

Met Pro Leu Asn Ile Glu Asp Glu His Arg Leu His Glu Thr Ser
1 5 10 15

Lys Glu Pro Asp Val Ser Leu Gly Ser Thr Trp Leu Ser Ala Phe
20 25 30

Pro Gln Ala Trp Ala Glu Thr Gly Gly Met Gly Leu Ala Val Arg
35 40 45

Gln Ala Pro Leu Ile Ile Pro Leu Lys Ala Thr Ser Thr Pro Val
50 55 60

Ser Ile Lys Gln Tyr Pro Met Ser Gln Glu Ala Arg Leu Gly Ile
65 70 75

Lys Pro His Ile Gln Arg Leu Leu Asp Gln Gly Ile Leu Val Pro
80 85 90

Cys Gln Ser Pro Trp Asn Thr Pro Leu Leu Pro Ile Lys Lys Pro
95 100 105

Gly Thr Asn Asp Tyr Arg Pro Val Gln Asp Leu Arg Glu Val Asn
110 115 120

Lys Arg Val Glu Asp Ile His Pro Thr Val Pro Asn Pro Tyr Asn
125 130 135

Leu Leu Ser Gly Leu Pro Pro Ser His Gln Trp Tyr Thr Val Leu
140 145 150

Asp Leu Lys Asp Ala Phe Phe Cys Leu Arg Leu His Pro Thr Ser
155 160 165

Gln Pro Leu Phe Ala Phe Glu Trp Arg Asp Pro Glu Met Gly Ile
170 175 180

Ser Gly Gln Leu Thr Trp Thr Arg Leu Pro Gln Gly Phe Lys Asn
185 190 195

Ser Pro Thr Leu Phe Asp Glu Ala Leu His Arg Asp Leu Ala Gly
200 205 210

Phe Arg Ile Gln His Pro Asp Leu Ile Leu Leu Gln Tyr Val Asp
215 220 225

Asp Leu Leu Leu Ala Ala Ser Ser Glu Leu Asp Cys Gln Gln Gly
230 235 240

Thr Arg Ala Leu Leu Gln Thr Leu Gly Asp Leu Gly Tyr Arg Ala
245 250 255

Ser Ala Lys Lys Ala Gln Ile Cys Gln Lys Gln Val Lys Tyr Leu
260 265 270

Gly Tyr Leu Leu Lys Glu Gly Gln Arg Trp Leu Thr Glu Ala Arg
275 280 285

Lys Glu Thr Val Met Gly Gln Pro Thr Pro Lys Thr Pro Arg Gln
290 295 300

Leu Arg Glu Phe Leu Gly Thr Ala Gly Phe Cys Arg Leu Trp Ile
305 310 315

Pro Gly Phe Ala Glu Met Ala Ala Pro Leu Tyr Pro Leu Thr Lys
320 325 330

Thr Gly Thr Leu Phe Asn Trp Gly Pro Asp Gln Gln Lys Ala Tyr
335 340 345

Gln Glu Ile Lys Gln Ala Leu Leu Thr Ala Pro Ala Leu Gly Leu
350 355 360

Pro Asp Leu Thr Lys Pro Phe Glu Leu Phe Val Asp Glu Lys Gln

-continued 365 370 375

Gly Tyr Ala Lys Gly Val Leu Thr Gln Lys Leu Gly Pro Trp Arg
380 385 390

Arg Pro Val Ala Tyr Leu Ser Lys Lys Leu Asp Pro Val Ala Ala
395 400 405

Gly Trp Pro Pro Cys Leu Arg Met Val Ala Ala Ile Ala Val Leu
410 415 420

Thr Lys Asp Ala Gly Lys Leu Thr Met Gly Gln Pro Leu Val Ile
425 430 435

Leu Ala Pro His Ala Val Glu Thr Leu Val Lys Gln Pro Pro Asp
440 445 450

Arg Trp Leu Ser Asn Ala Arg Met Thr His Tyr Gln Ala Leu Leu
455 460 465

Leu Asp Thr Asp Arg Val Gln Phe Gly Pro Val Val Ala Leu Asn
470 475 480

Pro Ala Thr Leu Leu Pro Leu Pro Lys Glu Gly Leu Gln His Asp
485 490 495

Cys Leu Asp Ile Leu Ala Glu Ala His Gly Thr Arg Ser Asp Leu
500 505 510

Thr Asp Gln Pro Leu Pro Asp Ala Asp His Thr Trp Tyr Thr Asp
515 520 525

Gly Ser Ser Phe Leu Gln Glu Gly Gln Arg Lys Ala Gly Ala Ala
530 535 540

Val Thr Thr Glu Thr Glu Val Ile Trp Ala Arg Ala Leu Pro Ala
545 550 555

Gly Thr Ser Ala Gln Arg Ala Glu Leu Ile Ala Leu Thr Gln Ala
560 565 570

Leu Lys Met Ala Glu Gly Lys Lys Leu Asn Val Tyr Thr Asp Ser
575 580 585

Arg Tyr Ala Phe Ala Thr Ala His Ile His Gly Glu Ile Tyr Arg
590 595 600

Arg Arg Gly Leu Leu Thr Ser Glu Gly Lys Glu Ile Lys Asn Lys
605 610 615

Gly Glu Ile Leu Ala Leu Leu Lys Ala Leu Phe Leu Pro Lys Arg
620 625 630

Leu Ser Ile Ile His Cys Pro Gly His Gln Lys Gly Asn Ser Ala
635 640 645

Glu Ala Arg Gly Asn Arg Met Ala Asp Gln Ala Ala Arg Lys Ala
650 655 660

Ala Ile Thr Glu Thr
665

( 2 ) INFORMATION FOR SEQ ID NO:8:

( i ) SEQUENCE CHARACTERISTICS:
( A ) LENGTH: 1079 amino acids
( B ) TYPE: Amino Acid
( D ) TOPOLOGY: Linear ( x i ) SEQUENCE DESCRIPTION: SEQ ID NO:8:

Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro
20 25 30

Gln Ala Trp Ala Glu Thr Gly Gly Met Gly Leu Ala Val Arg Gln
35 40 45

-continued

Ala Pro Leu Ile Ile Pro Leu Lys Ala Thr Ser Thr Pro Val Ser
50 55 60

Ile Lys Gln Tyr Pro Met Ser Gln Glu Ala Arg Leu Gly Ile Lys
65 70 75

Pro His Ile Gln Arg Leu Leu Asp Gln Gly Ile Leu Val Pro Cys
80 85 90

Gln Ser Pro Trp Asn Thr Pro Leu Leu Pro Val Lys Lys Pro Gly
95 100 105

Thr Asn Asp Tyr Arg Pro Val Gln Asp Leu Arg Glu Val Asn Lys
110 115 120

Arg Val Glu Asp Ile His Pro Thr Val Pro Asn Pro Tyr Asn Leu
125 130 135

Leu Ser Gly Leu Pro Pro Ser His Gln Trp Tyr Thr Val Leu Asp
140 145 150

Leu Lys Asp Ala Phe Phe Cys Leu Arg Leu His Pro Thr Ser Gln
155 160 165

Pro Leu Phe Ala Phe Glu Trp Arg Asp Pro Glu Met Gly Ile Ser
170 175 180

Gly Gln Leu Thr Trp Thr Arg Leu Pro Gln Gly Phe Lys Asn Ser
185 190 195

Pro Thr Leu Phe Asp Glu Ala Leu His Arg Asp Leu Ala Asp Phe
200 205 210

Arg Ile Gln His Pro Asp Leu Ile Leu Leu Gln Tyr Val Asp Asp
215 220 225

Leu Leu Leu Ala Ala Thr Ser Glu Leu Asp Cys Gln Gln Gly Thr
230 235 240

Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly
260 265 270

Tyr Leu Leu Lys Glu Gly Gln Arg Trp Leu Thr Glu Ala Arg Lys
275 280 285

Glu Thr Val Met Gly Gln Pro Thr Pro Lys Thr Pro Arg Gln Leu
290 295 300

Arg Glu Phe Leu Gly Thr Ala Gly Phe Cys Arg Leu Trp Ile Pro
305 310 315

Gly Phe Ala Glu Met Ala Ala Pro Leu Tyr Pro Leu Thr Lys Thr
320 325 330

Gly Thr Leu Phe Asn Trp Gly Pro Asp Gln Gln Lys Ala Tyr Gln
335 340 345

Glu Ile Lys Gln Ala Leu Leu Thr Ala Pro Ala Leu Gly Leu Pro
350 355 360

Asp Leu Thr Lys Pro Phe Glu Leu Phe Val Asp Glu Lys Gln Gly
365 370 375

Tyr Ala Lys Gly Val Leu Thr Gln Lys Leu Gly Pro Trp Arg Arg
380 385 390

Pro Val Ala Tyr Leu Ser Lys Lys Leu Asp Pro Val Ala Ala Gly
395 400 405

Trp Pro Pro Cys Leu Arg Met Val Ala Ala Ile Ala Val Leu Thr
410 415 420

Lys Asp Ala Gly Lys Leu Thr Met Gly Gln Pro Leu Val Ile Leu
425 430 435

Ala Pro His Ala Val Glu Ala Leu Val Lys Gln Pro Pro Asp Arg

-continued 440 445 450

Trp Leu Ser Asn Ala Arg Met Thr His Tyr Gln Ala Leu Leu Leu
455 460 465

Asp Thr Asp Arg Val Gln Phe Gly Pro Val Val Ala Leu Asn Pro
470 475 480

Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr
500 505 510

Asp Gln Pro Leu Pro Asp Ala Asp His Thr Trp Tyr Thr Asp Gly
515 520 525

Ser Ser Leu Leu Gln Glu Gly Gln Arg Lys Ala Gly Ala Ala Val
530 535 540

Thr Thr Glu Thr Glu Val Ile Trp Ala Lys Ala Leu Pro Ala Gly
545 550 555

Thr Ser Ala Gln Arg Ala Glu Leu Ile Ala Leu Thr Gln Ala Leu
560 565 570

Lys Met Ala Glu Gly Lys Lys Leu Asn Val Tyr Thr Asp Ser Arg
575 580 585

Tyr Ala Phe Ala Thr Ala His Ile His Gly Glu Ile Tyr Arg Arg
590 595 600

Arg Gly Leu Leu Thr Ser Glu Gly Lys Glu Ile Lys Asn Lys Asp
605 610 615

Glu Ile Leu Ala Leu Leu Lys Ala Leu Phe Leu Pro Lys Arg Leu
620 625 630

Ser Ile Ile His Cys Pro Gly His Gln Lys Gly His Ser Ala Glu
635 640 645

Ala Arg Gly Asn Arg Met Ala Asp Gln Ala Ala Arg Lys Ala Ala
650 655 660

Ile Thr Glu Thr Pro Asp Thr Ser Thr Leu Leu Ile Glu Asn Ser
665 670 675

Ser Pro Tyr Thr Ser Glu His Phe His Tyr Thr Val Thr Asp Ile
680 685 690

Lys Asp Leu Thr Lys Leu Gly Ala Ile Tyr Asp Lys Thr Lys Lys
695 700 705

Tyr Trp Val Tyr Gln Gly Lys Pro Val Met Pro Asp Gln Phe Thr
710 715 720

Phe Glu Leu Leu Asp Phe Leu His Gln Leu Thr His Leu Ser Phe
725 730 735

Ser Lys Met Lys Ala Leu Leu Glu Arg Ser His Ser Pro Tyr Tyr
740 745 750

Met Leu Asn Arg Asp Arg Thr Leu Lys Asn Ile Thr Glu Thr Cys
755 760 765

Lys Ala Cys Ala Gln Val Asn Ala Ser Lys Ser Ala Val Lys Gln
770 775 780

Gly Thr Arg Val Arg Gly His Arg Pro Gly Thr His Trp Glu Ile
785 790 795

Asp Phe Thr Glu Ile Lys Pro Gly Leu Tyr Gly Tyr Lys Tyr Leu
800 805 810

Leu Val Phe Ile Asp Thr Phe Ser Gly Trp Ile Glu Ala Phe Pro
815 820 825

Thr Lys Lys Glu Thr Ala Lys Val Val Thr Lys Lys Leu Leu Glu
830 835 840

-continued

Glu Ile Phe Pro Arg Phe Gly Met Pro Gln Val Leu Gly Thr Asp
845 850 855

Asn Gly Pro Ala Phe Val Ser Lys Val Ser Gln Thr Val Ala Asp
860 865 870

Leu Leu Gly Ile Asp Trp Lys Leu His Cys Ala Tyr Arg Pro Gln
875 880 885

Ser Ser Gly Gln Val Glu Arg Met Asn Arg Thr Ile Lys Glu Thr
890 895 900

Leu Thr Lys Leu Thr Leu Ala Thr Gly Ser Arg Asp Trp Val Leu
905 910 915

Leu Leu Pro Leu Ala Leu Tyr Arg Ala Arg Asn Thr Pro Gly Pro
920 925 930

His Gly Leu Thr Pro Tyr Glu Ile Leu Tyr Gly Ala Pro Pro Pro
935 940 945

Leu Val Asn Phe Pro Asp Pro Asp Met Thr Arg Val Thr Asn Ser
950 955 960

Pro Ser Leu Gln Ala His Leu Gln Ala Leu Tyr Leu Val Gln His
965 970 975

Glu Val Trp Arg Pro Leu Ala Ala Ala Tyr Gln Glu Gln Leu Asp
980 985 990

Arg Pro Val Val Pro His Pro Tyr Arg Val Gly Asp Thr Val Trp
995 1000 1005

Val Arg Arg His Gln Thr Lys Asn Leu Glu Pro Arg Trp Lys Gly
1010 1015 1020

Pro Tyr Thr Val Leu Leu Thr Thr Pro Thr Ala Leu Lys Val Asp
1025 1030 1035

Gly Ile Ala Ala Trp Ile His Ala Ala His Val Lys Ala Ala Asp
1040 1045 1050

Pro Gly Gly Gly Pro Ser Ser Arg Leu Thr Trp Arg Val Gln Arg
1055 1060 1065

Ser Gln Asn Pro Leu Lys Ile Arg Leu Thr Arg Glu Ala Pro
1070 1075 1079

( 2 ) INFORMATION FOR SEQ ID NO:9:

( i ) SEQUENCE CHARACTERISTICS:
( A ) LENGTH: 34 base pairs
( B ) TYPE: Nucleic Acid
( C ) STRANDEDNESS: Single
( D ) TOPOLOGY: Linear ( x i ) SEQUENCE DESCRIPTION: SEQ ID NO:9:

GGAAGATCTC GACTGCACGG TGCACCAATG CTTC 34

( 2 ) INFORMATION FOR SEQ ID NO:10:

( i ) SEQUENCE CHARACTERISTICS:
( A ) LENGTH: 40 base pairs
( B ) TYPE: Nucleic Acid
( C ) STRANDEDNESS: Single
( D ) TOPOLOGY: Linear ( x i ) SEQUENCE DESCRIPTION: SEQ ID NO:10:

AGGTCTAGAG GGGAATTGTT ATCCGCTCAC AATTCCACAC 40

( 2 ) INFORMATION FOR SEQ ID NO:11:

( i ) SEQUENCE CHARACTERISTICS:
( A ) LENGTH: 33 base pairs
( B ) TYPE: Nucleic Acid ( C ) STRANDEDNESS: Single
( D ) TOPOLOGY: Linear ( x i ) SEQUENCE DESCRIPTION: SEQ ID NO:11:

GAATCCCGGG GCCTAATGAG TGAGCTAACT TAC 33

( 2 ) INFORMATION FOR SEQ ID NO:12:

( i ) SEQUENCE CHARACTERISTICS:
( A ) LENGTH: 37 base pairs
( B ) TYPE: Nucleic Acid
( C ) STRANDEDNESS: Single
( D ) TOPOLOGY: Linear ( x i ) SEQUENCE DESCRIPTION: SEQ ID NO:12:

AGGATCGATA TAGTTCCTCC TTTCAGCAAA AAACCCC 37

( 2 ) INFORMATION FOR SEQ ID NO:13:

( i ) SEQUENCE CHARACTERISTICS:
( A ) LENGTH: 59 base pairs
( B ) TYPE: Nucleic Acid
( C ) STRANDEDNESS: Single
( D ) TOPOLOGY: Linear ( x i ) SEQUENCE DESCRIPTION: SEQ ID NO:13:

GAACATATGA CTTTGAATAT CGAAGATGAG CATCGTCTGC ATGAGACCTC 50

AAAAGAGCC 59

( 2 ) INFORMATION FOR SEQ ID NO:14:

( i ) SEQUENCE CHARACTERISTICS:
( A ) LENGTH: 57 base pairs
( B ) TYPE: Nucleic Acid
( C ) STRANDEDNESS: Single
( D ) TOPOLOGY: Linear ( x i ) SEQUENCE DESCRIPTION: SEQ ID NO:14:

TTTTGAGCTC TTAAGTCTCT GTGATGGCTG CCTTGCGCGC CGCTTGGTCA 50

GCCATCC 57

( 2 ) INFORMATION FOR SEQ ID NO:15:

( i ) SEQUENCE CHARACTERISTICS:
( A ) LENGTH: 4696 base pairs
( B ) TYPE: Nucleic Acid
( C ) STRANDEDNESS: Single
( D ) TOPOLOGY: Linear ( x i ) SEQUENCE DESCRIPTION: SEQ ID NO:15:

TCGAGCTCGC CCGACATTGA TTATTGACTA GTTATTAATA GTAATCAATT 50

ACGGGGTCAT TAGTTCATAG CCCATATATG GAGTTCCGCG TTACATAACT 100

TACGGTAAAT GGCCCGCCTG GCTGACCGCC CAACGACCCC CGCCCATTGA 150

CGTCAATAAT GACGTATGTT CCCATAGTAA CGCCAATAGG GACTTTCCAT 200

TGACGTCAAT GGGTGGAGTA TTTACGGTAA ACTGCCCACT TGGCAGTACA 250

TCAAGTGTAT CATATGCCAA GTACGCCCCC TATTGACGTC AATGACGGTA 300

AATGGCCCGC CTGGCATTAT GCCCAGTACA TGACCTTATG GGACTTTCCT 350

ACTTGGCAGT ACATCTACGT ATTAGTCATC GCTATTACCA TGGTGATGCG 400

GTTTTGGCAG TACATCAATG GGCGTGGATA GCGGTTTGAC TCACGGGGAT 450

TTCCAAGTCT CCACCCCATT GACGTCAATG GGAGTTTGTT TTGGCACCAA 500

-continued

| | | | | | |
|---|---|---|---|---|---|
| AATCAACGGG | ACTTTCCAAA | ATGTCGTAAC | AACTCCGCCC | CATTGACGCA | 550 |
| AATGGGCGGT | AGGCGTGTAC | GGTGGGAGGT | CTATATAAGC | AGAGCTCGTT | 600 |
| TAGTGAACCG | TCAGATCGCC | TGGAGACGCC | ATCCACGCTG | TTTTGACCTC | 650 |
| CATAGAAGAC | ACCGGGACCG | ATCCAGCCTC | CGCGGCCGGG | AACGGTGCAT | 700 |
| TGGAACGCGG | ATTCCCCGTG | CCAAGAGTGA | CGTAAGTACC | GCCTATAGAG | 750 |
| TCTATAGGCC | CACCCCCTTG | GCTTGGCCCA | CCCCCTTGGC | TTCGTTAGAA | 800 |
| CGCGGCTACA | ATTAATACAT | AACCTTATGT | ATCATACACA | TACGATTTAG | 850 |
| GTGACACTAT | AGAATAACAT | CCACTTTGCC | TTTCACATCC | ACTTTGCCTT | 900 |
| TCTCTCCACA | GGTGTCCACT | CCCAGGTCCA | ACTGCACCTC | GGTTCTATCG | 950 |
| ATTGAATTCC | CCGGGGATCC | TCTAGAGTCG | ACCTGCAGAA | GCTTGGCCGC | 1000 |
| CATGGCCCAA | CTTGTTTATT | GCAGCTTATA | ATGGTTACAA | ATAAAGCAAT | 1050 |
| AGCATCACAA | ATTTCACAAA | TAAAGCATTT | TTTTCACTGC | ATTCTAGTTG | 1100 |
| TGGTTTGTCC | AAACTCATCA | ATGTATCTTA | TCATGTCTGG | ATCGGGAATT | 1150 |
| AATTCGGCGC | AGCACCATGG | CCTGAAATAA | CCTCTGAAAG | AGGAACTTGG | 1200 |
| TTAGGTACCT | TCTGAGGCGG | AAAGAACCAG | CTGTGGAATG | TGTGTCAGTT | 1250 |
| AGGGTGTGGA | AAGTCCCCAG | GCTCCCCAGC | AGGCAGAAGT | ATGCAAAGCA | 1300 |
| TGCATCTCAA | TTAGTCAGCA | ACCAGGTGTG | GAAAGTCCCC | AGGCTCCCCA | 1350 |
| GCAGGCAGAA | GTATGCAAAG | CATGCATCTC | AATTAGTCAG | CAACCATAGT | 1400 |
| CCCGCCCCTA | ACTCCGCCCA | TCCCGCCCCT | AACTCCGCCC | AGTTCCGCCC | 1450 |
| ATTCTCCGCC | CCATGGCTGA | CTAATTTTTT | TTATTTATGC | AGAGGCCGAG | 1500 |
| GCCGCCTCGG | CCTCTGAGCT | ATTCCAGAAG | TAGTGAGGAG | GCTTTTTTGG | 1550 |
| AGGCCTAGGC | TTTTGCAAAA | AGCTGTTAAC | AGCTTGGCAC | TGGCCGTCGT | 1600 |
| TTTACAACGT | CGTGACTGGG | AAAACCCTGG | CGTTACCCAA | CTTAATCGCC | 1650 |
| TTGCAGCACA | TCCCCCTTTC | GCCAGCTGGC | GTAATAGCGA | AGAGGCCCGC | 1700 |
| ACCGATCGCC | CTTCCCAACA | GTTGCGCAGC | CTGAATGGCG | AATGGCGCCT | 1750 |
| GATGCGGTAT | TTTCTCCTTA | CGCATCTGTG | CGGTATTTCA | CACCGCATAC | 1800 |
| GTCAAAGCAA | CCATAGTACG | CGCCCTGTAG | CGGCGCATTA | AGCGCGGCGG | 1850 |
| GTGTGGTGGT | TACGCGCAGC | GTGACCGCTA | CACTTGCCAG | CGCCCTAGCG | 1900 |
| CCCGCTCCTT | TCGCTTTCTT | CCCTTCCTTT | CTCGCCACGT | TCGCCGGCTT | 1950 |
| TCCCCGTCAA | GCTCTAAATC | GGGGGCTCCC | TTTAGGGTTC | CGATTTAGTG | 2000 |
| CTTTACGGCA | CCTCGACCCC | AAAAAACTTG | ATTTGGGTGA | TGGTTCACGT | 2050 |
| AGTGGGCCAT | CGCCCTGATA | GACGGTTTTT | CGCCCTTTGA | CGTTGGAGTC | 2100 |
| CACGTTCTTT | AATAGTGGAC | TCTTGTTCCA | AACTGGAACA | ACACTCAACC | 2150 |
| CTATCTCGGG | CTATTCTTTT | GATTTATAAG | GGATTTTGCC | GATTTCGGCC | 2200 |
| TATTGGTTAA | AAAATGAGCT | GATTTAACAA | AAATTTAACG | CGAATTTTAA | 2250 |
| CAAAATATTA | ACGTTTACAA | TTTTATGGTG | CACTCTCAGT | ACAATCTGCT | 2300 |
| CTGATGCCGC | ATAGTTAAGC | CAGCCCCGAC | ACCCGCCAAC | ACCCGCTGAC | 2350 |
| GCGCCCTGAC | GGGCTTGTCT | GCTCCCGGCA | TCCGCTTACA | GACAAGCTGT | 2400 |
| GACCGTCTCC | GGGAGCTGCA | TGTGTCAGAG | GTTTTCACCG | TCATCACCGA | 2450 |
| AACGCGCGAG | ACGAAAGGGC | CTCGTGATAC | GCCTATTTTT | ATAGGTTAAT | 2500 |

-continued

```
GTCATGATAA TAATGGTTTC TTAGACGTCA GGTGGCACTT TTCGGGGAAA 2550
TGTGCGCGGA ACCCCTATTT GTTTATTTTT CTAAATACAT TCAAATATGT 2600
ATCCGCTCAT GAGACAATAA CCCTGATAAA TGCTTCAATA ATATTGAAAA 2650
AGGAAGAGTA TGAGTATTCA ACATTTCCGT GTCGCCCTTA TTCCCTTTTT 2700
TGCGGCATTT TGCCTTCCTG TTTTTGCTCA CCCAGAAACG CTGGTGAAAG 2750
TAAAAGATGC TGAAGATCAG TTGGGTGCAC GAGTGGGTTA CATCGAACTG 2800
GATCTCAACA GCGGTAAGAT CCTTGAGAGT TTTCGCCCCG AAGAACGTTT 2850
TCCAATGATG AGCACTTTTA AAGTTCTGCT ATGTGGCGCG GTATTATCCC 2900
GTATTGACGC CGGGCAAGAG CAACTCGGTC GCCGCATACA CTATTCTCAG 2950
AATGACTTGG TTGAGTACTC ACCAGTCACA GAAAAGCATC TTACGGATGG 3000
CATGACAGTA AGAGAATTAT GCAGTGCTGC CATAACCATG AGTGATAACA 3050
CTGCGGCCAA CTTACTTCTG ACAACGATCG GAGGACCGAA GGAGCTAACC 3100
GCTTTTTTGC ACAACATGGG GGATCATGTA ACTCGCCTTG ATCGTTGGGA 3150
ACCGGAGCTG AATGAAGCCA TACCAAACGA CGAGCGTGAC ACCACGATGC 3200
CTGTAGCAAT GGCAACAACG TTGCGCAAAC TATTAACTGG CGAACTACTT 3250
ACTCTAGCTT CCCGGCAACA ATTAATAGAC TGGATGGAGG CGGATAAAGT 3300
TGCAGGACCA CTTCTGCGCT CGGCCCTTCC GGCTGGCTGG TTTATTGCTG 3350
ATAAATCTGG AGCCGGTGAG CGTGGGTCTC GCGGTATCAT TGCAGCACTG 3400
GGGCCAGATG GTAAGCCCTC CCGTATCGTA GTTATCTACA CGACGGGGAG 3450
TCAGGCAACT ATGGATGAAC GAAATAGACA GATCGCTGAG ATAGGTGCCT 3500
CACTGATTAA GCATTGGTAA CTGTCAGACC AAGTTTACTC ATATATACTT 3550
TAGATTGATT TAAAACTTCA TTTTTAATTT AAAAGGATCT AGGTGAAGAT 3600
CCTTTTTGAT AATCTCATGA CCAAAATCCC TTAACGTGAG TTTTCGTTCC 3650
ACTGAGCGTC AGACCCCGTA GAAAAGATCA AAGGATCTTC TTGAGATCCT 3700
TTTTTTCTGC GCGTAATCTG CTGCTTGCAA ACAAAAAAAC CACCGCTACC 3750
AGCGGTGGTT TGTTTGCCGG ATCAAGAGCT ACCAACTCTT TTTCCGAAGG 3800
TAACTGGCTT CAGCAGAGCG CAGATACCAA ATACTGTTCT TCTAGTGTAG 3850
CCGTAGTTAG GCCACCACTT CAAGAACTCT GTAGCACCGC CTACATACCT 3900
CGCTCTGCTA ATCCTGTTAC CAGTGGCTGC TGCCAGTGGC GATAAGTCGT 3950
GTCTTACCGG GTTGGACTCA AGACGATAGT TACCGGATAA GGCGCAGCGG 4000
TCGGGCTGAA CGGGGGGTTC GTGCACACAG CCCAGCTTGG AGCGAACGAC 4050
CTACACCGAA CTGAGATACC TACAGCGTGA GCTATGAGAA AGCGCCACGC 4100
TTCCCGAAGG GAGAAAGGCG GACAGGTATC CGGTAAGCGG CAGGGTCGGA 4150
ACAGGAGAGC GCACGAGGGA GCTTCCAGGG GGAAACGCCT GGTATCTTTA 4200
TAGTCCTGTC GGGTTTCGCC ACCTCTGACT TGAGCGTCGA TTTTTGTGAT 4250
GCTCGTCAGG GGGGCGGAGC CTATGGAAAA ACGCCAGCAA CGCGGCCTTT 4300
TTACGGTTCC TGGCCTTTTG CTGGCCTTTT GCTCACATGT TCTTTCCTGC 4350
GTTATCCCCT GATTCTGTGG ATAACCGTAT TACCGCCTTT GAGTGAGCTG 4400
ATACCGCTCG CCGCAGCCGA ACGACCGAGC GCAGCGAGTC AGTGAGCGAG 4450
GAAGCGGAAG AGCGCCCAAT ACGCAAACCG CCTCTCCCCG CGCGTTGGCC 4500
```

-continued

GATTCATTAA TGCAGCTGGC ACGACAGGTT TCCCGACTGG AAAGCGGGCA 4550

GTGAGCGCAA CGCAATTAAT GTGAGTTAGC TCACTCATTA GGCACCCCAG 4600

GCTTTACACT TTATGCTTCC GGCTCGTATG TTGTGTGGAA TTGTGAGCGG 4650

ATAACAATTT CACACAGGAA ACAGCTATGA CATGATTACG AATTAA 4696

( 2 ) INFORMATION FOR SEQ ID NO:16:

( i ) SEQUENCE CHARACTERISTICS:
( A ) LENGTH: 5158 base pairs
( B ) TYPE: Nucleic Acid
( C ) STRANDEDNESS: Single
( D ) TOPOLOGY: Linear ( x i ) SEQUENCE DESCRIPTION: SEQ ID NO:16:

TCGAGCTCGC CCGACATTGA TTATTGACTA GTTATTAATA GTAATCAATT 50

ACGGGGTCAT TAGTTCATAG CCCATATATG GAGTTCCGCG TTACATAACT 100

TACGGTAAAT GGCCCGCCTG GCTGACCGCC CAACGACCCC CGCCCATTGA 150

CGTCAATAAT GACGTATGTT CCCATAGTAA CGCCAATAGG GACTTTCCAT 200

TGACGTCAAT GGGTGGAGTA TTTACGGTAA ACTGCCCACT TGGCAGTACA 250

TCAAGTGTAT CATATGCCAA GTACGCCCCC TATTGACGTC AATGACGGTA 300

AATGGCCCGC CTGGCATTAT GCCCAGTACA TGACCTTATG GGACTTTCCT 350

ACTTGGCAGT ACATCTACGT ATTAGTCATC GCTATTACCA TGGTGATGCG 400

GTTTTGGCAG TACATCAATG GGCGTGGATA GCGGTTTGAC TCACGGGGAT 450

TTCCAAGTCT CCACCCCATT GACGTCAATG GGAGTTTGTT TTGGCACCAA 500

AATCAACGGG ACTTTCCAAA ATGTCGTAAC AACTCCGCCC CATTGACGCA 550

AATGGGCGGT AGGCGTGTAC GGTGGGAGGT CTATATAAGC AGAGCTCGTT 600

TAGTGAACCG TCAGATCGCC TGGAGACGCC ATCCACGCTG TTTTGACCTC 650

CATAGAAGAC ACCGGGACCG ATCCAGCCTC CGCGGCCGGG AACGGTGCAT 700

TGGAACGCGG ATTCCCCGTG CCAAGAGTGA CGTAAGTACC GCCTATAGAG 750

TCTATAGGCC CACTTGGCTT GGCCCACCCC CTTGGCTTCG TTAGAACGCG 800

GCTACAATTA ATACATAACC TTATGTATCA TACACATACG ATTTAGGTGA 850

CACTATAGAA TAACATCCAC TTTGCCTTTC ACATCCACTT TGCCTTTCTC 900

TCCACAGGTG TCCACTCCCA GGTCCAACTG CACCTCGGTT CTATCGATTG 950

AATTCCCCGG GGATCCTCTA GAGATCCCTC GACCTCGAGA TCCATTGTGC 1000

TGGCGCGGAT TCTTTATCAC TGATAAGTTG GTGGACATAT TATGTTTATC 1050

AGTGATAAAG TGTCAAGCAT GACAAAGTTG CAGCCGAATA CAGTGATCCG 1100

TGCCGCCCTA GACCTGTTGA ACGAGGTCGG CGTAGACGGT CTGACGACAC 1150

GCAAACTGGC GGAACGGTTG GGGGTTCAGC AGCCGGCGCT TTACTGGCAC 1200

TTCAGGAACA AGCGGGCGCT GCTCGACGCA CTGGCCGAAG CCATGCTGGC 1250

GGAGAATCAT AGCACTTCGG TGCCGAGAGC CGACGACGAC TGGCGCTCAT 1300

TTCTGATCGG GAATGCCCGC AGCTTCAGGC AGGCGCTGCT CGCCTACCGC 1350

CAGCACAATG GATCTCGAGG GATCTTCCAT ACCTACCAGT TCTGCGCCTG 1400

CAGGTCGCGG CCTAGGGATA ACAGGGTAAT GCGGCCGCGT CGACCTGCAG 1450

AAGCTTGGCC GCCATGGCCC AACTTGTTTA TTGCAGCTTA TAATGGTTAC 1500

-continued

| | | | | | |
|---|---|---|---|---|---|
| AAATAAAGCA | ATAGCATCAC | AAATTTCACA | AATAAAGCAT | TTTTTTCACT | 1550 |
| GCATTCTAGT | TGTGGTTTGT | CCAAACTCAT | CAATGTATCT | TATCATGTCT | 1600 |
| GGATCGGGAA | TTAATTCGGC | GCAGCACCAT | GGCCTGAAAT | AACCTCTGAA | 1650 |
| AGAGGAACTT | GGTTAGGTAC | CTTCTGAGGC | GGAAAGAACC | AGCTGTGGAA | 1700 |
| TGTGTGTCAG | TTAGGGTGTG | GAAAGTCCCC | AGGCTCCCCA | GCAGGCAGAA | 1750 |
| GTATGCAAAG | CATGCATCTC | AATTAGTCAG | CAACCAGGTG | TGGAAAGTCC | 1800 |
| CCAGGCTCCC | CAGCAGGCAG | AAGTATGCAA | AGCATGCATC | TCAATTAGTC | 1850 |
| AGCAACCATA | GTCCCGCCCC | TAACTCCGCC | CATCCCGCCC | CTAACTCCGC | 1900 |
| CCAGTTCCGC | CCATTCTCCG | CCCCATGGCT | GACTAATTTT | TTTTATTTAT | 1950 |
| GCAGAGGCCG | AGGCCGCCTC | GGCCTCTGAG | CTATTCCAGA | AGTAGTGAGG | 2000 |
| AGGCTTTTTT | GGAGGCCTAG | GCTTTTGCAA | AAAGCTGTTA | ACAGCTTGGC | 2050 |
| ACTGGCCGTC | GTTTTACAAC | GTCGTGACTG | GGAAAACCCT | GGCGTTACCC | 2100 |
| AACTTAATCG | CCTTGCAGCA | CATCCCCCTT | TCGCCAGCTG | GCGTAATAGC | 2150 |
| GAAGAGGCCC | GCACCGATCG | CCCTTCCCAA | CAGTTGCGCA | GCCTGAATGG | 2200 |
| CGAATGGCGC | CTGATGCGGT | ATTTTCTCCT | TACGCATCTG | TGCGGTATTT | 2250 |
| CACACCGCAT | ACGTCAAAGC | AACCATAGTA | CGCGCCCTGT | AGCGGCGCAT | 2300 |
| TAAGCGCGGC | GGGTGTGGTG | GTTACGCGCA | GCGTGACCGC | TACACTTGCC | 2350 |
| AGCGCCCTAG | CGCCCGCTCC | TTTCGCTTTC | TTCCCTTCCT | TTCTCGCCAC | 2400 |
| GTTCGCCGGC | TTTCCCCGTC | AAGCTCTAAA | TCGGGGGCTC | CCTTTAGGGT | 2450 |
| TCCGATTTAG | TGCTTTACGG | CACCTCGACC | CCAAAAAACT | TGATTTGGGT | 2500 |
| GATGGTTCAC | GTAGTGGGCC | ATCGCCCTGA | TAGACGGTTT | TTCGCCCTTT | 2550 |
| GACGTTGGAG | TCCACGTTCT | TTAATAGTGG | ACTCTTGTTC | CAAACTGGAA | 2600 |
| CAACACTCAA | CCCTATCTCG | GGCTATTCTT | TTGATTTATA | AGGGATTTTG | 2650 |
| CCGATTTCGG | CCTATTGGTT | AAAAAATGAG | CTGATTTAAC | AAAAATTTAA | 2700 |
| CGCGAATTTT | AACAAAATAT | TAACGTTTAC | AATTTTATGG | TGCACTCTCA | 2750 |
| GTACAATCTG | CTCTGATGCC | GCATAGTTAA | GCCAGCCCCG | ACACCCGCCA | 2800 |
| ACACCCGCTG | ACGCGCCCTG | ACGGGCTTGT | CTGCTCCCGG | CATCCGCTTA | 2850 |
| CAGACAAGCT | GTGACCGTCT | CCGGGAGCTG | CATGTGTCAG | AGGTTTTCAC | 2900 |
| CGTCATCACC | GAAACGCGCG | AGACGAAAGG | GCCTCGTGAT | ACGCCTATTT | 2950 |
| TTATAGGTTA | ATGTCATGAT | AATAATGGTT | TCTTAGACGT | CAGGTGGCAC | 3000 |
| TTTTCGGGGA | AATGTGCGCG | GAACCCCTAT | TTGTTTATTT | TTCTAAATAC | 3050 |
| ATTCAAATAT | GTATCCGCTC | ATGAGACAAT | AACCCTGATA | AATGCTTCAA | 3100 |
| TAATATTGAA | AAAGGAAGAG | TATGAGTATT | CAACATTTCC | GTGTCGCCCT | 3150 |
| TATTCCCTTT | TTTGCGGCAT | TTTGCCTTCC | TGTTTTTGCT | CACCCAGAAA | 3200 |
| CGCTGGTGAA | AGTAAAAGAT | GCTGAAGATC | AGTTGGGTGC | ACGAGTGGGT | 3250 |
| TACATCGAAC | TGGATCTCAA | CAGCGGTAAG | ATCCTTGAGA | GTTTTCGCCC | 3300 |
| CGAAGAACGT | TTTCCAATGA | TGAGCACTTT | TAAAGTTCTG | CTATGTGGCG | 3350 |
| CGGTATTATC | CCGTATTGAC | GCCGGGCAAG | AGCAACTCGG | TCGCCGCATA | 3400 |
| CACTATTCTC | AGAATGACTT | GGTTGAGTAC | TCACCAGTCA | CAGAAAAGCA | 3450 |
| TCTTACGGAT | GGCATGACAG | TAAGAGAATT | ATGCAGTGCT | GCCATAACCA | 3500 |

-continued

| | | | | | |
|---|---|---|---|---|---|
| TGAGTGATAA | CACTGCGGCC | AACTTACTTC | TGACAACGAT | CGGAGGACCG | 3550 |
| AAGGAGCTAA | CCGCTTTTTT | GCACAACATG | GGGGATCATG | TAACTCGCCT | 3600 |
| TGATCGTTGG | GAACCGGAGC | TGAATGAAGC | CATACCAAAC | GACGAGCGTG | 3650 |
| ACACCACGAT | GCCTGTAGCA | ATGGCAACAA | CGTTGCGCAA | ACTATTAACT | 3700 |
| GGCGAACTAC | TTACTCTAGC | TTCCCGGCAA | CAATTAATAG | ACTGGATGGA | 3750 |
| GGCGGATAAA | GTTGCAGGAC | CACTTCTGCG | CTCGGCCCTT | CCGGCTGGCT | 3800 |
| GGTTTATTGC | TGATAAATCT | GGAGCCGGTG | AGCGTGGGTC | TCGCGGTATC | 3850 |
| ATTGCAGCAC | TGGGGCCAGA | TGGTAAGCCC | TCCCGTATCG | TAGTTATCTA | 3900 |
| CACGACGGGG | AGTCAGGCAA | CTATGGATGA | ACGAAATAGA | CAGATCGCTG | 3950 |
| AGATAGGTGC | CTCACTGATT | AAGCATTGGT | AACTGTCAGA | CCAAGTTTAC | 4000 |
| TCATATATAC | TTTAGATTGA | TTTAAAACTT | CATTTTTAAT | TTAAAAGGAT | 4050 |
| CTAGGTGAAG | ATCCTTTTTG | ATAATCTCAT | GACCAAAATC | CCTTAACGTG | 4100 |
| AGTTTTCGTT | CCACTGAGCG | TCAGACCCCG | TAGAAAAGAT | CAAAGGATCT | 4150 |
| TCTTGAGATC | CTTTTTTTCT | GCGCGTAATC | TGCTGCTTGC | AAACAAAAAA | 4200 |
| ACCACCGCTA | CCAGCGGTGG | TTTGTTTGCC | GGATCAAGAG | CTACCAACTC | 4250 |
| TTTTTCCGAA | GGTAACTGGC | TTCAGCAGAG | CGCAGATACC | AAATACTGTT | 4300 |
| CTTCTAGTGT | AGCCGTAGTT | AGGCCACCAC | TTCAAGAACT | CTGTAGCACC | 4350 |
| GCCTACATAC | CTCGCTCTGC | TAATCCTGTT | ACCAGTGGCT | GCTGCCAGTG | 4400 |
| GCGATAAGTC | GTGTCTTACC | GGGTTGGACT | CAAGACGATA | GTTACCGGAT | 4450 |
| AAGGCGCAGC | GGTCGGGCTG | AACGGGGGGT | TCGTGCACAC | AGCCCAGCTT | 4500 |
| GGAGCGAACG | ACCTACACCG | AACTGAGATA | CCTACAGCGT | GAGCTATGAG | 4550 |
| AAAGCGCCAC | GCTTCCCGAA | GGGAGAAAGG | CGGACAGGTA | TCCGGTAAGC | 4600 |
| GGCAGGGTCG | GAACAGGAGA | GCGCACGAGG | GAGCTTCCAG | GGGGAAACGC | 4650 |
| CTGGTATCTT | TATAGTCCTG | TCGGGTTTCG | CCACCTCTGA | CTTGAGCGTC | 4700 |
| GATTTTTGTG | ATGCTCGTCA | GGGGGGCGGA | GCCTATGGAA | AAACGCCAGC | 4750 |
| AACGCGGCCT | TTTTACGGTT | CCTGGCCTTT | TGCTGGCCTT | TTGCTCACAT | 4800 |
| GTTCTTTCCT | GCGTTATCCC | CTGATTCTGT | GGATAACCGT | ATTACCGCCT | 4850 |
| TTGAGTGAGC | TGATACCGCT | CGCCGCAGCC | GAACGACCGA | GCGCAGCGAG | 4900 |
| TCAGTGAGCG | AGGAAGCGGA | AGAGCGCCCA | ATACGCAAAC | CGCCTCTCCC | 4950 |
| CGCGCGTTGG | CCGATTCATT | AATGCAGCTG | GCACGACAGG | TTTCCCGACT | 5000 |
| GGAAAGCGGG | CAGTGAGCGC | AACGCAATTA | ATGTGAGTTA | GCTCACTCAT | 5050 |
| TAGGCACCCC | AGGCTTTACA | CTTTATGCTT | CCGGCTCGTA | TGTTGTGTGG | 5100 |
| AATTGTGAGC | GGATAACAAT | TTCACACAGG | AAACAGCTAT | GACATGATTA | 5150 |
| CGAATTAA | | | | | 5158 |

I claim:

1. A method of producing double stranded cDNA (dscDNA) from mRNA comprising transforming a cell producing reverse transcriptase with a vector in which the 5' end of a mRNA molecule having a 5' oligonucleotide cap is ligated to a single stranded 5' overhang complementary to said oligonucleotide cap, and the 3' end of said mRNA molecule is ligated to a single stranded 3' overhang complementary to the 3' end of said mRNA molecule.

2. The method of claim 1 wherein the mRNA is poly(A)$^+$ mRNA and 3' overhang of the vector is an oligo d(T) sequence.

3. The method of claim 1 wherein said cell is transformed with nucleotide sequence encoding reverse transcriptase.

4. The method of claim 3 wherein said cell is transformed with a vector encoding reverse transcriptase.

5. A method for producing double stranded cDNA (dscDNA) from mRNA comprising transforming a recombinant host cell with a first vector in which the 5' end of a mRNA molecule having a 5' oligonucleotide cap is ligated to a single stranded 5' overhang complementary to said oligonucleotide cap, and the 3' end of said mRNA molecule is ligated to a single stranded 3' overhang complementary to the 3' end of said mRNA molecule, and a second vector comprising a nucleotide sequence encoding reverse transcriptase.

6. The method of claim 5 wherein said first and second vectors are cotransfected, or transfected one after the other, into said recombinant host cell.

7. A method for producing double stranded cDNA (dscDNA) from mRNA comprising transforming a recombinant host cell with a vector comprising a nucleotide sequence encoding a reverse transcriptase, and a mRNA molecule having a 5'oligonucleotide cap, the 5' end of which is ligated to a single stranded 5' overhang complementary to said oligonucleotide cap, and the 3' end of which is ligated to a single stranded 3' overhang complementary to the 3' end of said mRNA molecule.

8. A method of constructing a cDNA library from a population of mRNA molecules comprising:

(a) ligating the 5' end of the mRNA molecules to an oligonucleotide cap;

(b) capturing the tagged mRNAs in a vector having a single stranded 5' overhang complementary to the oligonucleotide cap and single stranded 3' overhang complementary to the 3' end of the mRNA so that both ends of the mRNA are ligated to the vector; and, (c) transforming a cell producing reverse transcriptase with the vectors so that the reverse transcriptase initiates the conversion of the mRNAs into dscDNA to form the cDNA library.

9. The method of claim 8 wherein the mRNA is poly(A)$^+$ mRNA and 3' overhang of the vector is an oligo d(T) sequence.

10. The method of claim 8 wherein the mRNA molecules are normalized prior to step (a) to increase the representation of low abundance mRNA species in the population.

11. The method of claim 10 wherein the normalization comprises the steps of:

(i) binding the poly(A)$^+$ mRNAs to oligo d(T) coated substrate;

(ii) synthesizing all or part of a cDNA strands that are complementary to the mRNA;

(iii) denaturing the cDNA and mRNA strands;

(iv) annealing the mRNAs to the substrate bound cDNAs under conditions such that high abundant mRNAs anneal to the substrate bound cDNAs and low abundant mRNAs do not anneal; and, (v) collecting a fraction containing the low abundant mRNAs.

12. The method of claim 8 wherein full length mRNA is selected by treatment with phosphatase and pyrophosphatase prior to ligation to the oligonucleotide cap.

13. The method of claim 8 further comprising expressing the dscDNA and screening for the production of a target polypeptide.

14. The method of claim 8 wherein said cell is transformed with a nucleotide sequence encoding reverse transcriptase.

15. The method of claim 14 wherein said cell is transformed with a vector encoding reverse transcriptase.

16. The method of claim 15 wherein the cell is transformed with a vector encoding the reverse transcriptase of Moloney murine leukemia virus.

17. The method of claim 16 wherein production of the reverse transcriptase is induced prior to transfection of the cell with the vector containing the mRNA.

18. The method of claim 8 wherein the cell is a prokaryotic host cell.

19. The method of claim 18 wherein the prokaryotic host cell is *E. coli.*

20. The method of claim 8 wherein the cell is an eukaryotic host cell.

21. The method of claim 20 wherein the eukaryotic host cell is a mammalian cell line.

22. The method of claim 8 wherein the overhangs are engineered to have restriction sites.

23. The method of claim 22 further comprising cleaving the vector at the restriction sites to release the dscDNA.

24. The method of claim 8 wherein the overhangs on 5' and 3' ends of vectors are non-complementary.

25. The method of claim 15 wherein the vector comprising the mRNA and the reverse transcriptase producing vector have different origins of replication.

26. A method which comprises, having constructed a cDNA library from a population of mRNA molecules by:

(a) ligating the 5' end of the mRNA molecules to an oligonucleotide cap;

(b) using a vector having a single stranded 5' overhang complementary to the oligonucleotide cap and single stranded 3' overhang complementary to the 3' end of the mRNA to capture the tagged mRNA so that both ends of the mRNA are ligated to the vector; and, (c) transforming a cell containing the reverse transcriptase producing vector with the vectors so that the reverse transcriptase converts the mRNAs into dscDNA to form the cDNA library;

the further step of screening for target dscDNA or expression of a target polypeptide.

27. The method of claim 26 wherein the target dscDNA encodes a mammalian polypeptide comprising a signal sequence.

28. The method of claim 27 wherein screening is performed by (a) ligating said cDNA library to a DNA encoding a non-secreted yeast invertase, (b) transforming the ligated DNA into a host cell, (c) isolating DNA containing mammalian cDNA ligated to the DNA encoding the non-secreted yeast invertase from the transformed host cell, (d) transforming the DNA of step (c) into a yeast cell which does not contain a functional invertase gene, and (e) selecting transformed host cells from step (d) which are capable of growth on sucrose or raffinose.

29. A recombinant host cell transformed with:

(a) a first vector comprising a single stranded mRNA sequence, the mRNA sequence having a 5' oligonucleotide cap sequence which is complementary to a 5' overhang of the vector and a 3' sequence which is complementary to a 3' overhang of the vector, the overhangs and sequences annealing together to retain the mRNA sequence in the vector; and, (b) a second vector comprising nucleic acid encoding reverse transcriptase; wherein expression of the reverse transcriptase converts the mRNA into dscDNA.

30. A recombinant host cell of claim 29 which is a prokaryotic cell.

31. The recombinant host cell of claim 30 which is *E. coli.*

32. An isolated nucleic acid molecule encoding the xenotropic murine leukemia virus reverse transcriptase (xM-MuLV) (SEQ. ID. NO: 8).

33. xM-MuLV encoded by the nucleic acid molecule of claim 32.

34. An expression vector containing the nucleic acid molecule of claim 32.

35. A recombinant host cell transformed with a nucleic acid molecule of claim 32.

* * * * *

UNITED STATES PATENT AND TRADEMARK OFFICE

CERTIFICATE OF CORRECTION

PATENT NO. : 5,891,637

DATED : April 6, 1999

INVENTOR(S) : Siegfried J.W. Ruppert

It is certified that error appears in the above-indentified patent and that said Letters Patent is hereby corrected as shown below:

On the title page, item [63] change "Continuation of Ser. No. 732,861, Oct. 15, 1996, abandoned" to --U.S. Provisional Application Serial No. 60/126,428, filed October 15, 1996, abandoned.--

Signed and Sealed this

Twenty-third Day of November, 1999

Attest:

Q. TODD DICKINSON

*Attesting Officer*

*Acting Commissioner of Patents and Trademarks*